US011319591B2

(12) United States Patent
Saint-Andre et al.

(10) Patent No.: US 11,319,591 B2
(45) Date of Patent: May 3, 2022

(54) CORE TRANSCRIPTIONAL CIRCUITRY IN HUMAN CELLS AND METHODS OF USE THEREOF

(71) Applicant: Whitehead institute for Biomedical Research, Cambridge, MA (US)

(72) Inventors: Violaine Saint-Andre, Cambridge, MA (US); Brian J. Abraham, Cambridge, MA (US); Zi Peng Fan, Waltham, MA (US); Tong Ihn Lee, Somerville, MA (US); Richard A. Young, Boston, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 15/390,275

(22) Filed: Dec. 23, 2016

(65) Prior Publication Data

US 2017/0327890 A1 Nov. 16, 2017

Related U.S. Application Data

(63) Continuation-in-part of application No. 14/663,056, filed on Mar. 19, 2015, now abandoned.

(60) Provisional application No. 62/387,469, filed on Dec. 23, 2015, provisional application No. 61/955,764, filed on Mar. 19, 2014.

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/136* (2013.01); *C12Q 2600/156* (2013.01)

(58) Field of Classification Search
CPC combination set(s) only.
See application file for complete search history.

(56) References Cited

U.S. PATENT DOCUMENTS

| | | | |
|---|---|---|---|
| 9,181,580 B2 | 11/2015 | Young et al. | |
| 2005/0188432 A1 | 8/2005 | Li et al. | |
| 2010/0256008 A1 | 10/2010 | Ren et al. | |
| 2010/0311048 A1 | 12/2010 | Sauka-Spengler et al. | |
| 2014/0287932 A1* | 9/2014 | Hnisz | C12N 15/1034 506/2 |
| 2014/0296218 A1 | 10/2014 | Young et al. | |
| 2015/0337376 A1 | 11/2015 | Saint-Andre | |
| 2016/0237490 A1 | 8/2016 | Hnisz | |

FOREIGN PATENT DOCUMENTS

WO WO 2014/066848 5/2014

OTHER PUBLICATIONS

Tolani et al "Targeting Myc in KSHV-associated primary effusion lymphoma with BET bromodomain inhibitors" Oncogene May 2014 vol. 33, No. 22, pp. 2928-2937 (published online Jun. 24, 2013). (Year: 2013).*
Whyte et al "Master Transcription Factors and Mediator Establish Super-Enhancers at Key Cell Identity Genes" (Cell vol. 153, pp. 2017-2319, Apr. 11, 2013). (Year: 2013).*
Didych et al (Molecular Biology, 2015 vol. 49, No. 6, pp. 818-824). (Year: 2015).*
Hnisz et al in "Super-Enhancers in the Control of Cell Identity and Disease" (Cell vol. 155, Nov. 7, 2013, pp. 934-947). (Year: 2013).*
Barrera, et al., "Genome-wide mapping and analysis of active promoters in mouse embryonic stem cells and adult organs", *Genome Res*, 18(1), 46-59; 2008.
Blow, et al., "ChIP-seq identification of Weakly Conserved Heart Enhancers", *Nat Genet*, 42(9), 806-810; 2010.
Chen, et al., "Phospho-MED1-enhanced UBE2C locus looping drives castration-resistant prostate cancer growth", *The EMBO Journal*, 30(12): 2405-2419; 2011.
Chen, et al., "Enhancer identification in mouse embryonic stem cells using integrative modeling of chromatin and genomic features," *BMC genomics*, (152); 1-19; 2012.
Creyghton, M.P., et al., "Histone H3K27ac separates active from poised enhancers and predicts developmental state," *Proceedings of the National Academy of Sciences USA*, 107, 21931-21936; 2010.
Delmore, J.E., et al., "BET bromodomain inhibition as a therapeutic strategy to target c-Myc," *Cell*, 146, 904-917; 2011.
Ho, L., et al., "An embryonic stem cell chromatin remodeling complex, esBAF, is an essential component of the core pluripotency transcriptional network," *Proceedings of the National Academy of Sciences of the United States of America*, 106(13), 5187-5191; 2009.
Kagey. M.H., et al., "Mediator and cohesion connect gene expression and chromatin architecture," *Nature*, 467, 430-435; 2010.
Li, et al., "A global transcriptional regulatory role for c-Myc in Burkitt's lymphoma cells", *PNAS*, 100(14), 8164-8169; 2003.
Ong, C.T. & Corces, V.G., "Enhancer function: New insights into the regulation of tissue-specific gene expression," *Nature Reviews Genetics*, 12(4), 283-293; 2011.
Sakabe, N.J., et al., "Transcriptional enhancers in development and disease," *Genome Biology*, 13(238), 1-11; 2012.
Visel, et al., "Functional autonomy of distant-acting human enhancers" , *Genomics*, 93, 509-513: 2008.
Zeng, et al., "In vivo dual cross-linking for identification of indirect DNA-associated proteins by chromatin immunopreciptiation", *Bio Techniques*, 41(6), 694, 696, 698; 2006.
Zhang, et al., "Bromodomain-containing protein 4 (BRD4) Regulates RNA Polymerase II Serine 2 Phosphorylation in Human CD4+ T cells", JBC, 287: 43137-43155 (2012).
Whyte, Warren A., et al. "Master Transcription Factors and Mediator Establish Super-Enhancers at Key Cell Identity Genes." Cell 153.2 (2013): 307-319.

(Continued)

*Primary Examiner* — Catherine S Hibbert
(74) *Attorney, Agent, or Firm* — Morse, Barnes-Brown & Pendleton, P.C.; Lisa M. Warren, Esq.

(57) ABSTRACT

Disclosed are methods for identifying the core regulatory circuitry or cell identity program of a cell or tissue, and related methods of diagnoses, screening, and treatment involving the core regulatory circuitry and/or cell identity programs identified using the methods.

4 Claims, 23 Drawing Sheets

(56) References Cited

OTHER PUBLICATIONS

Lovén, Jakob, et al. "Selective Inhibition of Tumor Oncogenes by Disruption of Super-Enhancers." Cell 153.2 (2013): 320-334.

Hnisz, Denes, et al. "Super-enhancers in the control of cell identity and disease." Cell 155.4 (2013): 934-947.

Pott, Sebastian, and Jason D. Lieb. "What are Super-Enhancers?." Nature genetics 47.1 (2014): 8-12.

Hnisz, Denes, et al. "Convergence of Developmental and Oncogenic Signaling Pathways at Transciptional Super-Enhancers." Molecular cell 58.2 (2015): 362-370.

Rye, Morten, et al. "Clustered ChIP-Seq-defined transcription factor binding sites and histone modifications map distinct classes of regulatory elements." BMC Biology 9.80 (2011).

Gordon, David F., et al. "MED220/thyroid recsptor-associated protein 220 functions as a transcriptional coactivator with Pit-1 and GATA-2 on the thyrotropin-β promoter in thyrotropes." *Molecular Endocrinology* 20(5) (2006): 1073-1089.

International Search Report for International Application PCT/US2013/066957, dated Feb. 27, 2014.

Extended European Search Report in Application No. EP 13 84 8637, dated Apr. 28, 2016.

Non-Final Office Action in U.S. Appl. No. 14/063,337, (listed on SB-08 as US 2014-0296218), dated Feb. 20, 2015.

Non-Final Office Action in U.S. Appl. No. 14/523,560, dated Mar. 13, 2015.

Supplemental Notice of Allowance in U.S. Appl. No. 14/523,560, dated Sep. 23, 2015.

Notice of Allowance for in U.S. Appl. No. 14/523,560, dated Aug. 20, 2015.

Office Action in U.S. Appl. No. 14/873,962, dated Sep. 8, 2016.

Final Office Action in U.S. Appl. No. 14/873,962, dated Apr. 17, 2017.

Non-Final Office Action in U.S. Appl. No. 14/873,962, dated Dec. 11, 2017.

Notice of Allowance in U.S. Appl. No. 14/873,962, dated Jun. 27, 2018.

* cited by examiner

*8A*
| OCT4-GFP fluorescence changes | | Nuclei number changes | |
| Rank for mean of z-scores (% of TFs) | | Rank for mean of z-score (% of TFs) | |
|---|---|---|---|
| POU5F1 | 0 | NR5A1 | 4 |
| ZIC3 | 5 | POU5F1 | 9 |
| NANOG | 5 | NANOG | 11 |
| RARG | 27 | SOX21 | 19 |
| SOX2 | 34 | ZIC3 | 22 |
| MYB | 39 | SOX2 | 24 |
| NR5A1 | 64 | RARG | 31 |
| FOXO1 | 83 | RORA | 33 |
| RORA | 86 | FOXO1 | 38 |
| SOX21 | 89 | MYB | 66 |
*8B*
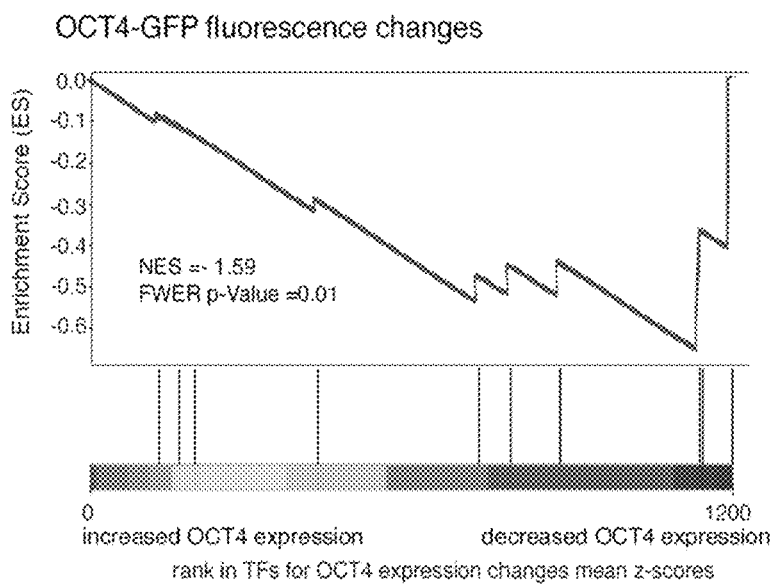
*8C*
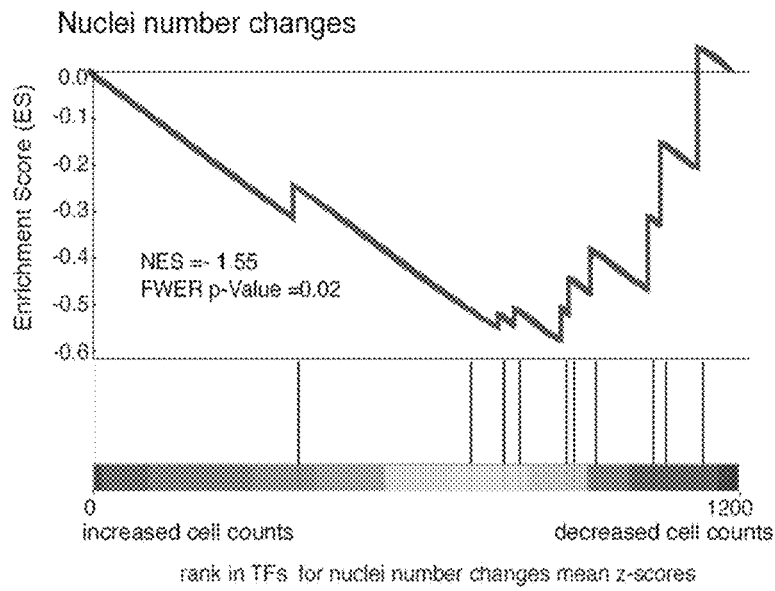
FIGS. 8A-8C under ROI-HG002668 awarded by the National institutes of
CORE TRANSCRIPTIONAL CIRCUITRY IN HUMAN CELLS AND METHODS OF USE THEREOF

RELATED APPLICATIONS

This application claims the benefit of U.S. Provisional Application No. 62/387,469, filed Dec. 23, 2015; and is also a continuation-in-part of U.S. patent application Ser. No. 14/663,056, filed Mar. 19, 2015, which claims the benefit of U.S. Provisional Application No. 61/955,764, filed Mar. 19, 2014; the entire teachings of these applications are incorporated herein by reference.

GOVERNMENT SUPPORT

This invention was made with government support under ROI-HG002668 awarded by the National institutes of Health: The government has certain rights in the mention

BACKGROUND OF THE INVENTION

The molecular pathways for cellular processes such as metabolism, energy production, and signal transduction have been described in some detail. In contrast, the transcriptional circuitries that control the gene expression programs that define cell identity have yet to be mapped in most cells. For such mapping, it is essential to identify the set of key transcription factors that are responsible for control of cell identity and to determine how they function together to regulate cell-type-specific gene expression programs.

SUMMARY OF THE INVENTION

In some aspects, the disclosure provides a method of identifying the core regulatory circuitry of a cell, tissue or cell line (e.g., a diseased cell, diseased tissue or diseased cell line), comprising: a) identifying a group of transcription factor encoding genes in a cell or tissue which are associated with a super-enhancer; b) determining which transcription factor encoding genes identified in a) comprise autoregulated transcription factor encoding genes, wherein a transcription factor encoding gene identified in a) comprises an autoregulated transcription factor encoding gene if the transcription factor encoded by the transcription factor encoding gene is predicted to bind to the super-enhancer associated with the transcription factor encoding gene and c) identifying the core regulatory circuitry of the cell or tissue, wherein the core regulatory circuitry of the cell or tissue comprises autoregulated transcription factor encoding genes identified in b) which form an interconnected autoregulatory loop, wherein the autoregulated transcription factor encoding genes identified in b) form an interconnected autoregulatory loop if each transcription factor encoded by an autoregulated transcription factor encoding gene identified in b) is predicted to bind to the super-enhancer associated with each of the other autoregulated transcription factor encoding genes identified in b).

In some embodiments, the core regulatory circuitry comprises the autoregulated transcription factors forming the interconnected autoregulatory loop, the transcription factors encoded by the autoregulated transcription factor encoding genes, a super-enhancers associated with the autoregulated transcription factor encoding genes, or a component of the super-enhancer (e.g., Mediator or Brd4).

In some embodiments, the method further includes d) determining at least one target of at least one transcription factor encoded by at least one autoregulated transcription factor encoding gene. In some embodiments, the at least one target of the at least one transcription factor encoded by the at least one autoregulated transcription factor encoding gene comprises a gene which encodes a reprogramming factor or a cell identity gene. In some embodiments, the transcription factor encoded by the transcription factor encoding gene is predicted to bind to the super-enhancer associated with transcription factor encoding gene if the super-enhancer associated with the transcription factor encoding gene comprises at least one DNA sequence motif predicted for the transcription factor encoded by the transcription factor encoding gene. In some embodiments, each transcription factor encoded by the autoregulated transcription factor encoding gene is predicted to bind to the super-enhancer associated with each of the other autoregulated transcription factor encoding genes if the super-enhancers associated with each of the other autoregulated transcription factor encoding genes comprise at least one DNA sequence motif predicted for each of the transcription factors encoded by each of the other autoregulated transcription factor encoding genes.

In some embodiments, the at least one DNA sequence motif is located between 500 bp upstream and 500 bp downstream of the super-enhancer associated with the transcription factor encoding gene.

In some embodiments, the cell is a diseased cell (e.g., a cancer cell). In some embodiments, the cell comprises a) a blood cell selected from the group consisting of a CD14+ monocyte, a CD56+ monocyte, a CD4+ T cell, a CD3+ T cell, a CD4+ primary T cell, a CD4+ memory T cell, a CD4+ naïve T cell, a CD4+ CD127+ T cell, a CD8+ primary T cell, a CD8+ memory T cell, a CD8+ naïve T cell, a CD19+ B cell, a CD20+ B cell, a CD34+ HSC cell; b) a brain cell selected from the group consisting of astrocytes, glial cells, an neurons; c) a fibroblast selected from the group consisting of dermal fibroblast and fibroblast; d) skeletal myoblasts; e) a colon crypt, f) an embryonic stem cell; g) a hepatocyte; h) a tumor cell; i) a keratinocyte; j) a macrophage; k) lymphocytes; l) regulatory T (Tregs); in) NK cells; n) pancreatic beta cells; o) cardiac muscle cells; p) never cells; and q) chondrocytes.

In some embodiments, the tissue is a diseased tissue (e.g., cancer tissue). In some embodiments, the tissue comprises a) brain tissue selected from the group consisting of brain hippocampus, brain inferior temporal lobe, brain angular gyrus, and brain mid frontal lobe; b) internal tissue selected from the group consisting of spleen, bladder, mammary epithelium, adipose, ovarian, adrenal gland, pancreatic, and lung; d) thymus; e) muscle tissue selected from the group consisting of skeletal muscle, psoas muscle, duodenum smooth muscle, and stomach smooth muscle; f) heart tissue selected from the group consisting of right ventricle, aorta, left ventricle, and right atrium; g) digestive tissue selected from the group consisting of esophagus, gastric, sigmoid colon, and small intestine; and h) tumor tissue.

In some embodiments, the cell comprises a blood cell. In certain aspects, the cell comprises a blood cell selected from the group consisting of a CD4+ CD45RA+ naïve T cell, a CD4+ CD25− IL17− helper T cell, a CD4+ CD25− IL17+ helper T cell and a CD8+ CD45RA+ naïve T cell.

In some embodiments, the tissue comprises fetal tissue. In some embodiments, the tissue comprises fetal tissue selected from the group consisting of fetal small intestine tissue, fetal large intestine tissue, fetal muscle tissue, fetal thymus tissue and fetal lung tissue.

In some embodiments, the cells or cell line comprises cancer cells. For example, in certain aspects, the cancer is selected from the group consisting of T cell leukemia, lymphoblastoid, chronic myelogenous leukemia, multiple myeloma and glioblastoma. In other embodiments, the cancer cell line is a lung cancer cell line, a breast cancer cell line, a colorectal cancer cell line, a cervical cancer cell line, a prostate cancer cell line, a liver cancer cell line, a pancreatic cancer cell line, a brain cancer cell line, a blood cancer cell line and a colorectal cancer cell line.

In some aspects, the core regulatory circuitry comprises a component of the super-enhancer, and wherein the component of the super-enhancer comprises Mediator. In some aspects, the core regulatory circuitry comprises a component of the super-enhancer, and wherein the component of the super-enhancer comprises Brd4.

In some aspects, the disclosure provides a method of identifying the cell identity program of a diseased cell, diseased tissue or diseased cell line (e.g., a cancer cell or tissue), comprising a) identifying the core regulatory circuitry of a cell or tissue of interest, wherein the core regulatory circuitry of the cell or tissue of interest comprises at least one autoregulated transcription factor encoding gene associated with a super-enhancer in the cell or tissue of interest, at least one transcription factor encoded by the at least one autoregulated transcription factor encoding gene, at least one super-enhancer associated with the at least one autoregulated transcription factor encoding gene, and optionally at least one component of the super-enhancer; and b) identifying the cell identity program of the cell or tissue, wherein the cell identity program of the cell or tissue comprises the core regulatory circuitry identified in a) and at least one target of the at least one transcription factor encoded by the at least one autoregulated transcription factor encoding gene in the core regulatory circuitry.

In some embodiments, the at least one target comprises a gene comprising at least one enhancer element predicted to be bound by the at least one transcription factor. In some embodiments, the at least one enhancer element predicted to be bound by the at least one transcription factor comprises a DNA sequence motif associated with a super-enhancer.

In some aspects, the disclosure provides a method of modulating the identity of a cell, comprising modulating at least one component of a cell identity program of the cell. In some embodiments, the at least one component of the cell identity program in the cell comprises the core regulatory circuitry of the cell or at least one target modulated by the at least one component of the core regulatory circuitry of the cell. In some embodiments, the modulating the at least one component of the cell identity program in the cell comprises contacting the cell with an agent that modulates at least one component of the cell identity program of the cell.

In some embodiments, the cell comprises a cell listed in Table 1. In some aspects, the at least one component of the cell identity program comprises at least one component selected from the group consisting of (i) at least one gene encoding a master transcription factor, (ii) the master transcription factor encoded by the at least one gene, (iii) a target of the master transcription factor, and (iv) at least one super-enhancer associated with any of (i)-(iii), or at least one component of the super-enhancer.

In some embodiments, the method further includes (i) modulating at least two components of the cell identity program in the cell (e.g., a diseased cell), (ii) modulating at least three components of the cell identity program in the cell, (iii) modulating at least four components of the cell identity program in the cell, or (iv) modulating at least five components of the cell identity program in the cell. In some embodiments, the method further includes (i) modulating at least one component of the core regulatory circuitry in the cell and at least one target of a master transcription factor in the core regulatory circuitry; (ii) modulating at least two components of the core regulatory circuitry in the cell and at least two targets of a master transcription factor in the core regulatory circuitry; (iii) modulating at least three components of the core regulatory circuitry in the cell and at least three targets of a master transcription factor in the core regulatory circuitry; (iv) modulating at least four components of the core regulatory circuitry in the cell and at least four targets of a master transcription factor in the core regulatory circuitry; and (v) modulating at least five components of the core regulatory circuitry in the cell and at least five targets of a master transcription factor in the core regulatory circuitry of the cell.

In some aspects, the disclosure provides a method of diagnosing a cell identity program-related disorder comprising determining whether the cell identity program of the cell or tissue is enriched for disease-associated variations. In some embodiments, the determining comprises: a) obtaining a sample comprising a cell or tissue of interest; and b) detecting the presence of disease-associated variations in components of the cell identity program of the cell or tissue of interest, wherein the cell identity program of the cell or tissue is enriched for disease-associated variations if at least two disease-associated variations are detected in the components of the cell identity program of the cell or tissue of interest.

In some embodiments, the cell identity program of the cell or tissue is enriched for disease-associated variations if (i) at least three; (ii) at least four; (iii) at least five; or (iv) at least six disease associated variations are detected in the components of the cell identity program of the cell or tissue of interest. In some embodiments, the disease-associated variations comprise GWAS variants. In some embodiments, the disease-associated variations comprise GWAS variants in a super-enhancer associated with the core regulatory circuitry in the cell or tissue of interested selected from the group consisting of i) at least one gene encoding a master transcription factor, (ii) the master transcription factor encoded by the at least one gene, or (iii) at least one target of the master transcription factor. In some embodiments, the GWAS variant is selected from the group consisting of (i) a GWAS variant from Alzheimer disease present in the cell identity program of brain hippocampus; (ii) a GWAS variant from systemic lupus erythematosus present in the cell identity program of CD20 cells; (iii) a GWAS variant from fasting insulin trait present in the cell identity program of adipose nuclei; (iv) a GWAS variant from ulcerative colitis present in the cell identity program of sigmoid colon; and (vi) a GWAS variant from electrocardiographic traits present in the cell identity program of left ventricle.

In some aspects, the disclosure provides a method of treating a cell identity program-related disorder in a subject in need thereof, comprising modulating at least one abnormal component of a cell identity program in a diseased cell or tissue of the subject.

In some embodiments, modulating at least one abnormal component of the cell identity program in the diseased cell or tissue of the subject comprises administering to the subject an effective amount of an agent that modulates the at least one abnormal component of the cell identity program. In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics;

nucleic acids selected from the group consisting of siRNAs, shRNAs, antisense RNAs, ribozymes, and aptamers, an extract made from biological materials selected from the group consisting of bacteria, plants, fungi, animal cells, and animal tissues; naturally occurring or synthetic compositions; and any combination thereof. In some embodiments, the diseased cell or tissue comprises a tumor cell or tissue. In some embodiments, the diseased cell or tissue comprises a cell or tissue listed in Table 1, and the abnormal component comprises at least one component of the cell identity program of the cell selected from the group consisting of (i) a gene encoding a master transcription factor, (ii) the master transcription factor encoded by the gene, (iii) a target of the master transcription factor, and (iv) a super-enhancer associated with any of (i)-(iii), or a component of the super-enhancer.

In some embodiments, the method further includes diagnosing the subject as having the cell identity program-related disorder.

In some aspects, the disclosure provides a method of reprogramming a cell of a first cell type to a cell of a second cell type, the method comprising modulating at least one component of the core regulatory circuitry of the second cell type in the cell of the first cell type.

In some embodiments, (i) the at least one component comprises a transcriptional repressor or transcriptional co-repressor and modulating comprises repressing the at least one component; and/or (ii) the at least one component comprises a transcriptional activator or transcriptional co-activator and modulating comprises activating the at least one component. In some embodiments, activating the at least one component comprises (i) expressing the at least one component of the core regulatory circuitry of the second cell type in the cell of the first type; (ii) introducing the at least one component of the core regulatory circuitry of the second cell type into the cell of the second type; (iii) contacting the cell with an agent that activates expression of the at least one component of the core regulatory circuitry of the second cell type in the cell of the first type; and (iv) any combination of (i)-(iii). In some embodiments, modulating (e.g., activating) the at least one component of the core regulatory circuitry of the second cell type in the cell of the first type occurs ex vivo. In some embodiments, modulating (e.g., repressing) the at least one component of the core regulatory circuitry of the second cell type in the cell of the first type occurs ex vivo.

In some embodiments, modulating (e.g., activating) the at least one component of the core regulatory circuitry of the second cell type in the cell of the first type occurs in vivo. In some embodiments, modulating (e.g., repressing) the at least one component of the core regulatory circuitry of the second cell type in the cell of the first type occurs in vivo.

In some embodiments, the method includes inhibiting at least one component of the core regulatory circuitry of the first cell type. In some embodiments, the (i) cell of the first cell type comprises the core regulatory circuitry of a diseased cell, and the cell of the second cell type comprises the core regulatory circuitry of a normal cell; (ii) cell of the first cell type comprises the core regulatory circuitry of a terminally differentiated cell, and the cell of the second cell type comprises the core regulatory circuitry of a less differentiated cell; (iii) cell of the first cell type comprises the core regulatory circuitry of a first somatic cell type, and the cell of the second cell type comprises the core regulatory circuitry of a second somatic cell type; (iv) cell of the first cell type comprises the core regulatory circuitry of a somatic cell, and the cell of the second cell type comprises the core regulatory circuitry of an embryonic cell; (v) cell of the first cell type comprises the core regulatory circuitry of a first tissue type, and the cell of the second type comprises the core regulatory circuitry of a second tissue type; (vi) cell of the first cell type comprises the core regulatory circuitry of a skin or fat cell, and the cell of the second cell type comprises the core regulatory circuitry of a tissue; and (vii) cell of the first cell type comprises the core regulatory circuitry of a tumor cell or tissue, and the cell of the second cell type comprises the core regulatory circuitry of a healthy cell or tissue.

In some aspects, the disclosure provides a method of identifying a candidate modulator of at least one component of the core regulatory circuitry of a cell or tissue (e.g., a diseased cell or tissue), comprising: a) contacting a cell or tissue with a test agent; and b) assessing the ability of the test agent to modulate at least one component of the core regulatory circuitry of the cell or tissue, wherein the test agent is identified as a candidate modulator of the at least one component of the core regulatory circuitry of the cell or tissue if the at least one component of the core regulatory circuitry is activated or inhibited in the presence of the test agent.

In some embodiments, the at least one component of the core regulatory circuitry of the cell or tissue comprises a reprogramming factor or a cell identity gene. In some embodiments, the at least one component of the core regulatory circuitry of the cell or tissue comprises a disease-associated variant.

In some aspects, the disclosure provides a method of reprogramming a cell (e.g., a diseased cell) comprising contacting the cell with the candidate modulator identified according to a method described herein. In some embodiments, at least one component of the core regulatory circuitry of the cell comprises a disease-associated variant. In some embodiments, contacting occurs in vivo or ex vivo.

In some aspects, the disclosure provides a method of identifying a candidate modulator of at least one component of the cell identity program of a cell or tissue, comprising: a) contacting a cell or tissue with a test agent; and b) assessing the ability of the test agent to modulate at least one component of the cell identity program of the cell or tissue, wherein the test agent is identified as a candidate modulator of the at least one component of the cell identity program of the cell or tissue if the at least one component of the cell identity program of the cell or tissue is activated or inhibited in the presence of the test agent.

In some embodiments, the at least one component of the cell identity program of the cell or tissue comprises a reprogramming factor or a cell identity gene. In some embodiments, the at least one component of the cell identity program of the cell or tissue comprises a disease-associated variant.

In some aspects, the disclosure provides a method of reprogramming a cell comprising contacting the cell with the candidate modulator identified according to a method described herein. In some embodiments, at least one component of the core regulatory circuitry of the cell comprises a disease-associated variant. In some embodiments, contacting occurs in vivo or ex vivo.

In some aspects, the disclosure provides a method of identifying a target for drug discovery comprising identifying a variation in at least one component of the core regulatory circuitry of a cell or tissue that is more prevalent in subjects suffering from a disease than in healthy subjects, wherein the at least one component of the core regulatory circuitry of the cell or tissue that is more prevalent in subjects suffering from a disease than in healthy subjects comprises a disease-associated variant, and wherein the disease-associated variant is a target for drug discovery.

In some aspects, the disclosure provides a method of identifying a target for drug discovery comprising identifying a variation in at least one component of the cell identity program of a cell or tissue that is more prevalent in subjects suffering from a disease than in healthy subjects, wherein the at least one component of the cell identity program of the cell or tissue that is more prevalent in subjects suffering from a disease than in healthy subjects comprises a disease-associated variant, and wherein the disease-associated variant is a target for drug discovery.

In some embodiments, the target for drug discovery comprises a target for diagnostic purposes.

In some aspects, the disclosure provides a method of identifying a target for anti-cancer drug discovery comprising: a) comparing the core regulatory circuitry of a tumor cell or tissue with the core regulatory circuitry of a corresponding non-tumor cell or tissue; and b) identifying at least one component that differs between the core regulatory circuitry of the tumor cell or tissue and the corresponding non-tumor cell or tissue, wherein the at least one component that differs between the core regulatory circuitry of the tumor cell or tissue and the corresponding non-tumor cell or tissue is identified as a target for anti-cancer drug discovery.

In some embodiments, a gene regulated by the at least one component is identified as a target for anti-cancer drug discovery. In some embodiments, the at least one component differs in sequence, expression, and/or activity.

In some aspects, the disclosure provides a method of identifying an anti-cancer agent comprising identifying a modulator of the target for anti-cancer drug discovery identified according to a method described herein.

In some aspects, the disclosure provides a method treating a cancer characterized by tumor cell or tissue comprising the target for anti-cancer drug discovery, comprising administering to a subject suffering from the cancer an effective amount of the anti-cancer agent identified according to a method described herein.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology. McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm:nih.gov/omim/ and in Online Mendelian Inheritance in Animals (OMIA), a database of genes, inherited disorders and traits in animal species (other than human and mouse), at http://omia.angis.org.au/contact-.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A is a graphical description of the method used to create CRC models and depicting (1) the identification of SE-assigned expressed TFs; (2) the identification of the TFs that are predicted to bind their own SE, considered as autoregulated; and (3) CRCs are assembled as fully inter-connected loops of autoregulated TFs. FIG. 1B illustrates (1) TF assigned SE constituents defined by H3K27ac ChIP-seq peak signals; (2) TFs having at least 3 DNA-binding sequence motif instances in their SE constituents are considered autoregulated; and (3) TFs with SEs having at least 3 DNA-binding sequence motif instances for each of the other predicted autoregulated TF together form an interconnected autoregulatory loop. FIG. 1C shows metagenes for the ChIP-seq signal for H3K27ac (left) and for the average ChIP-seq signal for POU5F1, SOX2 and NANOG (right) in H1 hESCs in the region +/−5 kb around the center of the SE constituents. FIG. 1D shows the average percentage of DNA-binding motifs that are actually bound by the TFs from ChIP-seq data for POU5E1, SOX2 and NANOG in H1 hESCs, in either SE constituents or sets of random genomic sequences of the same size. FIG. 1F shows a Venn diagram showing the average numbers, across 84 samples, of (1) TFs having motifs that are expressed (445 TFs), (2) TFs having motifs, that are expressed and assigned to a SE (61 TFs), (3) TFs having motifs, that are expressed and assigned to a SE and that are predicted to bind their own SE (39 TFs), and (4) TFs that are part of the CRC model (15 TFs).

FIG. 2A (left) depicts a CRC map for H1 human embryonic stem cells. The role of each TF in ESC pluripotency and self-renewal is listed in Table 9, below. FIG. 2A (right) depicts H1 hESC extended regulatory circuit. Examples of SE-assigned genes that are predicted to be bound by each of the TFs in the CRC. The role of these factors in ESC pluripotency and self-renewal is listed in Table 5, below. FIG. 2B shows ChIP-seq data for H3K27ac, POU5F1, SOX2 and NANOG showing binding of the TFs to each of the SEs of the SE-assigned TFs in the hESC CRC. SE genomic locations are depicted by red lines on top of the tracks. FIG. 2C presents pie-charts showing the percentages of SE-assigned genes (top row) or all expressed genes (bottom row) whose regulatory sequences are predicted to be bound by increasing numbers of hESC candidate core TFs. FIG. 2D is a diagram showing putative transcriptional regulation of MIR371 on SOX2 expression in hESCs.

FIG. 4A depicts core regulatory circuit containing GATA3, MYB, RUNX1 and TAL1 for T-ALL Jurkat cells. FIG. 4B presents ChIP-seq data for H3K27ac, MYB, RUNX1, TAL1 and GATA3 showing binding of the TF to each of the SE in T-ALL Jurkat cell core circuit. SE genomic locations arc depicted by red lines on top of the tracks. FIG. 4C shows boxplots showing fold change (FC) in expression for Jurkat cells transfected with the indicated shRNAs vs control shRNAs, for either the set of candidate core TFs displayed in FIG. 4A (red) or the full set of TFs considered expressed in Jurkat cells (blue). P-values quantifying the difference between the two sets were calculated using a Wilcoxon test.

FIG. 5A depicts percentages of TFs identified as candidate core TFs in a given number of cell or tissue types. The number of cell or tissue types in which a TF is identified as candidate core TFs is displayed with boxes on the right. A representative sample of each cell and tissue type is used when multiple samples from the same cell or tissue type are present in the dataset. FIG. 5B shows DNA-binding domains that are significantly differentially represented in the set of candidate core TFs and housekeeping TFs. FIG. 5C depicts transcript levels for the set of candidate core TFs and for the full set of TFs considered expressed in each sample. P-values quantifying the difference between the two sets were calculated using a Wilcoxon test.

FIG. 6A illustrates CRCs cluster according to cell type similarity. Hierarchical clustering of candidate core TFs for 80 human samples. The matrix of correlation based on Pearson coefficients identifies specific clusters for Hematopoietic Stem Cells (HSC), blood cancer cells, blood cells, epithelial normal and cancer cells, cardio-pulmonary system cells, upper gastro-intestinal system and brain cells. Correlation values range from −1 to 1 and are colored front blue to red according to the color scale. FIG. 6B illustrates a radar plot showing the enrichment of candidate core TFs, compared to non-core TFs, in GWAS list of genes for multiple disease or traits. P-values were calculated using a z-test and 1/p-value are plotted for the diseases or traits that showed an enrichment p-value<$5^{e-2}$ of candidate core TFs. FIG. 6C shows pie-charts showing the average percentages for all samples, of SE-assigned genes (top row) or of all expressed genes (bottom row), whose regulatory sequences are predicted to be co-occupied by more than half or by all the TF in the CRC.

FIGS. 8A-8C depicts the effects of H1hES candidate core TF depletion on pluripotency and proliferation. FIG. 8A shows the rank of each candidate core TF among all TFs for mean of z-score for OCT4-CiFP fluorescence reduction and nuclei number reduction from two experimental replicates, from siRNA screen data in H1 hES (Chia et al. 2010). FIG. 8B shows Gene-Set Enrichment Analysis (GSEA) for the candidate core TFs compared to all TFs for POU5F1/OCT4-GFP expression values. FIG. 8C shows GSEA analysis for the candidate core TFs compared to all TFs for nuclei number values.

DETAILED DESCRIPTION OF THE INVENTION

Figures 1A, 1B:
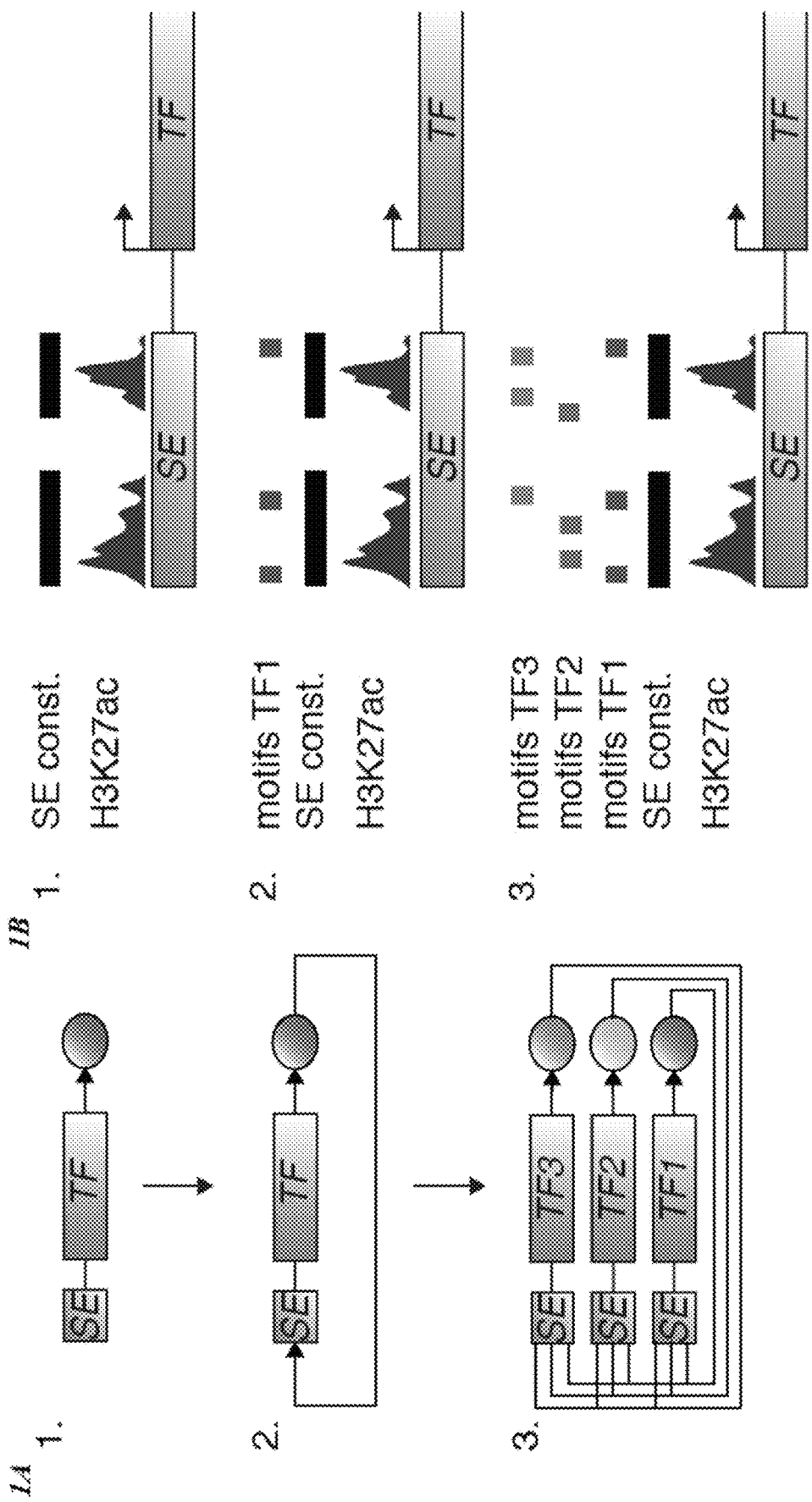
FIGS. 1A-1E depict a method to build Core Regulatory Circuitry (CRC).

Aspects of the disclosure relate to methods of identifying the core regulatory circuitry and/or cell identity programs of cells or tissues, and related diagnostic, treatment, and screening methods involving the core regulatory circuitry and/or cell identity programs identified.

In embryonic stem cells and a few other cell types, master transcription factors (TFs) have been shown to function together in a core regulatory circuit (CRC) that controls the gene expression programs that define cell identity (Boyer et al., 2005; Lee and Young, 2011; Odom et al., 2006; Lien et al., 2002; Novershtern et al., 2011). In these CRCs, the master TFs regulate their own genes and other genes key to cell identity though their binding of the super-enhancers associated with those genes (Whyte et al., 2013; Hnisz et al., 2013). Work described herein exploits navel features of super-enhancers and TF binding site sequences for 75 human cell and tissue types to construct models of CRCs for a broad spectrum of cell types throughout the human body. Cell Identity Program models for these cells and tissues, which consist of the master TFs forming the CRCs and their target genes, contain the vast majority of master TFs and reprogramming factors described for specific cell types in the literature and cluster according to known cell lineages. The work described herein also demonstrates that the master TFs in the CRCs have binding site sequences in the enhancers of the majority of cell identity genes that are expressed in each cell/tissue type. Surprisingly, the work described herein also demonstrates that the regulatory elements within the Cell Identity Program models are highly enriched in disease-associated sequence variation, and shows how tumor cells can modify the CRC to create gene expression programs associated with tumor pathology. These maps of core regulatory circuitry provide founding models to test and expand knowledge of regulatory circuitry, provide guidance for reprogramming studies, and should facilitate understanding of disease causality.

Accordingly, aspects of the disclosure relate to methods for identifying the core regulatory circuitry of a cell or tissue. In some aspects, a method of identifying the core regulatory circuitry of a cell or tissue comprises: a) identifying a group of transcription factor encoding genes in a cell or tissue which are associated with a super-enhancer; b) determining which transcription factor encoding genes identified in a) comprise autoregulated transcription factor encoding genes, wherein a transcription factor encoding gene identified in a) comprises an autoregulated transcription factor encoding gene if a transcription factor encoded by the transcription factor encoding gene is predicted to bind to a super-enhancer associated with the transcription factor encoding gene; and c) identifying the core regulatory circuitry of the cell or tissue, wherein the core regulatory circuitry of the cell or tissue comprises autoregulated transcription factor encoding genes identified in b) which form an interconnected autoregulatory loop, wherein the autoregulated transcription factor encoding genes identified in b) form an interconnected autoregulatory loop if each transcription factor encoded by an autoregulated transcription factor encoding gene identified in b) is predicted to bind to a super-enhancer associated with each of the other autoregulated transcription factor encoding genes identified in b). An exemplary embodiment of a method for identifying the core regulatory circuitry of a cell or tissue is depicted in FIG. 1A.

As is shown in the example embodiment depicted in FIG. 1A (step 1), master transcription factor candidates are identified in a cell or tissue by determining all of the transcription factors in the cell or tissue which are encoded by genes associated with a super-enhancer in the cell or tissue, e.g., the group of transcription factor encoding genes associated with a super-enhancer. As used herein, a "transcription factor encoding gene" refers to any gene which encodes a transcription factor. The transcription factor can be a known transcription factor, a putative transcription factor, etc . . . It should be appreciated that the group of transcription factor encoding genes is intended to encompass all genes in a particular cell or tissue which encode master transcription factors. The number of such transcription factor encoding genes may vary depending on the particular cell or tissue type. In some embodiments, the group of transcription factor encoding genes (e.g., genes encoding master transcription factors) is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 transcription factor encoding genes. In some embodiments, the group of transcription factor encoding genes comprises at least 5, at least 10, at least 15, at least 20, at least 25, at least 30, at least 35, at least 40, at least 45, or at least 50 transcription factor encoding genes. In some embodiments, the group of transcription factor encoding genes comprise at least 50, at least 60, at least 70, at least 80, at least 90, or at least 100 transcription factor encoding genes.

As is illustrated in FIG. 1A (step 2), the master transcription factor candidates identified in step 1 (e.g., as exemplified in FIG. 1A, step 1) can then be assessed in step 2 to determine whether the master transcription factor candidates are autoregulated transcription factors. As used herein, the phrase "autoregulated transcription factor" refers to a transcription factor encoded by an autoregulated transcription factor encoding gene, i.e., a super-enhancer associated with the transcription factor encoding gene is predicted to be bound by the transcription factor encoded by the transcription factor encoding gene. Put differently, as is shown in FIG. 1A (step 2), the transcription factor encoding gene (boxed TF) encodes a transcription factor (oval) that binds to the super-enhancer (boxed SE) associated with the transcription actor encoding gene. It is expected that only a fraction of the candidate master transcription factors in any particular cell or tissue will comprise autoregulated transcription factors. In some embodiments, at least 1%, at least 2%, at least 3%, at least 4%, at least 5%, at least 6%, at least 7%, at least 8%, at least 9%, or at least 10% of the candidate master transcription factors in a cell or tissue comprise autoregulated transcription factors. In some embodiments, at least 1%, at least 2%, at least 3%, at least 4%, at least 5%, at least 6%, at least 7%, at least 8%, at least 9%, or at least 10% of the super-enhancer associated transcription factor encoding genes in a cell or tissue comprise autoregulated transcription factor encoding genes.

As exemplified in the embodiment shown in FIG. 1A (step 3) of the method involves identifying a core regulatory circuitry of the cell or tissue by determining the largest set of fully interconnected autoregulated transcription factors or autoregulated transcription factor encoding genes identified in step 2 which forms an interconnected autoregulatory loop. As used herein, the phrases "autoregulated transcription factors forming an interconnected autoregulatory loop" and "master transcription factors" are used interchangeably herein to refer to transcription factors encoded by genes whose expression is driven by super-enhancers, and which bind their own super-enhancers (e.g., a super-enhancer or super-enhancer component associated with the gene encoding the transcription factor) as well as super-enhancers associated with other autoregulated transcription factor encoding genes and/or the transcription factors encoded by those genes in the interconnected autoregulatory loop.

Figure 2A:
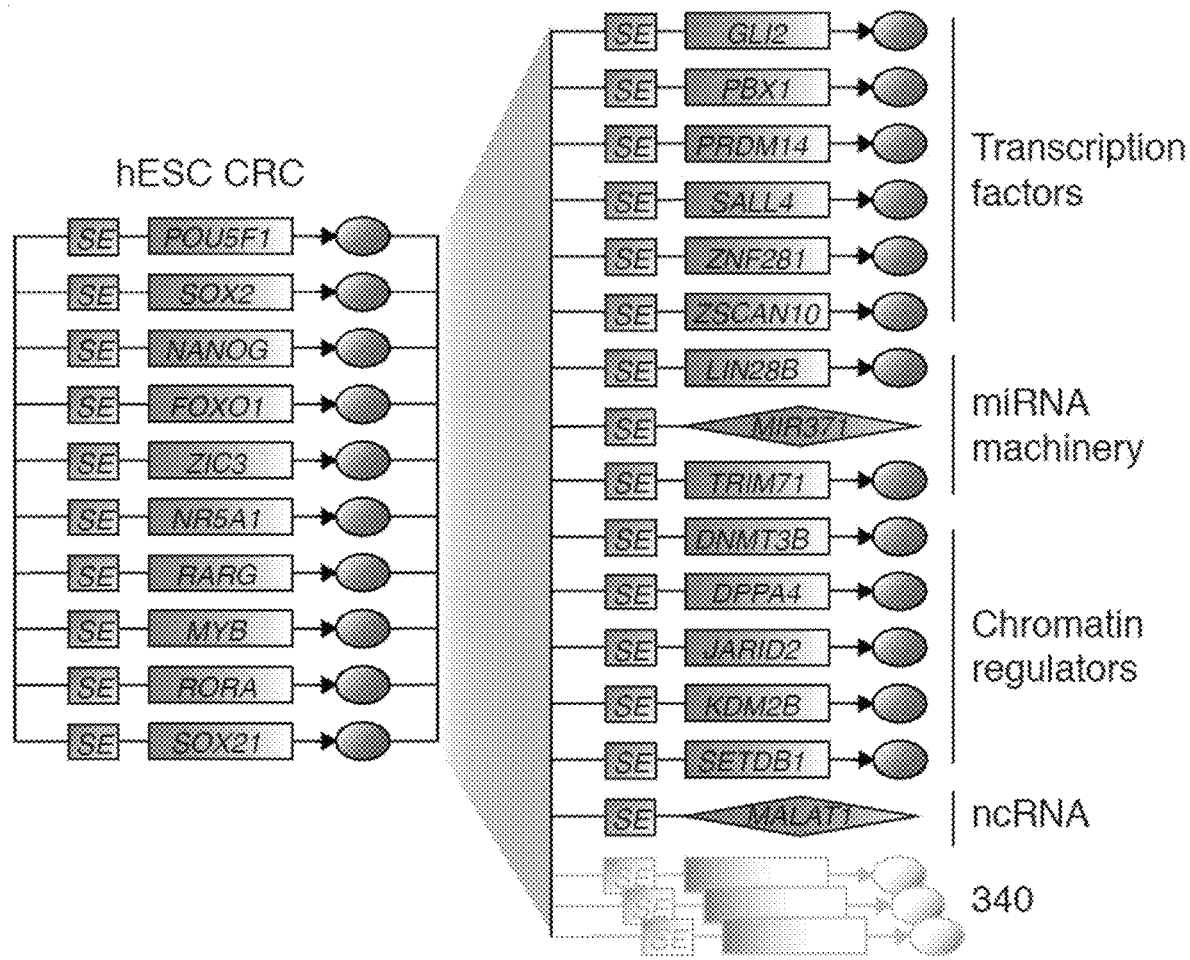
FIGS. 2A-2D depict H1 core and extended regulatory circuitry.

As used herein, the phrase "interconnected autoregulatory loop" refers to a network of autoregulated transcription factor encoding genes predicted to bind each of the super-enhancers associated with other autoregulated transcription factors in the network. The concept of an autoregulatory loop is depicted in FIG. 1A (step 3) for three hypothetical transcription factors TF1, TF2, TF3. As shown in FIG. 1A (step 3), the interconnected autoregulatory loop forms a core regulatory circuitry that includes each autoregulated transcription factor encoding gene (e.g., TF1, TF2, and TF3), the autoregulated transcription factor encoded by each autoregulated transcription factor encoding gene (e.g., oval 1, oval 2, and oval 3), the super-enhancers or a component of a super-enhancer associated with each autoregulated transcription factor encoding gene, wherein each autoregulated transcription factor in the network is predicted to hind to or binds to each super-enhancer in the network. To further illustrate the core regulatory circuitry concept, FIG. 2A depicts a model of the core regulatory circuitry in human embryonic stem cells (ESCs). In some embodiments, the core regulatory circuitry comprises the autoregulated transcription factors forming the interconnected autoregulatory loop, the transcription factors encoded by the autoregulated transcription factor encoding genes, a super-enhancers associated with the autoregulated transcription factor encoding genes, or a component of the super-enhancer. In some embodiments, a component of the core regulatory circuitry comprises a transcriptional activator, i.e., a component whose activation favors activation of the overall core regulatory circuitry of a cell or tissue. In some embodiments, a component of the core regulatory circuitry comprises a transcriptional repressor, i.e., a component whose repression favors activation of the overall core regulatory circuitry of a cell or tissue.

As used herein, the phrase "super-enhancer" refers to clusters of enhancers which drive the expression of genes encoding the master transcription factors and other genes key to cell identity. The disclosure contemplates the use of any super-enhancer. Exemplary super-enhancers are disclosed in PCT International Application No. PCT/US2013/066957 (Attorney Docket No. WIBR-137-WO1), filed Oct. 25, 2013, the entirety of which is incorporated by reference herein.

As used herein, the phrase "super-enhancer component" refers to a component, such as a protein, that has a higher local concentration, or exhibits a higher occupancy, at a super-enhancer, as opposed to a normal enhancer or an enhancer outside a super-enhancer, and in embodiments, contributes to increased expression of the associated gene. In an embodiment, the super-enhancer component is a nucleic acid (e.g., RNA, e.g., eRNA transcribed from the super-enhancer, i.e., an eRNA). In an embodiment, the nucleic acid is not chromosomal nucleic acid. In an embodiment, the component is involved in the activation or regulation of transcription. In some embodiments, the super-enhancer component comprises RNA polymerase II, Mediator, cohesin, Nipb1, p300, CBP, Chd7, Brd4, and components of the esBAF (Brg1) or a Lsd1-Hurd complex (e.g., RNA polymerase II). In some embodiments, the super-enhancer component comprises Mediator. In some embodiments, the super-enhancer component comprises Brd4.

As used herein, "enhancer" refers to a short region of DNA to which proteins (e.g., transcription factors) bind to enhance transcription of a gene. As used herein, "transcriptional coactivator" refers to a protein or complex of proteins that interacts with transcription factors to stimulate transcription of a gene. In some embodiments, the transcriptional coactivator is Mediator. In some embodiments, the transcriptional coactivator is Med1 (Gene ID: 5469). In some embodiments, the transcriptional coactivator is a Mediator component. As used herein, "Mediator component" comprises or consists of a polypeptide whose amino acid sequence is identical to the amino acid sequence of a naturally occurring Mediator complex polypeptide. The naturally occurring Mediator complex polypeptide can be, e.g., any of the approximately 30 polypeptides found in a Mediator complex that occurs in a cell or is purified from a cell (see, e.g., Conaway et al., 2005; Kornberg, 2005; Malik and Roeder, 2005). In some embodiments a naturally occurring Mediator component is any of Med1-Med 31 or any naturally occurring Mediator polypeptide known in the art. For example, a naturally occurring Mediator complex polypeptide can be Med6, Med7, Med10, Med12, MED14, Med15, Med17, Med21, Med24, Med27, Med28 or Med30. In some embodiments a Mediator polypeptide is a subunit found in a Med11, Med17, Med20, Med22, Med 8, Med 18, Med 19, Med 6, Med 30, Med 21, Med 4, Med 7, Med 31, Med 10, Med 1, Med 27, Med 26, Med14, Med15 complex. In some embodiments a Mediator polypeptide is a subunit found in a Med12/Med13/CDK8/cyclin complex. Mediator is described in further detail in PCT International Application No. WO 2011/100374, the teachings of which are incorporated herein by reference in their entirety.

In some embodiments, the method of identifying the core regulatory circuitry; comprises d) determining at least one target of at least one transcription factor encoded by at least one autoregulated transcription factor encoding gene. In some embodiments, the at least one target of the at least one transcription factor encoded by the at least one autoregulated transcription factor encoding gene comprises a gene which encodes a reprogramming factor or a cell identity gene.

Any suitable method can be used to determine whether the transcription factor encoded by the transcription factor encoding gene is predicted to bind to the super-enhancer associated with the transcription factor encoding gene, e.g., motif analysis or searching. In some embodiments, the transcription factor encoded by the transcription factor encoding gene is predicted to bind to the super-enhancer associated with transcription factor encoding gene if the super-enhancer associated with the transcription factor encoding gene comprises at least one DNA sequence motif predicted for the transcription factor encoded by the transcription factor encoding gene. In some embodiments, each transcription factor encoded by the autoregulated transcription factor encoding gene is predicted to bind to the super-enhancer associated with each of the other autoregulated transcription factor encoding genes if the super-enhancers associated with each of the other autoregulated transcription factor encoding genes comprise at least one DNA sequence motif predicted for each of the transcription factors encoded by each of the other autoregulated transcription factor encoding genes.

The at least one DNA sequence motif can be located within any range upstream or downstream of the super-enhancer associated with the transcription factor encoding gene (e.g., autoregulated transcription factor encoding gene). In some embodiments, the at least one DNA sequence motif is located between 10,000 bp upstream and 10,000 bp downstream of the super-enhancer associated with the transcription factor encoding gene. In some embodiments, the at least one DNA sequence motif is located between 5,000 bp upstream and 5,000 bp downstream of the super-enhancer associated with the transcription factor encoding gene. In some embodiments, the at least one DNA sequence motif is located between 500 bp upstream and 500 bp downstream of the super-enhancer associated with the transcription factor encoding gene. In some embodiments, the at least one DNA sequence motif is located between 50 bp upstream and 50 bp downstream of the super-enhancer associated with the transcription factor encoding gene.

In some embodiments, the methods described herein comprise obtaining ChIP-seq data for histone H3K27Ac, e.g., as a marker of an enhancer, e.g., a super-enhancer associated with a transcription factor encoding gene. In some embodiments, the H3K27Ac ChIP-seq data can be used to create a catalogue of super-enhancers for a cell or tissue of interest described herein.

Aspects of the disclosure involve cells or tissues of interest. The disclosure contemplates any cell or tissue of interest. In certain embodiments, such cells or tissues are diseased cells or tissues (e.g., cancer cells or tissues). In some embodiments, the cell comprises a cell of ectoderm lineage. In some embodiments, the cell comprises a cell of endoderm lineage. In some embodiments, the cell comprises a cell of mesoderm lineage. In some embodiments, the cell comprises an embryonic cell (e.g., embryonic stem cell). In some embodiments, the cell comprises a pluripotent cell (e.g., an induced pluripotent stem cell). In some embodiments, the cell comprises a somatic cell. In some embodiments, the cell comprises a multipotent cell. In some embodiments, the cell comprises a progenitor cell. In some embodiments, the cell or tissue comprises a cell or tissue listed in Table 1. In some embodiments, the cell comprises a) a blood cell selected from the group consisting of a CD14+ monocyte, a CD56+ monocyte, a CD4+ T cell, a CD3+ cell, a CD4+ primary T cell, a CD4+ memory T cell, a CD4+naïve T cell, a CD4+ CD127+ T cell, a CD8+ primary T cell, a CD8+ memory T cell, a CD8+ naïve T cell, a CD19+ B cell, a CD20+ B cell, a CD34+ HSC cell; b) a brain cell selected from the group consisting of astrocytes, glial cells, an neurons; c) a fibroblast selected from the group consisting of dermal fibroblast and fibroblast; d) skeletal myoblasts; e) a colon crypt, f) an embryonic stem cell; g) a hepatocyte; h) a tumor cell; i) a keratinocyte; j) a macrophage; k) lymphocytes; l) regulatory T (Tregs); m) NK cells; n) pancreatic beta cells; o) cardiac muscle cells; p) nerve cells; and q) chondrocytes (e.g., for cartilage repair). In certain aspects, the cell comprises a blood cell selected from the group consisting of a CD4+ CD45RA+ naïve T cell, a CD4+ CD25− IL17− helper T cell, a CD4+ CD25− IL 17+ helper T cell and a CD8+ CD45RA+ naïve T cell.

In some embodiments, the tissue comprises fetal tissue. In some embodiments, the tissue comprises fetal tissue selected from the group consisting of fetal small intestine tissue, fetal large intestine tissue, fetal muscle tissue, fetal thymus tissue and fetal lung tissue.

In some embodiments, the cells or cell line comprises cancer cells. For example, in certain aspects, the cancer is selected from the group consisting of T cell leukemia, lymphoblastoid, chronic myelogenous leukemia, multiple myeloma and glioblastoma. In other embodiments, the cancer cell line is a lung cancer cell line, a breast cancer cell line, a colorectal cancer cell line, a cervical cancer cell line, a prostate cancer cell line, a liver cancer cell line, a pancreatic cancer cell line, a brain cancer cell line, a blood cancer cell line and a colorectal cancer cell line.

In some embodiments, the cell comprises a diseased cell. In some embodiments, the cell comprises a cancer cell. In some embodiments, the cell comprises a cell that harbors a disease-associated variant (e.g., a GWAS variant). In some embodiments, the tumor cell is a cell from a cancer selected from the group consisting of ovarian cancer, bladder cancer, lung cancer, cervical cancer, breast cancer, prostate cancer, gliomas, fibrosarcomas, retinoblastomas, melanomas, soft tissue sarcomas, osteosarcomas, leukemias, stomach cancer, colon cancer, carcinoma of the kidney, gastrointestinal cancer, salivary gland cancer, pancreatic cancer, Hodgkin's disease, non-Hodgkin's lymphomas, acute and chronic lymphocytic leukemias, multiple myeloma, neuroblastoma, Wilms' tumor, testicular cancer, soft-tissue sarcomas, chronic lymphocytic leukemia, primary macroglobutinemia, chronic granulocytic leukemia, primary brain carcinoma, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas.

Aspects of the disclosure involve tissues of interest. The disclosure contemplates any tissue of interest. In some embodiments, the tissue comprises tissue of mesoderm lineage. In some embodiments, the tissue comprises tissue of endoderm lineage. In some embodiments, the tissue comprises tissue of ectoderm lineage. In some embodiments, the tissue comprises germ tissue. In some embodiments, the tissue comprises a) brain tissue selected from the group consisting of brain hippocampus, brain inferior temporal lobe, brain angular gyms, and brain mid frontal lobe; b) internal tissue selected from the group consisting of spleen, bladder, mammary epithelium, adipose, ovarian, adrenal gland, pancreatic, and lung; d) thymus; e) muscle tissue selected from the group consisting of skeletal muscle, psoas muscle, duodenum smooth muscle, and stomach smooth muscle; f) heart tissue selected from the group consisting of right ventricle, aorta, left ventricle, and right atrium; g) digestive tissue selected from the group consisting of esophagus, gastric, sigmoid colon, and small intestine; and h) tumor tissue.

In an embodiment the sample includes a cell or tissue, e.g., a cell or tissue from any of human cells; fetal cells; embryonic stem cells or embryonic stem cell-like cells, e.g., cells from the umbilical vein, e.g., endothelial cells from the umbilical vein; muscle, e.g., myotube, fetal muscle; blood cells, e.g., cancerous blood cells, fetal blood cells, monocytes; B cells, e.g., Pro-B cells; brain, e.g., astrocyte cells, angular gyrus of the brain, anterior caudate of the brain, cingulate gyrus of the brain, hippocampus of the brain, inferior temporal lobe of the brain, middle frontal lobe of the brain, brain cancer cells; T cells, e.g., naïve T cells, memory T cells; CD4 positive cells; CD25 positive cells; CD45RA positive cells; CD45RO positive cells; IL-17 positive cells; cells stimulated with PMA; Th cells; Th17 cells; CD255 positive cells; CD127 positive cells; CD8 positive cells; CD34 positive cells; duodenum, e.g., smooth muscle tissue of the duodenum, skeletal muscle tissue; myoblast; stomach, e.g., smooth muscle tissue of the stomach, e.g., gastric cells; CD3 positive cells; CD14 positive cells; CD19 positive cells; CD20 positive cells; CD34 positive cells; CD56 positive cells; prostate, e.g., prostate cancer; colon, e.g., colorectal cancer cells; crypt cells, e.g., colon crypt cells; intestine, e.g., large intestine; e.g., fetal intestine; bone, e.g., osteoblast; pancreas, e.g., pancreatic cancer; adipose tissue; adrenal gland; bladder; esophagus; heart, e.g., left ventricle, right: ventricle, left atrium, right atrium, aorta; lung, e.g., lung cancer cells; skin, e.g., fibroblast cells; ovary; psoas muscle; sigmoid colon; small intestine; spleen; thymus, e.g., fetal thymus; breast, e.g., breast cancer; cervix, e.g., cervical cancer; mammary epithelium; liver, e.g., liver cancer.

In some embodiments, the tumor tissue is tumor tissue from a cancer selected from the group consisting of ovarian cancer, bladder cancer, lung cancer, cervical cancer, breast cancer, prostate cancer, gliomas, fibrosarcomas, retinoblastomas, melanomas, soft tissue sarcomas, osteosarcomas, leukemias, stomach cancer, colon cancer, carcinoma of the kidney, gastrointestinal cancer, salivary gland cancer, pancreatic cancer, Hodgkin's disease, non-Hodgkin's lymphomas, acute and chronic lymphocytic leukemias, multiple myeloma, neuroblastoma, Wilms' tumor, testicular cancer, soft-tissue sarcomas, chronic lymphocytic leukemia, primary macroglobulinemia, chronic granulocytic leukemia, primary brain carcinoma, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas.

In some embodiments, the cell or tissue of interest comprises a cell or tissue that is affected by a disease. Exemplary diseases include, without limitation, an autoimmune disease, a metabolic disease, a cardiovascular disease, a neurological disease, a psychiatric disease, a renal disease, a liver disease, a dermatological disease, a pancreatic disease, a glandular disease, a lymph disease, an ophthalmological disease, an orthopedic disease, an inflammatory disease, a hematological disease, an infectious disease, a cell-type specific disease, an olfactory disease, etc. In some embodiments, the cell or tissue affected by a disease is obtained from a subject suffering from the disease.

Aspects of the disclosed methods include obtaining a biological sample from a subject comprising a cell or tissue of interest. A biological sample used in the methods described herein will typically comprise or be derived from cells or tissues isolated from a subject. The cells or tissues may comprise cells or tissues affected by a disease described herein. In some embodiments, the cells or tissues are isolated from a tumor cell or tissue described herein.

Samples can be, e.g., surgical samples, tissue biopsy samples, fine needle aspiration biopsy samples, core needle samples. The sample may be obtained using methods known in the art. A sample can be subjected to one or more processing steps. In some embodiments the sample is frozen and/or fixed. In some embodiments the sample is sectioned and/or embedded, e.g., in paraffin. In some embodiments, tumor cells, e.g., epithelial tumor cells, are separated from at least some surrounding stromal tissue (e.g., stromal cells and/or extracellular matrix). Cells or tissue of interest can be isolated using, e.g., tissue microdissection, e.g., laser capture microdissection. It should be appreciated that a sample can be a sample isolated from any of the subjects described herein.

In some embodiments, cells of the sample are lysed. Nucleic acids or polypeptides may be isolated from the samples (e.g., cells or tissues of interest). In some embodiments DNA, optionally isolated from a sample, is amplified. A wide variety of methods are available for detection of DNA, e.g., DNA of super-enhancers associated with autoregulated transcription factor encoding genes, DNA of an autoregulated transcription factor encoding gene, a DNA sequence motif etc. In some embodiments RNA, optionally isolated from a sample, is reverse transcribed and/or amplified. A wide variety of solution phase or solid phase methods are available for detection of RNA, e.g., mRNA encoding a master transcription factor or autoregulated transcription factor, mRNA encoding a target of a master transcription factor. Suitable methods include e.g., hybridization-based approaches (e.g., nuclease protection assays, Northern blots, microarrays, in situ hybridization), amplification-based approaches (e.g., reverse transcription polymerase chain reaction (which can be a real-time PCR reaction), or sequencing (e.g., RNA-Seq, which uses high throughput sequencing techniques to quantify RNA transcripts (see, e.g., Wang, Z., et al. Nature Reviews Genetics 10, 57-63, 2009)). In some embodiments of interest a quantitative PCR (qPCR) assay is used. Other methods include electrochemical detection, bioluminescence-based methods, fluorescence-correlation spectroscopy, etc.

Aspects of the methods described herein involve detecting the levels or presence of expression products, e.g., an expression product of a component the core regulatory circuitry comprising a disease associated variation (e.g., such as a single nucleotide polymorphism), an autoregulated transcription factor, an expression product of a target gene of a master transcription factor, etc.). Levels of expression products, e.g., of master transcription factor target genes, may be assessed using any suitable method. Either mRNA or protein level may be measured. A "polypeptide", "peptide" or "protein" refers to a molecule comprising at least two covalently attached amino acids. A polypeptide can be made up of naturally occurring amino acids and peptide bonds and/or synthetic peptidomimetic residues and/or bonds. Polypeptides described herein include naturally purified products, products of chemical synthetic procedures, and products produced by recombinant techniques from a prokaryotic or eukaryotic host, including, for example, bacterial, yeast, higher plant, insect and mammalian cells.

Exemplary methods for measuring mRNA include hybridization based assays, polymerase chain reaction assay, sequencing, in situ hybridization, etc. Exemplary methods for measuring protein levels include ELISA assays, Western blot, mass spectrometry, or immunohistochemistry. It will be understood that suitable controls and normalization procedures can be used to accurately quantify expression. Values can also be normalized to account for the fact that different samples may contain different proportions of a cell type of interest, e.g., tumor cells or tissues compared to corresponding non-tumor cells or tissues (e.g., health cells or tissues).

Aspects of the disclosure relate to methods of identifying the cell identity program of a cell or tissue. Generally, the methods of identifying the cell identity program of a cell or tissue incorporate the methods of identifying the core regulatory circuitry and extend those methods according to exemplary embodiments described herein. FIGS. 3A-3D are schematics illustrating a cell identity program map of human circuits for brain (hippocampus middle), adipocytes (adipose nuclei), heart (left ventricle) and pancreas, respectively.

In some aspects, a method of identifying the cell identity program of a cell or tissue, comprising a) identifying the core regulatory circuitry of a cell or tissue of interest, wherein the core regulatory circuitry of the cell or tissue of interest comprises at least one autoregulated transcription factor encoding gene associated with a super-enhancer in the cell or tissue of interest, at least one transcription factor encoded by the at least one autoregulated transcription factor encoding gene, at least one super-enhancer associated with the at least one autoregulated transcription factor encoding gene, and optionally at least one component of the super-enhancer and b) identifying the cell identity program of the cell or tissue, wherein the cell identity program of the cell or tissue comprises the core regulatory circuitry identified in a) and at least one target of the at least one transcription factor encoded by the at least one autoregulated transcription factor encoding gene in the core regulatory circuitry.

As used herein, the phrase "cell identity program" refers to the core regulatory circuitry of a cell or tissue and targets of master transcription factors that are part of the core regulatory circuitry of the cell or tissue, as is depicted in FIG. 2A, which shows an exemplary a cell identity program of human embryonic stem cells.

The disclosure contemplates the use of any target of a master transcription factor that is part of the core regulatory circuitry of a cell or tissue, e.g., at least one target which comprises a gene comprising at least one enhancer element predicted to be bound by the at least one transcription factor. In some embodiments, the at least one enhancer element predicted to be bound by the at least one transcription factor comprises a DNA sequence motif associated with a super-enhancer.

Surprisingly, and unexpectedly, the work described herein demonstrates the cell identity programs constructed for 75 different human cell and tissue types. Exemplary cell identity programs for 75 different human cell and tissue types are shown in Table 1.

Aspects of the disclosure relate to methods for modulating cell identity. Generally, the methods of modulating cell identity disclosed herein involve modulating at least one component of a cell identity program of a cell. The at least one component of the cell identity program in the cell comprises the core regulatory circuitry of the cell or at least one target modulated by the at least one component of the core regulatory circuitry of the cell. The disclosure contemplates the use of any suitable method for modulating the at least one component of a cell identity program of a cell. In some embodiments, modulating the at least one component of the cell identity program in the cell comprises contacting the cell with an agent that modulates at least one component of the cell identity program of the cell. The expressions "activate", "inhibit", "modulate", "increase", "decrease" or the like, e.g., which denote quantitative differences between two states, refer to at least statistically significant differences between the two states. For example, "modulating at least one component of the cell identity program" means that the sequence, expression, or activity of the at least one component of the cell identity program is modified, activated, increased, inhibited, or decreased in the presence of the agent by at least statistically significantly amount compared to the sequence, expression, or activity of the at least one component of the cell identity program in the absence of the agent. Such terms are applied herein to, for example, rates of cell proliferation, percentages of surviving cells, percentages of altered or modified sequences, levels of expression, levels of transcriptional or translational activity, and levels of enzymatic or protein activity, percentages of conversion of a cell of a first cell type to a cell of a second cell type, etc. It should be appreciated that the at least one component can comprise any component of the cell identity program including one or more components of the core regulatory circuitry or targets of autoregulated transcription factors expressed by the core regulatory circuitry. In some embodiments, the cell comprises a cell listed in Table 1 and the at least one component of the cell identity program comprises at least one component selected from the group consisting of (i) at. least one gene encoding a master transcription factor, (ii) the master transcription factor encoded by the at least one gene, (iii) a target of the master transcription factor, (iv) at least one super-enhancer associated with any of (i)-(iii) or at least one component of the super-enhancer.

The methods for modulating cell identity contemplate modulating any or all components of the cell identity program of a particular cell or tissue. Generally, it is expected that the extent of modulation of any particular cell or tissue from a first type to a second type is proportionate to the number of components in the cell identity program modulated relative to the total number of components in the cell identity program. In some embodiments, the method comprises modulating at least two components, at least three components, at least four components, or at least five components, of the cell identity program in the cell. In some embodiments, the method comprises modulating at least 5%, at least 10%, at least 15%, at least 20%, at least 25%, at least 33%, at least 40%, or at least 50% of the components in the cell identity program. In some embodiments, the method comprises modulating at least 55%, at least 60%, at least 70%, at least 75%, at least 80%, or at least 90% of the components in the cell identity program of a cell. In some embodiments, the method comprises modulating 90%, 91%, 92%, 93%, 94%, 95%, 96%, 97%, 98%, 99%, or up to 100% of the components of the cell identity program of the cell.

In some embodiments, the method comprises modulating at least one component of the core regulatory circuitry in the cell, and at least one target of a master transcription factor in the core regulatory circuitry. In some embodiments, the method comprises modulating at least two components of the core regulatory circuitry in the cell and at least two targets of a master transcription factor in the core regulatory circuitry. In some embodiments, the method comprises modulating at least three components of the core regulatory circuitry in the cell and at least three targets of a master transcription factor in the core regulatory circuitry. In some embodiments, the method comprises modulating at least four components of the core regulatory circuitry in the cell and at least four targets of a master transcription factor in the core regulatory circuitry. In some embodiments, the method comprises modulating at least five components of the core regulatory circuitry in the cell and at least five targets of a master transcription factor in the core regulatory circuitry of the cell. In some embodiments, the method comprises modulating at least 6, at least 7, at least 8, at least 9, at least 10, at least 15, at least 20 or at least 25 components of the core regulatory circuitry in the cell and at least 6, at least 7, at least 8, at least 9, at least 10, at least 15, at least 20 or at least 25 targets of the master transcription factors in the core regulatory circuitry. In some embodiments, the method comprises modulating all components of the core regulatory circuitry in the cell, and at least one target of a master transcription factor in the core regulatory circuitry. In some embodiments, the method comprises modulating at least one component of the core regulatory circuitry in the cell, and all of the targets of the master transcription factor in the core regulatory circuitry. In some embodiments, the method comprises modulating all components of the core regulatory circuitry in the cell. In some embodiments, the method comprises modulating all targets of master transcription factors in the core regulatory circuitry.

In some aspects, the disclosure relates to reprogramming cells of a first cell type to cells of a second cell type, e.g., to alter the identity of the cell of the first cell type. In some aspects, the disclosure provides a method of reprogramming a cell of a first cell type to a cell of a second cell type, the method comprising modulating at least one component of the core regulatory circuitry of the second cell type in the cell of the first cell type. In some aspects, the disclosure provides a method of reprogramming a cell of a first cell type to a cell of a second cell type, the method comprising modulating at least one component of the cell identity program of the second cell type in the cell of the first cell type. In some context, "modulating at least one component of the core regulatory circuitry and/or cell identity program" comprises activating the at least one component of the core regulatory circuitry and/or cell identity program, e.g., activating a transcriptional coactivator. Those skilled in the art will appreciate that activation of the at least one component of the core regulatory circuitry and/or cell identity program can be accomplished in a variety of ways, e.g., alone or in combination with conventional reprogramming methods. In some embodiments, activating the at least one component comprises expressing the at least one component of the core regulatory circuitry and/or cell identity program of the second cell type in the cell of the first type. Such expression can be accomplished using methods such as DNA transfection, for example transient transfection, mRNA transfection, viral infection, etc. It should be appreciated that expression of core regulatory circuitry for purposes of reprogramming can be conditional, e.g., inducible, e.g., under control of an inducible promoter, e.g., using an inducible expression system, e.g., Tet-On, Tet-Off. In some embodiments, activating the at least one component comprises introducing the at least one component of the core regulatory circuitry and/or cell identity program of the second cell type into the cell of the second type. For example, at least one component of the core regulatory circuitry and/or cell identity program of the second cell type, e.g., in polypeptide form, can be directly introduced into the cell of the first cell type. Such polypeptides may, for example, be purified from natural sources, produced in vitro or in vivo in suitable expression systems using recombinant DNA technology (e.g., by recombinant host cells or in transgenic animals or plants), synthesized through chemical means such as conventional solid phase peptide synthesis, and/or methods involving chemical ligation of synthesized peptides (see, e.g., Kent, S., J Pept Sci., 9(9):574-93, 2003 or U.S. Pub. No. 20040115774), or any combination of the foregoing. In some embodiments, activating the at least one component comprises contacting the cell with an agent that activates expression of the at least one component of the core regulatory circuitry and/or cell identity program of the second cell type in the cell of the first type. In some embodiments, activation of the at least one component of the core regulatory circuitry and/or cell identity program of the second cell type comprises any combination of the above methods.

In some context, "modulating at least one component of the core regulatory circuitry and/or cell identity program" comprises repressing the at least one component of the core regulatory circuitry and/or cell identity program. For example, if the at least one component of the core regulatory circuitry and/or cell identity program comprise a repressor, reducing the repressor's activity in the context of several other transcriptional activators, for example transiently, could result in activation of the core regulatory circuitry and/or cell identity program of the second cell type thereby reprogramming the cell. The disclosure contemplates any suitable method of repressing the at least one component of the core regulatory circuitry and/or cell identity program (e.g., transcriptional repressor). Exemplary methods of repressing the at least one component include contacting the cell or tissue with a dominant negative mutant of the transcriptional repressor, contacting the cell or tissue with a nucleic acid that inhibits transcription or translation of the transcriptional repressor, e.g., antisense oligonucleotides directed against the sequence encoding the transcriptional repressor or a regulatory element that drives expression of the transcriptional repressor, e.g., a super-enhancer or DNA sequence binding motif, shRNA, microRNA, aptamers, small molecule inhibitors that interfere with binding between the transcriptional repressor and a regulatory element, etc.

It should be appreciated that the extent of reprogramming of the cell from the first cell type to the cell of the second cell type is likely to increase proportionately the extent of core regulatory circuitry and/or cell identity program components of the cell of the second cell type activated in the cell of the first cell type. In other words, the more the activation profile of core regulatory circuitry and/or cell identity program components of the cell of the first type resembles the core regulatory circuitry and/or cell identity program of the cell of the second type, the more the cell of the first type will phenotypically resemble the cell of the second type, i.e., the reprogramming efficiency will increase with increased activation of the desired core regulatory circuitry and/or cell identity program components. For the avoidance of doubt, it should be appreciated that the expressions "activation profile" and "activation of the core regulatory circuitry and/or cell identity program" refer to the overall effect that modulation of the components of the core regulatory circuitry and/or cell identity programs have on the cell or tissue, taking into account the fact that both activating a transcriptional activator or coactivator and repressing or inhibiting a transcriptional repressor or corepressor result in an overall net effect that favors increased activity or activation of the core regulatory circuitry and/or cell identity program in such a way that the identity of the cell is reprogrammed from the cell of the first type to the cell of the second type as a result of such increased activity or activation. In some embodiments, modulating the at least one component of the core regulatory circuitry and/or cell identity program increases the overall activation or activity of the core transcriptional circuitry and/or cell identity program (e.g., by driving the expression of core transcriptional circuitry target genes) by at least 5%, 10%, 15%, 20%, 25%, 30%, 35%, 40%, 50%, 55%, 60%, 70%, 75%, 80%, 85%, 90%, or 95% or more. In some embodiments, modulating the at least one component of the core regulatory circuitry and/or cell identity program increases the overall activation or activity of the core transcriptional circuitry and/or cell identity program by at least 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3 fold, 4 fold, 5 fold, 6 fold, 7 fold, 8 fold.

In some embodiments, at least two components, at least three components, at least four components, at least five components, at least six components, at least seven components, at least eight components, at least nine components, or at least ten components of the core regulatory circuitry and/or cell identity program of the second cell type are modulated (e.g., activated and/or repressed) in the cell of the first type. In some embodiments, at least 5%, at least 10%, at least 15%, at least 20%, at least 25%, at least 30%, at least 33%, at least 35%, at least 40%, at least 45%, at least 50% or more of the components of the core regulatory circuitry of the cell of the second type are modulated (e.g., activated and/or repressed) in the cell of the first type. In some embodiments, at least 55%, at least 60%, at least 65%, at least 70%, at least 75%, at least 80%, at least 85%, at least 87%, or at least 90% of the components of the core regulatory circuitry and/or cell identity program of the cell of the second type are modulated (e.g., activated and/or repressed) in the cell of the first type. In some embodiments, at least 91%, at least 92%, at least 93%, at least 94%, at least 95%, at least 96%, at least 97%, at least 98%, at least 99%, or 100% of the components of the core regulatory circuitry and/or cell identity program of the cell of the second type are modulated (e.g., activated and or repressed) in the cell of the first type.

In some embodiments, modulating the at least one component of the core regulatory circuitry and/or cell identity program of the second cell type in the cell of the first type occurs ex vivo. In some embodiments, modulating the at least one component of the core regulatory circuitry and/or cell identity program of the second cell type in the cell of the first type occurs in vivo. In some embodiments, the method of reprogramming optionally comprises modulating (e.g., inhibiting) at least one component of the core regulatory circuitry and/or cell identity program of the first cell type.

It should be appreciated that the methods can be used to reprogram any cell of a first cell type to a cell of a second cell type as long as the core regulatory circuitry and/or cell identity program of the cell of the second cell type is known. In some embodiments, the cell of the first cell type comprises the core regulatory circuitry and/or cell identity program of a diseased cell, and the cell of the second cell type comprises the core regulatory circuitry and/or cell identity program of a normal cell. In some embodiments, the cell of the first cell type comprises the core regulatory circuitry and/or cell identity program of a terminally differentiated cell, and the cell of the second cell type comprises the core regulatory circuitry and/or cell identity program of a less differentiated cell. In some embodiments, the cell of the first cell type comprises the core regulatory circuitry and/or cell identity program of a first somatic cell type, and the cell of the second cell type comprises the core regulatory circuitry and/or cell identity program of a second somatic cell type. In some embodiments, the cell of the first cell type comprises the core regulatory circuitry and/or cell identity program of a somatic cell, and the cell of the second cell type comprises the core regulatory circuitry and/or cell identity program of an embryonic cell. In some embodiments, the cell of the first cell type comprises the core regulatory circuitry and/or cell identity program of a first tissue type, and the cell of the second type comprises the core regulatory circuitry and/or cell identity program of a second tissue type. In some embodiments, the cell of the first cell type comprises the core regulatory circuitry and/or cell identity program of a skin or fat cell, and the cell of the second cell type comprises the core regulatory circuitry and/or cell identity program of an internal cell or tissue. In some embodiments, the cell of the first cell type comprises the core regulatory circuitry and/or cell identity program of a tumor cell or tissue, and the cell of the second cell type comprises the core regulatory circuitry and/or cell identity program of a healthy cell or tissue.

In some embodiments, nucleic acids encoding one or more core regulatory circuitry components can be incorporated into a vector, which can be introduced into a cell whose reprogramming is desired. Accordingly, in some embodiments, the disclosure provides kits comprising at least one nucleic acid encoding a core regulatory circuitry component of a cell type of interest.

In some embodiments, reprogramming is effected without genetically modifying the cell being reprogrammed. In some embodiments, cells to be reprogrammed may be obtained from a patient (or donor, optionally one who is immunocompatible with the patient), reprogrammed ex vivo, and at least some of the resulting cells can be administered to the patient for purposes of cell-based therapy, e.g., regenerative medicine, e.g., restoring a degenerated, injured, damaged, or dysfunctional organ or tissue, cell-based immunotherapy (e.g., for cancer or an infection), or used to construct a tissue or organ ex vivo, which can be implanted into the patient. In some embodiments, the reprogrammed cells can optionally be expanded ex vivo prior to reprogramming, after reprogramming, or both.

In some aspects, the disclosure provides methods for determining a subset of core regulatory circuitry components for a cell or tissue that are sufficient to effect reprogramming of the cell or tissue, comprising systematically introducing all but a first, a second, a third, . . . up to an Nth (where N is an integer equal to the total number of core regulatory circuitry components for the cell or tissue) of the core regulatory circuitry components into the cell or tissue to be reprogrammed, and evaluating combinations of core regulatory circuitry components that are effective in reprogramming the cell or tissue.

The reprogramming methods described herein can be used for any purpose which would be desirable to a skilled person, e.g., use in cell therapy, e.g., autologous cell therapy. As an example, fibroblasts can be obtained from an individual and reprogrammed to muscle cells ex vivo for use in tissue repair. As another example, white fat can be reprogrammed to brown fat.

Aspects of the disclosure relate to diagnosing cell identity program-related disorders. As used herein a "cell identity program-related disorder" refers to any disease, condition, or disorder that is caused, correlated to, or associated with a deviation in sequence, expression, or activity of a component of a cell identity program in a cell or tissue, e.g., a diseased cell or tissue of interest, e.g., obtained from a subject suffering from any disease, condition, or disorder described herein. In some aspects, a method of diagnosing a cell identity program-related disorder comprising determining whether the cell identity program of the cell or tissue is enriched for disease-associated variations. Any suitable method can be used to determine enrichment of disease-associated variations in the cell identity program of a cell or tissue of interest. In some embodiments, determining whether the cell identity program of the cell or tissue is enriched for disease-associated variations comprises obtaining a sample comprising a cell or tissue of interest, and detecting the presence of disease-associated variations in components of the cell identity program of the cell or tissue of interest, wherein the cell identity program of the cell or tissue is enriched for disease-associated variations if at least two disease-associated variations are detected in the components of the cell identity program of the cell or tissue of interest.

Those skilled in the art will appreciate that the sensitivity and specificity of the diagnostic methods may increase as a function of the overall number of disease-associated variations detected in the cell identity program relative to the overall number of components in the cell identity program. In some embodiments, the cell identity program of the cell or tissue is enriched for disease-associated variations if at least three; at least four; at least five; or at least six disease associated variations are detected in the components of the cell identity program of the cell or tissue of interest. In some embodiments, the cell identity program of the cell or tissue is enriched for disease-associated variations if at least 7, at least 8, at least 9, or at least 10 disease-associated variations are detected in the components of the cell identity program. In some embodiments, the cell identity program of the cell or tissue is enriched for disease-associated variations if at least 5%, at least 6%, at least 7%, at least 8%, at least 9%, or at least 10% of the components of the cell identity program are determined to contain a disease-associated variation. In some embodiments, the cell identity program of the cell or tissue is enriched for disease-associated variations if at least 11%, at least 12%, at least 13%, at least 14%, at least 15%, at least 16%, at least 17%, at least 88%, at least 19%, at least 20%, at least 25% or more of the components of the cell identity program are determined to contain a disease-associated variation. In some embodiments, the cell identity program of the cell or tissue is enriched for disease-associated variations if at least 30%, at least 33%, at least 35%, at least 37%, at least 39%, at least 42%, at least 45%, at least 47%, at least 50%, at least 55%, at least 60% or more of the components of the cell identity program are determined to contain a disease-associated variation.

As used herein, the phrase "disease-associated variations" and "disease-associated variants" refers to variations in sequences, expression levels, or activity of components of a cell identity program in a particular cell or tissue of interest. In some embodiments, the disease associated variations comprise single nucleotide polymorphisms. In some embodiments, the disease-associated variations comprise GWAS variants. Any SNPs linked to a phenotypic trait or disease can be of use herein. In some embodiments, the SNP comprises one of more than 5,000 SNPs and diseases identified in more than 1,600 GWAS studies described in PCT International Application No. PCT/US2013/066957 (Attorney Docket No. WIBR-137-WO1), filed Oct. 25, 2013, the entirety of which is incorporated by reference herein.

In some embodiments, the disease-associated variations comprise GWAS variants in a super-enhancer associated with the core regulatory circuitry in the cell or tissue of interested selected from the group consisting of i) at least one gene encoding a master transcription factor, (ii) the master transcription factor encoded by the at least one gene, or (iii) at least one target of the master transcription factor. In some embodiments, the GWAS variant is selected from the group consisting of (i) a GWAS variant from Alzheimer disease present in the cell identity program of brain hippocampus; (ii) a GWAS variant from systemic lupus erythematosus present in the cell identity program of CD20 cells; (iii) a GWAS variant from fasting insulin trait present in the cell identity program of adipose nuclei; (iv) a GWAS variant from ulcerative colitis present in the cell identity program of sigmoid colon; (vi), a GWAS variant from electrocardiographic traits present in the cell identity program of left ventricle.

Aspects of the disclosure relate to various methods of treatment, e.g., treating cell identity program-related disorders. In some aspects, the disclosure provides a method of treating a cell identity program-related disorder in a subject in need thereof, comprising modulating at least one abnormal component of a cell identity program in a diseased cell or tissue of the subject. As used herein, "abnormal component" of a cell identity program refers to a component of a cell identity program which differs in sequence, expression and/or activity in the diseased cell or tissue compared to the sequence, expression or activity of the component in the corresponding healthy or normal cell or tissue. In some embodiments, modulating at least one abnormal component of the cell identity program in the diseased cell or tissue of the subject comprises administering to the subject an effective amount of an agent that modulates the at least one abnormal component of the cell identity program.

Aspects of the disclosure involve the use of agents. The disclosure contemplates the use of any agent that is suitable for a specified purpose, e.g. agents that modulate at least one component of a cell identity program, e.g., at least one abnormal component. Exemplary agents of use herein include, without limitation, small organic or inorganic molecules; saccharides; oligosaccharides, polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, and aptamers; an extract made from biological materials selected from the group consisting of bacteria, plants, fungi, animal cells, and animal tissues; naturally occurring or synthetic compositions; and any combination thereof.

In some embodiments, diseased cell or tissue comprises a tumor cell or tissue. In some embodiments, the diseased cell or tissue comprises a cell or tissue listed in Table 2, and the abnormal component comprises at least one component of the cell identity program of the cell selected from the group consisting of (i) a gene encoding a master transcription factor, (ii) the master transcription factor encoded by the gene, (iii) a target of the master transcription factor, (iv) a super-enhancer associated with any of (i)-(iii), or a component of the super-enhancer. In some embodiments, the method comprises diagnosing the subject as having the cell identity program-related disorder, e.g., according to a method described herein.

Aspects of the disclosure relate to identifying candidate modulators of core regulatory circuitry components of cells or tissues. Such candidate modulators can be useful, e.g., for reprogramming cells or tissues or treating diseases in which one or more components of the core regulatory circuitry comprises an abnormal component, e.g., the component comprises a disease-associated variant. In some aspects, the disclosure provides a method of identifying a candidate modulator of at least one component of the core regulatory circuitry of a cell or tissue, comprising: a) contacting a cell or tissue with a test agent; and b) assessing the ability of the test agent to modulate at least one component of the core regulatory circuitry of the cell or tissue, wherein the test agent is identified as a candidate modulator of the at least one component of the core regulatory circuitry of the cell or tissue if the at least one component of the core regulatory circuitry is activated or inhibited in the presence of the test agent. Activation or inhibition of the at least one component of the core regulatory circuitry can be measured by detecting and quantifying expression or activity of the at least one component of the core regulatory circuitry.

In some embodiments, the at least one component of the core regulatory circuitry of the cell or tissue comprises a reprogramming factor or a cell identity gene. In some embodiments, the at least one component of the core regulatory circuitry of the cell or tissue comprises a disease-associated variant.

In some aspects, the disclosure relates to methods of reprogramming cells comprising contacting the cells with candidate modulators identified according to the methods described herein. In some embodiments, at least one component of the core regulatory circuitry of the cell comprises a disease-associated variant. In some embodiments, contacting occurs in vivo or ex vivo.

Aspects of the disclosure relate to methods of identifying candidate modulators of cell identity program components in cells or tissue. In some aspects, the disclosure provides a method of identifying a candidate modulator of at least one component of the cell identity program of a cell or tissue, comprising: a) contacting a cell or tissue with a test agent; and b) assessing the ability of the test agent to modulate at least one component of the cell identity program of the cell or tissue, wherein the test agent is identified as a candidate modulator of the at least one component of the cell identity program of the cell or tissue if the at least one component of the cell identity program of the cell or tissue is activated or inhibited in the presence of the test agent. In some embodiments, the at least one component of the cell identity program of the cell or tissue comprises a reprogramming factor or a cell identity gene. In some embodiments, the at least one component of the cell identity program of the cell or tissue comprises a disease-associated variant.

In some aspects, the disclosure provides a method of reprogramming a cell comprising contacting the cell with the candidate modulator identified according to a method described herein. In some embodiments, at least one component of the core regulatory circuitry of the cell comprises a disease-associated variant. In some embodiments, contacting occurs in vivo or ex vivo.

Aspects of the disclosure relate to methods of identifying targets for drug discovery (e.g., cancer drug discovery). Such methods are useful for identifying core regulatory circuitry or cell identity programs of tumor cells or tissues which can be modulated in a way that shifts the tumor cells or tissues back towards the normal state, e.g., if a core regulatory circuitry component is overexpressed in tumor cells or tissue compared to normal cells or tissue, inhibiting its expression or activity in the tumor could shift the tumor cells or tissues back towards the normal state.

In some aspects, the disclosure provides, a method of identifying a target for drug discovery comprising identifying a variation in at least one component of the core regulatory circuitry of a cell or tissue that is more prevalent in subjects suffering from a disease than in healthy subjects, wherein the at least one component of the core regulatory circuitry of the cell or tissue that is more prevalent in subjects suffering from a disease than in healthy subjects comprises a disease-associated variant, and wherein the disease-associated variant is a target for drug discovery.

In some aspects, the disclosure provides a method of identifying a target for drug discovery comprising identifying a variation in at least one component of the cell identity program of a cell or tissue that is more prevalent in subjects suffering from a disease than in healthy subjects, wherein the at least one component of the cell identity program of the cell or tissue that is more prevalent in subjects suffering from a disease than in healthy subjects comprises a disease-associated variant, and wherein the disease-associated variant is a target for drug discovery.

In some embodiments, the target for drug discovery comprises a target for diagnostic purposes.

In some aspects, the disclosure provides a method of identifying a target for anti-cancer drug discovery comprising: a) comparing the core regulatory circuitry of a tumor cell or tissue with the core regulatory circuitry of a corresponding non-tumor cell or tissue; and b) identifying at least one component that differs between the core regulatory circuitry of the tumor cell or tissue and the corresponding non-tumor cell or tissue, wherein the at least one component that differs between the core regulatory circuitry of the tumor cell or tissue and the corresponding non-tumor cell or tissue is identified as a target for anti-cancer drug discovery. In some embodiments, a gene regulated by the at least one component is identified as a target for anti-cancer drug discovery. In some embodiments, the at least one component differs in sequence, expression, and/or activity.

In some aspects, the disclosure provides a method of identifying an anti-cancer agent comprising identifying a modulator of the target for anti-cancer drug discovery identified according to a method described herein.

In some aspects, the disclosure provides a method treating a cancer characterized by tumor cell or tissue comprising the target for anti-cancer drug discovery, comprising administering to a subject suffering from the cancer an effective amount of the anti-cancer agent identified according to a method described herein.

In some embodiments one or more steps of a method described herein is performed at least in part by a machine, e.g., computer (e.g., is computer-assisted) or other apparatus (device) or by a system comprising one or more computers or devices. "Computer-assisted" as used herein encompasses methods in which a computer is used to gather, process, manipulate, display, visualize, receive, transmit, store, or in any way handle or analyze information (e.g., data, results, structures, sequences, etc.). A method may comprise causing the processor of a computer to execute instructions to gather, process, manipulate, display, receive, transmit, or store data or other information. The instructions may be embodied in a computer program product comprising a computer-readable medium. A computer-readable medium may be any tangible medium (e.g., a non-transitory storage medium) having computer usable program instructions embodied in the medium. Any combination of one or more computer usable or computer readable medium(s) may be utilized in various embodiments. A computer-usable or computer-readable medium may be or may be part of, for example but not limited to, an electronic, magnetic, optical, electromagnetic, infrared, or semiconductor system, apparatus, or device. Examples of a computer-readable medium include, e.g., a hard disk, a random access memory (RAM), a read-only memory (ROM), an erasable programmable read-only memory (e.g., EPROM or Flash memory), a portable compact disc read-only memory (CDROM), a floppy disk, an optical storage device, or a magnetic storage device. In some embodiments a method comprises transmitting or receiving data or other information over a communication network. The data or information may be generated at or stored on a first computer-readable medium at a first location, transmitted over the communication network, and received at a second location, where it may be stored on a second computer-readable medium. A communication network may, for example, comprise one or more intranets or the Internet.

In some embodiments, a method of identifying the CRC and/or CIP may be embodied on a non-transitory computer-readable medium. In some embodiments, a CRC and/or CIP identified in accordance with the methods described herein may be embodied on a non-transitory computer-readable medium. In some embodiments a computer is used in sample tracking, data acquisition, and/or data management. For example, in some embodiments a sample ID is entered into a database stored on a computer-readable medium in association with a measurement or determination of a sequence, expression and/or activity. The sample ID may subsequently be used to retrieve a result of determining sequence, expression and/or activity in the sample. In some embodiments, automated image analysis of a sample is performed using appropriate software, comprising computer-readable instructions to be executed by a computer processor. For example, a program such as ImageJ (Rasband, W. S., ImageJ, U. S. National Institutes of Health, Bethesda, Md., USA, http://imagej.nih.gov/ij/, 1997-2012; Schneider, C. A., et al., Nature Methods 9: 671-675, 2012; Abramoff, M. D., et al., Biophotonics International, 11(7): 36-42, 2004) or others having similar functionality may be used. In some embodiments, an automated imaging system is used. In some embodiments an automated image analysis system comprises a digital slide scanner. In some embodiments the scanner acquires an image of a slide (e.g., following IHC for detection of a gene product) and, and, optionally, stores or transmits data representing the image. Data may be transmitted to a suitable display device, e.g., a computer monitor or other screen. In some embodiments an image or data representing an image is added to a patient medical record.

In some embodiments a machine, e.g., an apparatus or system, is adapted, designed, or programmed to perform an assay for measuring or determining sequence, expression or activity of a cell identity program component listed in Table 1. In some embodiments an apparatus or system may include one or more instruments (e.g., a PCR machine), an automated cell or tissue staining apparatus, a device that produces, records, or stores images, and/or one or more computer processors. The apparatus or system may perform a process using parameters that have been selected for detection and/or quantification of a gene product of master transcription factor listed in Table 1, e.g., in samples of tumor cells or tissue. The apparatus or system may be adapted to perform the assay on multiple samples in parallel and/or may comprise appropriate software to provide an interpretation of the result. The apparatus or system may comprise appropriate input and output devices, e.g., a keyboard, display, printer, etc. In some embodiments a slide scanning device such as those available from Aperio Technologies (Vista, Calif.), e.g., the ScanScope AT, ScanScope CS, or ScanScope FL or is used.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Example 1

Core Transcriptional Circuitries of Human Cells

Introduction

The pathways involved in complex biological processes such as metabolism have been mapped through the efforts of many laboratories over many years and have proven exceptionally valuable for basic and applied science (Krebs 1940; Kanehisa et al. 2012). Although much is known about the general mechanisms involved in control of gene transcription, the complex pathways involved in the control of each cell's gene expression program have yet to be mapped in most cells. For some cell types, it is evident that core transcription factors (TFs) regulate their own genes and many others, forming the central core of a definable pathway. For most mammalian cell types, however, there remains a limited understanding of these pathways. These gene control pathways are important to decipher because they have the potential to define cell identity, enhance cellular reprogramming for regenerative medicine, and improve our understanding of transcriptional dysregulation in disease.

There is considerable evidence that the control of cell type specific gene expression programs in mammals is dominated by a small number of the many hundreds of TFs that are expressed in each cell type (Graf and Enver 2009; Lee and Young 2013; Buganim et al. 2013; Morris and Daley 2013). These core TFs are generally expressed in a cell type-specific or lineage-specific manner and can reprogram cells from one cell type to another. In embryonic stem cells (ESCs), where transcriptional control has been most extensively studied, the core TFs POU5F1 (also known as OCT4), SOX2 and NANOG have been shown to be essential for establishment or maintenance of ESC identity, and are among the factors capable of reprogramming cells into an ESC-like induced pluripotent stem cells (iPSCs) (Young 2011). These core TFs bind to their own genes and those of the other core TFs, forming an interconnected autoregulatory loop (Bayer et al. 2005), a property that is shared by the core TFs of other cell types (Odom et al. 2004, 2006; Sanda et al. 2012). The core TFs and the interconnected autoregulatory loop they form have been termed "core regulatory circuitry" (CRC) (Boyer et al. 2005). Because the ESC core TFs also bind to a large portion of the genes that are expressed in an ESC specific manner, we can posit that regulatory information flows from the CRC to this key portion of the cell's gene expression program, thus forming a map of information flow from CRC to cell type specific genes (Young 2011).

With limited knowledge of CRCs in most cell types, attempts to map the control of gene expression programs have thus far been dominated by efforts to integrate global information regarding gene-gene, protein-protein, gene-protein and regulatory element interactions nested in these networks (Gerstein et al. 2012; Neph et al. 2012; Yosef et al. 2013; Kemmeren et al. 2014; Rolland et al. 2014; Lefebvre et al. 2010). These global studies have provided foundational resources and important insights into basic principles governing transcriptional regulatory networks. These include the identification of recurring motifs of regulatory interactions (Lee et al. 2002; Alon 2007; Stergachis et al. 2014; Davidson 2010) and of groups of genes that participate in common biological processes (Bar-Joseph et al. 2003; Dutkowski et al. 2013). However, these network maps do not generally capture the notion that key control information flows from a small number of core TFs. Recent studies have revealed that core TFs bind clusters of enhancers called super-enhancers (SE) and that the super-enhancer associated genes include those encoding the core TFs themselves (Whyte et al. 2013; Hnisz et al. 2013, 2015). The ability to identify super-enhancer associated TF genes, and thus candidate core TFs, should permit modeling of CRCs for all human cell types for which super-enhancer data is available.

The present inventors describe herein a method to reconstruct cell type-specific CRCs based on the properties of core TFs identified in ESCs and several other cell types: they are encoded by genes whose expression is driven by super-enhancers and they bind to each other's super-enhancers in an interconnected autoregulatory loop. Reported herein are CRC models for 75 cell and tissue types. These models recapitulate and expand on previously described CRCs for well-studied cell types, and provide core circuitry models for a broad range of human cell types that can serve as a first step to further mapping of cell type specific gene expression control pathways.

Results

Models of Core Regulatory Circuitry

To construct CRC models of human cell types, the present inventors used the logic outlined in FIG. 1. Detailed studies of the transcriptional control of cell identity in ESCs and a few other cell types have shown that core TFs have three properties. Core TFs are encoded by genes associated with super-enhancers (Whyte et al. 2013; Hnisz et al. 2013), bind the SEs associated with their own gene (Whyte et al. 2013), and form fully interconnected autoregulatory loops with the other core TFs by binding enhancers together with the other core TFs (Boyer et al. 2005; Odom et al. 2004, 2006; Sanda et al. 2012) (FIG. 1A). Candidate core TFs were predicted for multiple cell and tissue types using these three criteria, as described below.

For 75 human cell and tissue types, the present inventors first identified the set of active genes that encode TFs that are proximal to SEs (FIG. 1B, step 1). SEs have high levels of signal density for H3K27ac and were identified from H3K27ac ChIP-seq data compiled from multiple laboratories (Table 1, below), as previously described (Hnisz et al. 2013). Recent chromatin conformation data indicates that SEs generally interact with the proximal active gene (Dowen et al. 2014), so the proximal active gene, identified through H3K27ac density at its TSS (see methods), was assigned as the regulatory target of each SE.

Figures 1C, 1D, 1E:
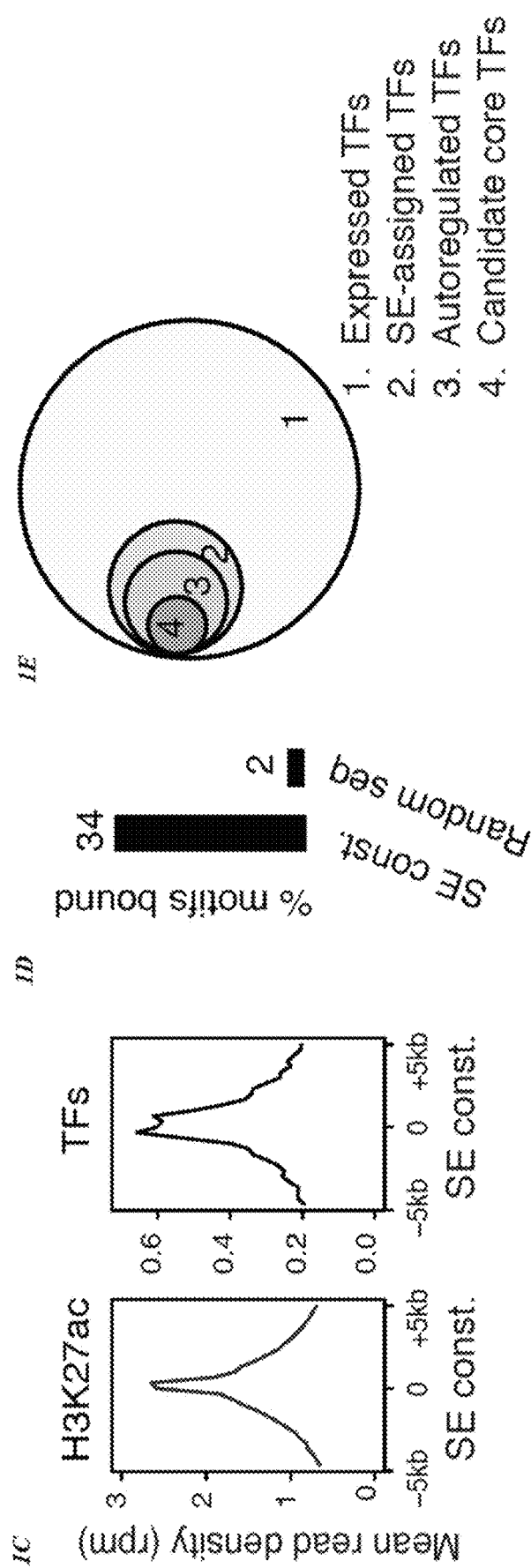

Previous studies have shown that core TFs bind their own super-enhancers (Whyte et al. 2013; Hnisz et al. 2013), so the present inventors next identified the set of SE-assigned TF genes whose products are predicted to bind their own SEs (FIG. 1B, step 2). Binding was predicted by searching SE constituents for DNA sequence motifs corresponding to the TF product of the gene assigned to that SE. The present inventors compiled DNA-binding sequence motifs for 695 TFs from multiple published sources (Mathelier et al. 2014; Jolma et al. 2013; Berger et al. 2008; Robasky and Bulyk 2011; Wei et al. 2010) (Tables 2A-2B, below) and scanned SE constituent sequences for the presence of the TF binding motifs, using the HMO software package from the MEME suite (Grant et al. 2011). SE constituents were used for the motif search, as TF binding distributions peak on the SE constituent sequences defined by H3K27ac ChIP-seq peak signal (FIG. 1C). Furthermore, the presence of multiple DNA sequence motifs at SE constituents is predictive of the binding of a TF, whereas this was not the case on average across the genome (FIG. 1D). This confirms previous observations of better TF binding prediction in open chromatin sequences compared to other regions of the genome (Zhong et al. 2013; Pique-Regi et al. 2011). The present inventors next considered the SE-assigned TF genes that were predicted to bind their own SE as autoregulated, as prior evidence in ESCs indicates that such genes do regulate their own expression (Tomioka et al. 2002; Okumura-Nakanishi et al. 2005; Navarro et al. 2012).

Figure 7:
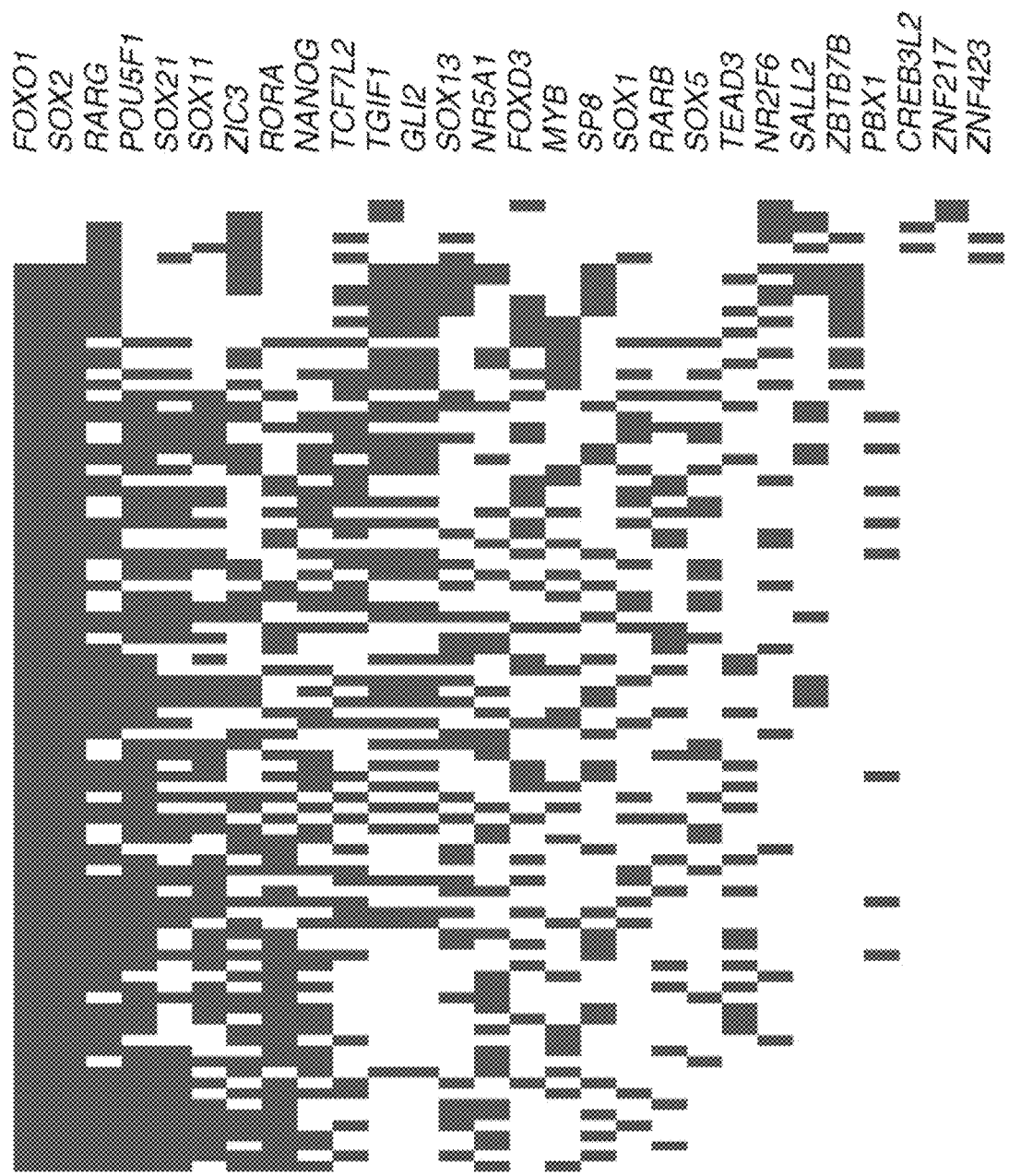
FIG. 7 depicts an example of CRC model selection out of multiple CRCs. The TF content of each possible interconnected autoregulatory loop (IAL) in H1 hESC is plotted in each column. The TFs were ranked vertically by decreasing fraction of their occurrences across all the possible IALs. The loops are ranked from left to right by average fraction of TF occurrence in the Loops. The CRC model corresponds to the leftmost loop.

To identify the SE-assigned TFs able to form an interconnected autoregulatory loop by binding to each other's super-enhancers, the present inventors next identified, from the set of TFs considered autoregulated, the TFs that are predicted to bind the SE of the other autoregulated through a motif analysis in SE constituents sequences (FIG. 1B, step 3). Interconnected autoregulatory loops were assembled for each cell or tissue type (FIG. 1A, step 3) and the loop containing the set of TFs most often represented across the set of loops as the representative model of CRC was selected (FIG. 7). On average, across 75 cell types, 15% of the genes considered expressed and encoding TFs were assigned to an SE (Table 3A, below), 9% were predicted to be autoregulated (Table 3B, below), and 3% were identified as candidate core TFs (FIG. 1E) (Table 3C, below).

hESC Core Regulatory Circuitry

The model of CRC predicted for human H1 ESCs (FIG. 2A, left panel) indicates that the approach described herein captures the previously described core TFs and CRC for ESCs, and suggests that additional TFs contribute to this core circuitry. The H1 ESC CRC contains three factors—POU5F1, SOX2, and NANOG—that are considered the foundation of the CRC in ESCs (Jaenisch and Young 2008; Young 2011). All three factors are essential for the pluripotent state (Nichols et al. 1998; Niwa et al. 2000; Avilion et al. 2003; Masui et al. 2007; Chambers et al. 2003; Mitsui et al. 2003; Silva et al. 2009; Theunissen et al. 2011), regulate their own genes and those encoding the other two factors (Catena et al. 2004; Kuroda et al. 2005; Okumura-Nakanishi et al. 2005; Chew et al. 2005; Rodda et al. 2005; Tomioka et al. 2002; Boyer et al. 2005; Loh et al. 2006), and can be used to reprogram fibroblasts to an induced pluripotent state (Yu et al. 2007; Takahashi and Yamanaka 2006).

Figure 2B:
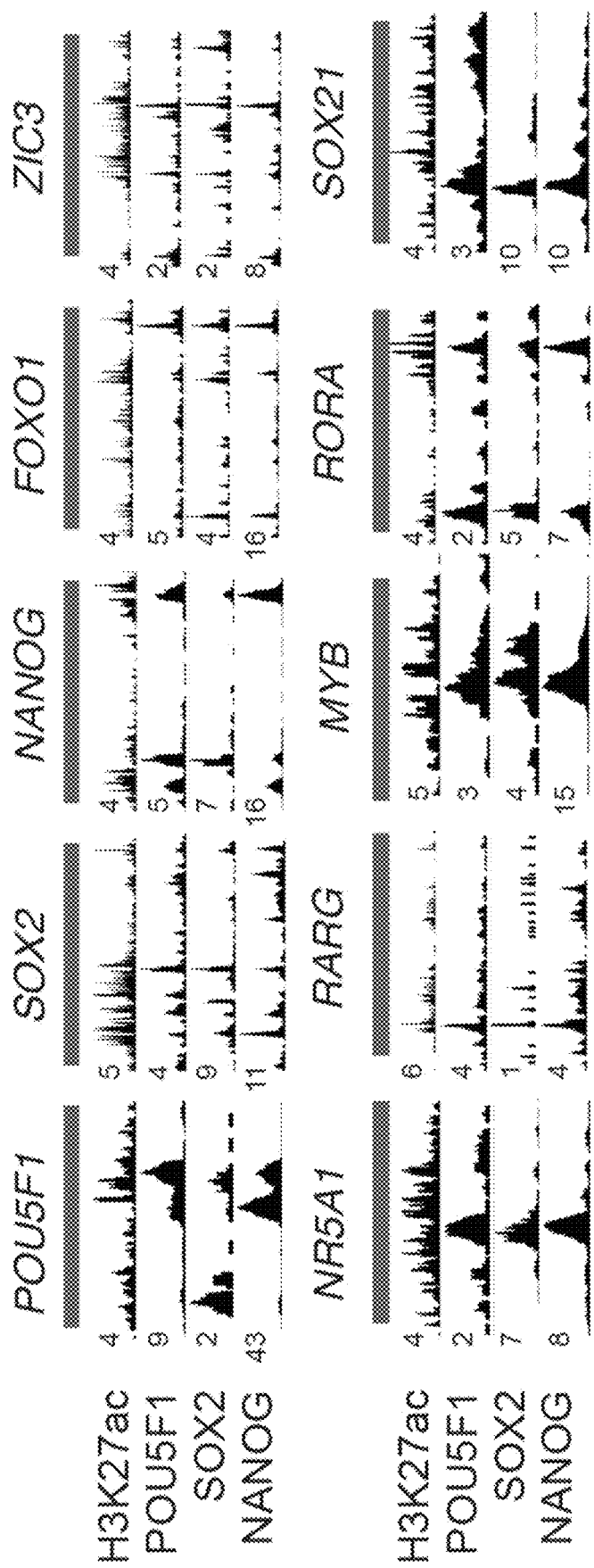

The results of the algorithm we described by the present inventors suggests that seven additional TFs contribute to the ESC CRC (FIG. 2A, left panel). Most of these factors have previously been implicated in control of the stem cell state, and there is ChIP-seq evidence indicating that their super-enhancers are bound by POU5F1, SOX2 and NANOG (FIG. 2B). FOXO1 and ZIC3 have previously been shown to be essential for the maintenance of pluripotency (Zhang et al. 2011; Lim. et al. 2007; Declercq et al. 2013). In hESC, FOXO1 regulates POU5F1 and SOX2 expression (Zhang et al. 2011). ZIC3 directly activates Nanog expression in mouse ESCs (mESCs) and can contribute to reprogramming of human fibroblasts into an induced pluripotent state (Lim et al. 2007; Declercq et al. 2013). NR5A1 (also known as SF1) and RARG can influence the pluripotent state (Guo and Smith 2010; Wang et al. 2011b) and both bind to regulatory regions of the POU5F1 gene and regulate its expression (Barnea and Bergman 2000; Guo and Smith 2010; Yang et al. 2007). The other three TFs—MYB, RORA and SOX21—are best known for their roles in other stem cells. MYB and RORA have roles in establishing or maintaining self-renewing populations of hematopoietic cells (Cheasley et al. 2011; Zuber et al. 2011; White and Weston 2000; Lieu and Reddy 2009; Doulatov et al. 2013), while SOX21 is involved in regulating pluripotency in intestinal stem cells, where its expression is influenced by SOX2 (Kuzmichev et al. 2012). Thus, there are multiple lines of evidence, summarized in Table 9 below, that support the inclusion of POU5F1, SOX2, NANOG, FOXO1, ZIC3, NR5A1, RARG, MYB, RORA and SOX21 in a model of hESC CRC.

In ESCs, loss of cell identity can be assayed by measuring POU5F1 protein levels, where reduced levels are associated with loss of pluripotency, and by counting cell nuclei, where reduced numbers can reflect loss of self-renewal (Kagey et al. 2010; Chia et al. 2010). To test whether the candidate core TFs play roles in control of ESC identity, the present inventors analyzed POU5F1 expression changes and cell nuclei number changes after depletion of each of these TFs using data from a genome-wide siRNA screen in H1 hESCs (Chia et al. 2010). These data confirm that the candidate core TFs contribute to pluripotency and/or survival and proliferation of hESCs (FIG. 8A). Gene-Set Enrichment Analysis (GSEA) of the set of candidate core TFs shows these factors are encoded by genes that are among those whose knockdown most impact POU5F1 expression and cell nuclei count (FIG. 8B and FIG. 8C). These functional assays in H1 hESCs thus provide supporting evidence for a functional role of the candidate core TFs in control of hESC identity.

Extended hESC Regulatory Circuitry

Figure 2C:
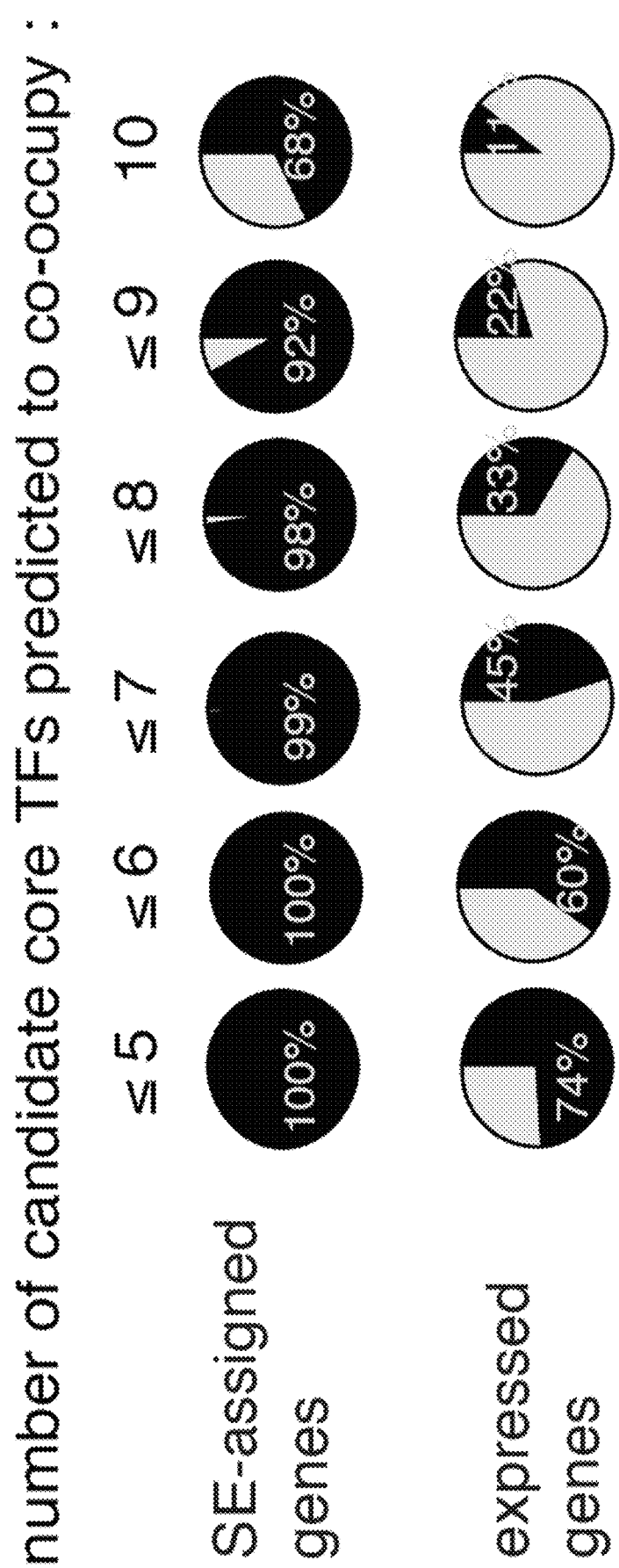

POU5F1, SOX2 and NANOG contribute to the formation of SEs at hundreds of active ESC genes that play prominent roles in cell identity (Whyte et al. 2013), suggesting that a simple extended model of regulatory information can be constructed to include these additional SE-assigned genes downstream of the core TFs. The present inventors identified the SE-assigned genes whose enhancers and promoters are predicted to be bound by the candidate core TFs in order to construct a model of extended hESC regulatory circuitry (FIG. 2A, right panel). Analysis shows the regulatory sequences of the SE-assigned genes are predicted to be bound by a greater number of candidate core TFs than the regulatory sequences of expressed genes (FIG. 2C). 68% of the SE-assigned genes are predicted to be bound by each of the core TFs. Experimental evidence (Kunarso et al. 2010) shows that POU5F1 contributes to the regulation of at least 30% (z-test p-value $<2.2^{e-16}$) of these downstream SE-assigned target genes (Table 4, below). Thus, in the model of extended hESC regulatory circuitry, the core TFs co-occupy and likely regulate the expression of a large portion of SE-assigned genes.

Figure 2D:
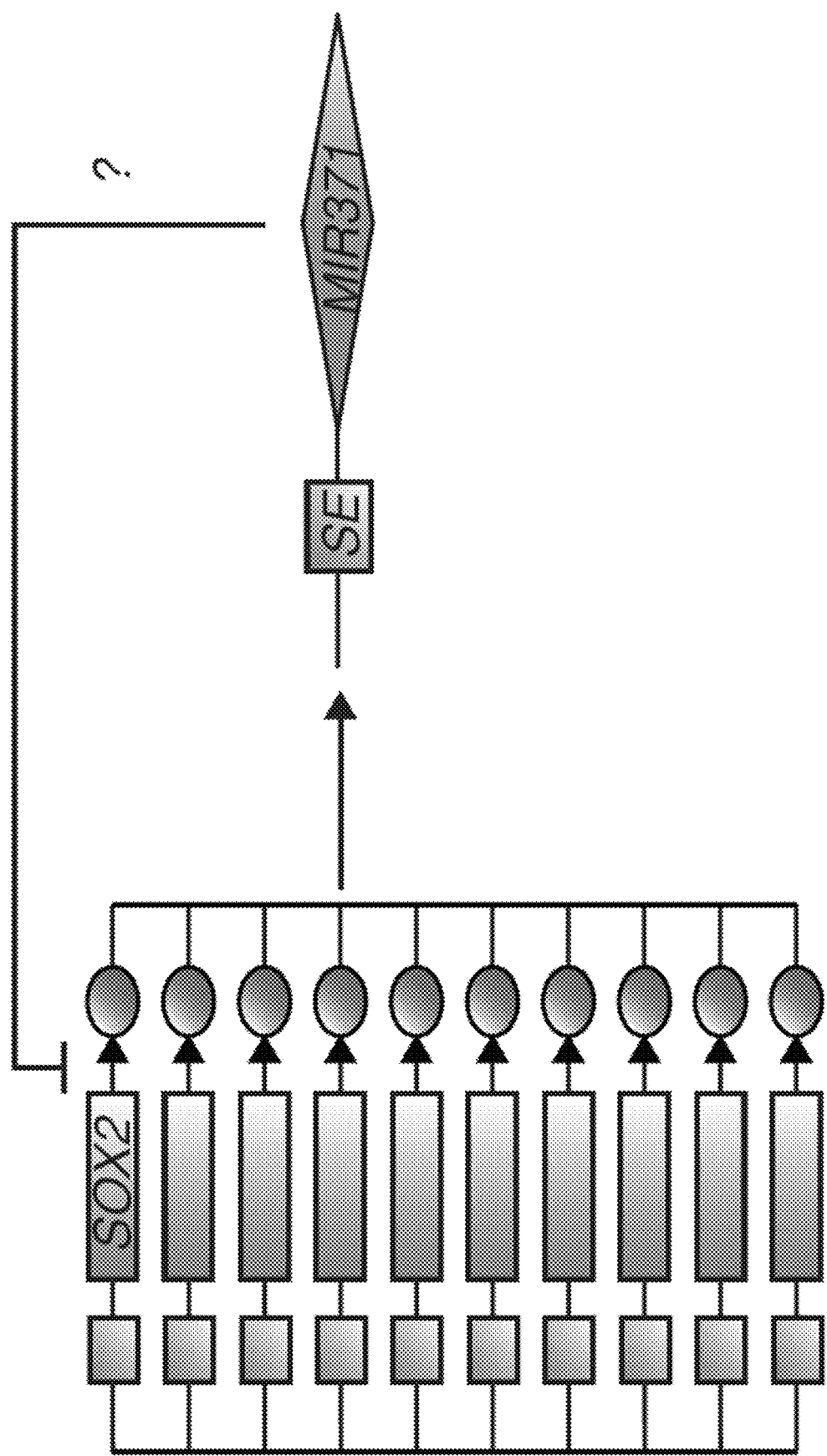
Figure 3A:
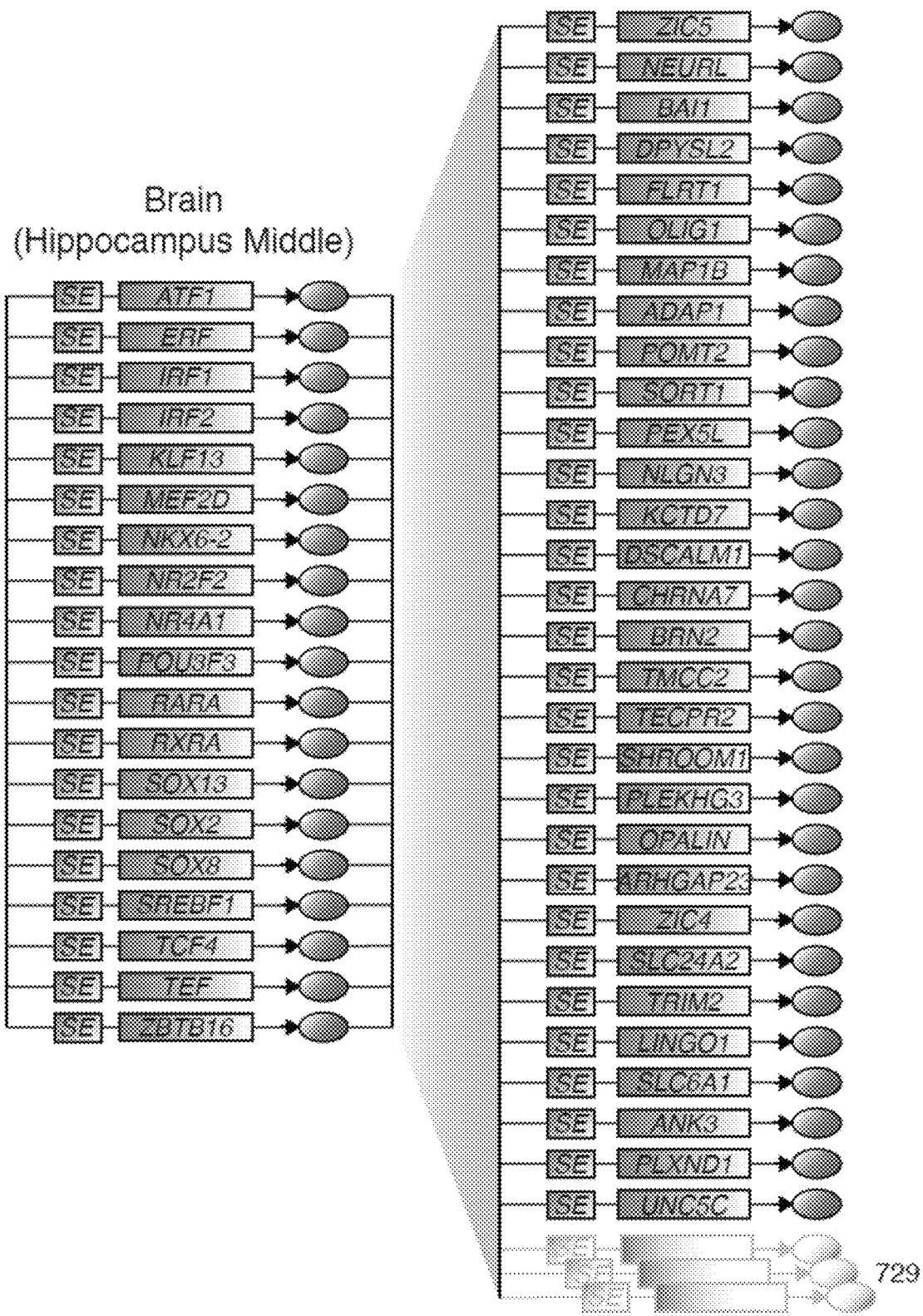
FIGS. 3A-3D depict core and extended regulatory circuits for multiple cells and tissue types, and in particular core and extended circuits for brain (hippocampus middle) (FIG. 3A), adipocytes (adipose nuclei) (FIG. 3B), heart (left ventricle) (FIG. 3C), and pancreas (FIG. 3D). The number of SE-assigned genes predicted to be co-occupied by each of the candidate core TFs and 30 examples of those are displayed on the right part of the maps.
Figure 3B:
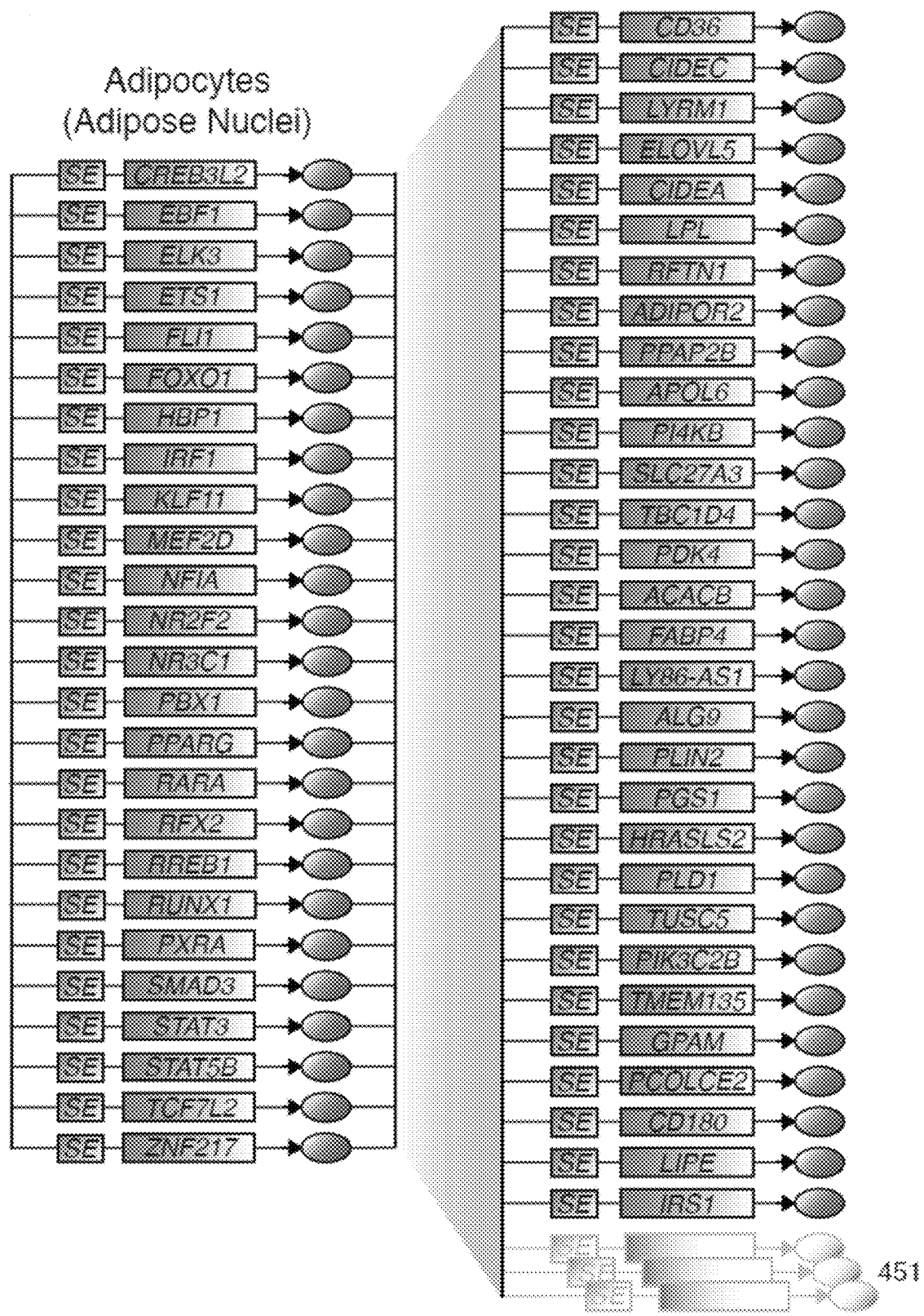
Figure 3C:
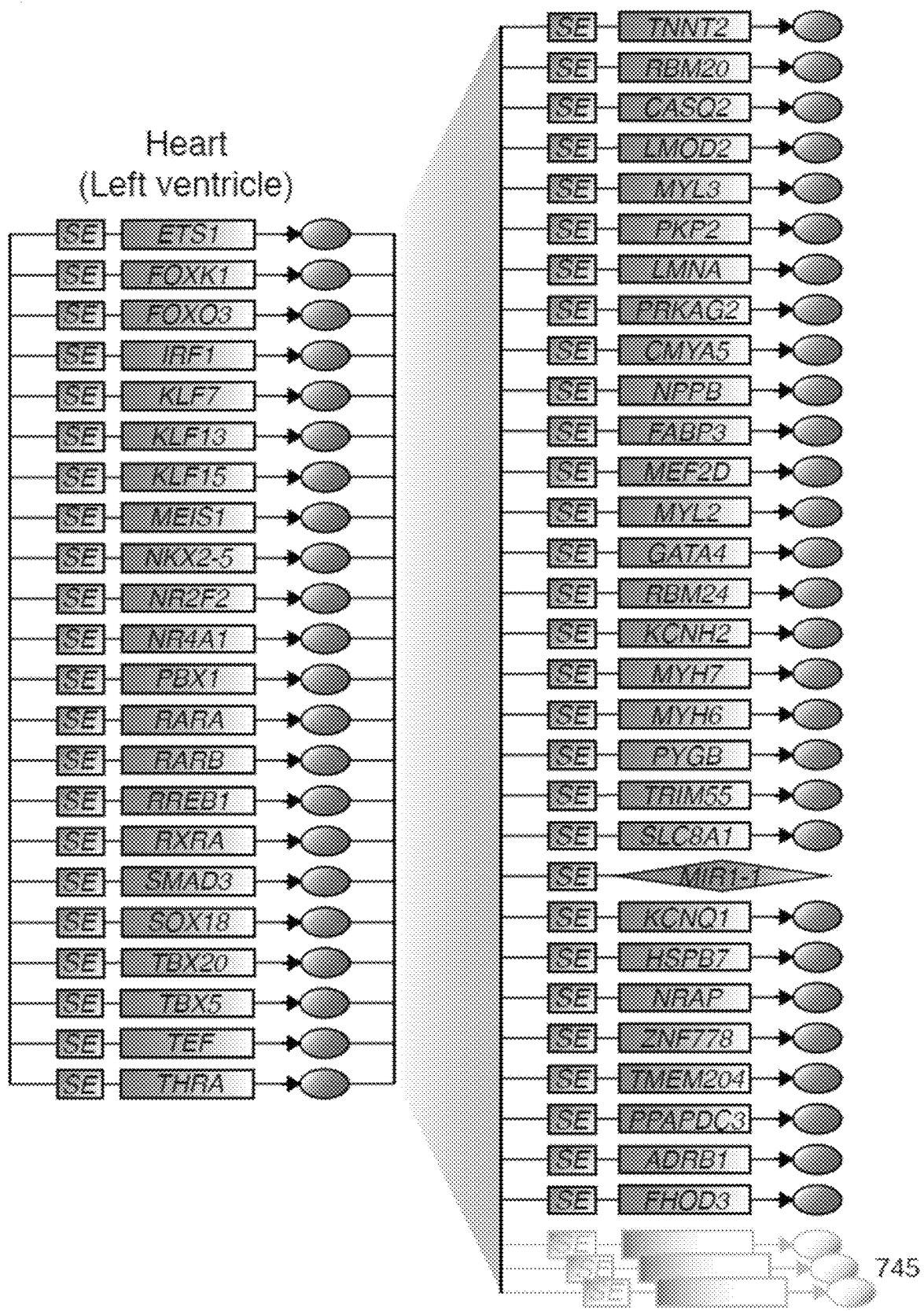
Figure 3D:
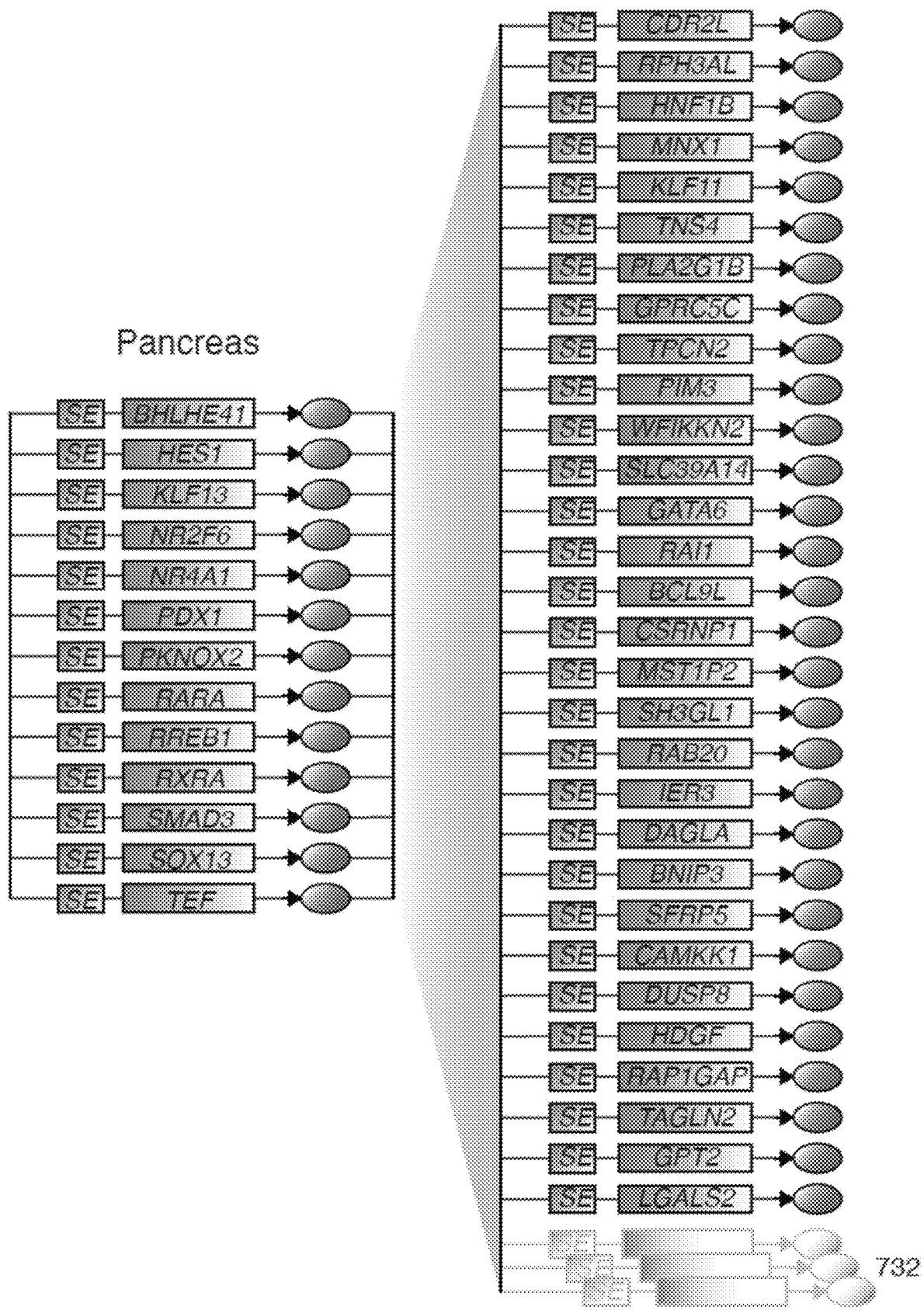

The model of extended hESC regulatory circuitry contains many genes that are known to play prominent roles in ESC biology (Young 2011). These include the TFs PRDM14, SALL4 and ZNE281, the chromatin regulators DNMT3B, JARID2 and SETDB1, and the miRNA miR-371a, all of which have established roles in pluripotency, self-renewal or differentiation (detailed functions and associated references in Table 5, below). Among the SE-assigned genes, some transcriptional regulators may create feedforward or feedback loops of regulation with the genes in the extended CRC to modulate the direct effect of core TFs. For example, miR-371a, the human homolog of miR-290 which is essential for mESC survival (Medeiros et al. 2011), may fine tune SOX2 expression in hESCs (FIG. 2D). SOX2 is identified as a highly probable target of miR-371a by multiple miRNA target predictor algorithms, including TargetScan (Lewis et al. 2005), miRDB (Wong and Wang 2015) and PITA (Kertesz et al. 2007) (Tables 6A-6C), and recent functional assays in human cancer cells (Li et al. 2015) support a role for miR371a in direct regulation of SOX2 expression. The present inventors therefore suggest that the ESC gene expression program is controlled by a CRC consisting of ten key TFs that 1) bind the SEs of their own genes and regulate their own expression, and 2) co-bind the SEs of many other genes important for ESC identity and regulate their expression.

CRC and Extended Regulatory Circuitry for Many Cell Types

The present inventors next developed models of CRC and extended regulatory circuitry for each of 75 human cell and tissue types (see, FIG. 3 and Table 3D, below). The predicted CRCs contain key transcriptional regulators of cell identity that have been previously identified (Table 7, below). This includes, for example, TBX5 in the heart (left ventricle)

Figure 4A:
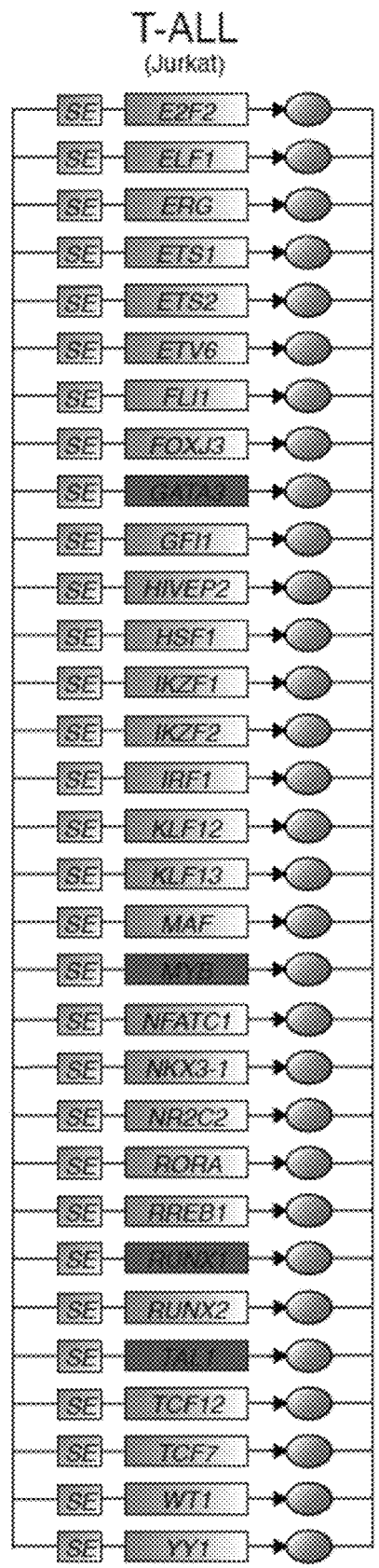
FIGS. 4A-4C depict experimental validation for T-ALL Jurkat cell circuitry.
Figure 9A:
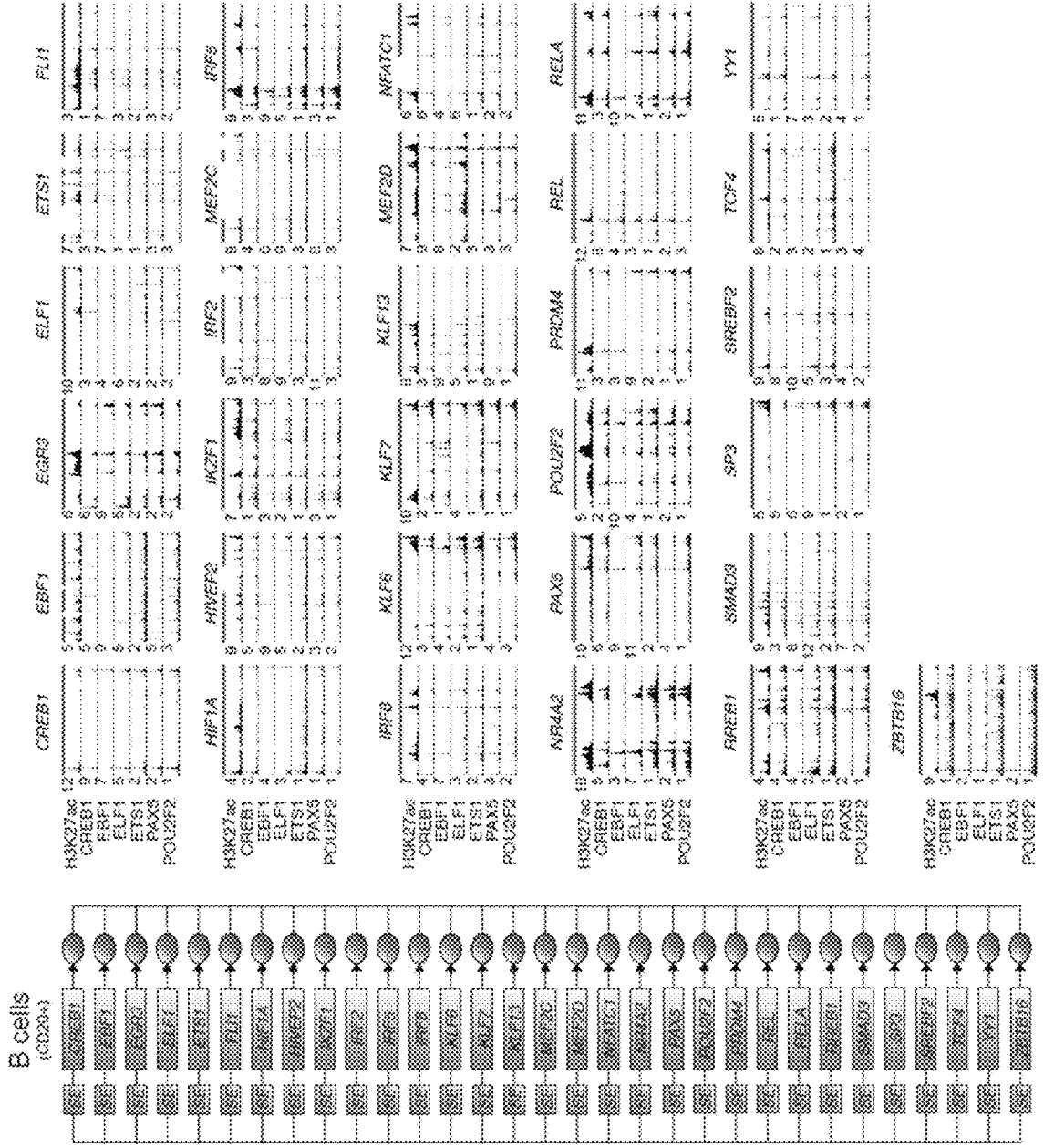
FIGS. 9A-9C depict ChIP-seq data for TFs in the CRC support the predicted binding interactions for three additional cell types. ChIP-seq data showing binding of the TFs to the SEs of the candidate core TF for CD20+ B-cell (FIG. 9A), HCT-116 colon cancer cell line (FIG. 9B), and MCF-7 breast cancer cell line (FIG. 9C) Red lines on top of the tracks depict SE genomic locations.
Figure 9B:
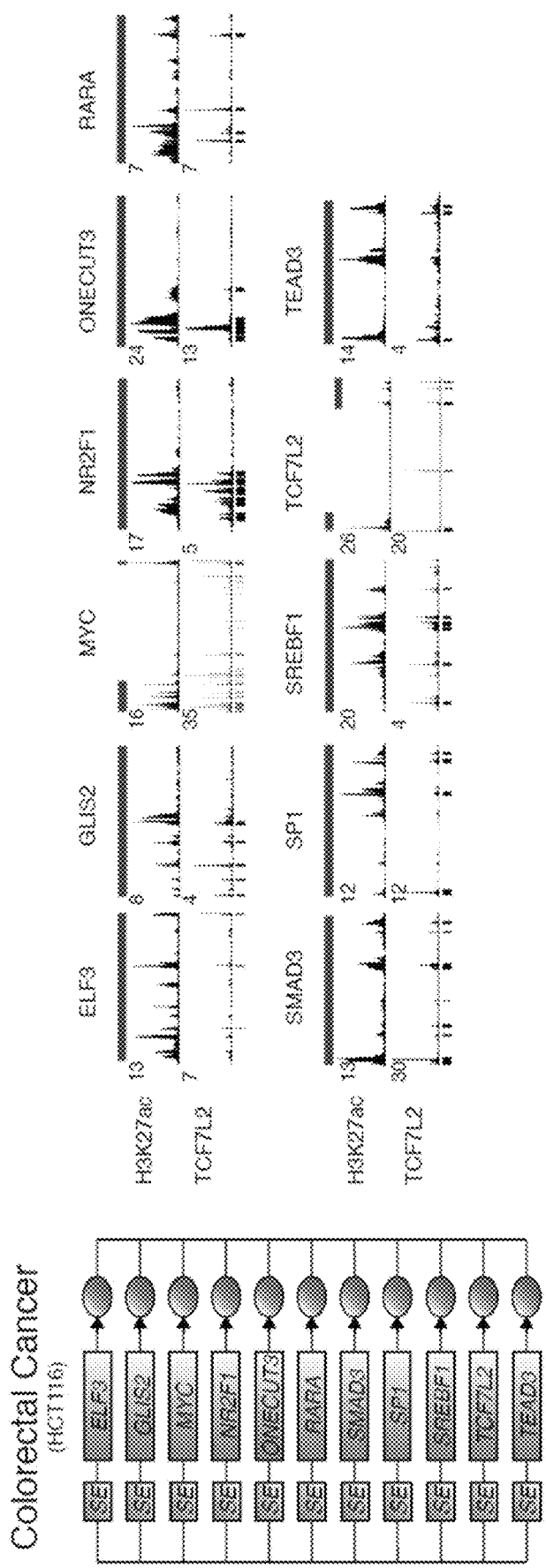
Figure 9C:
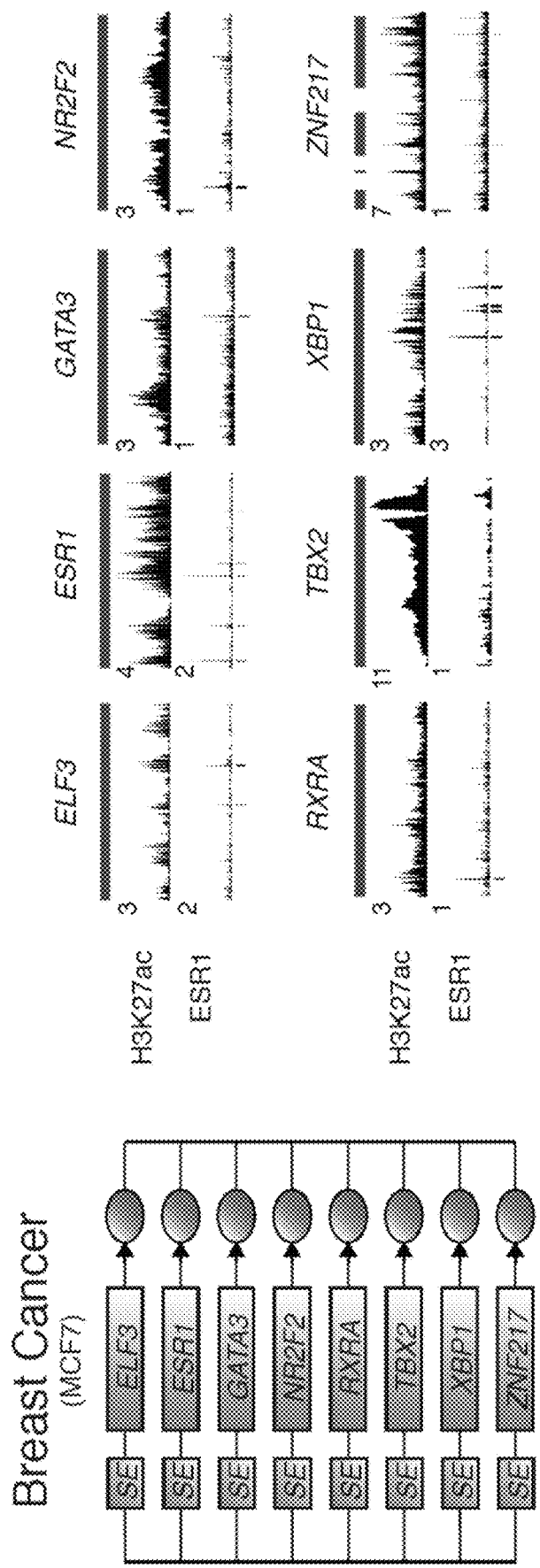

CRC (Ieda et al. 2010; Nam et al. 2014; Song et al. 2012), PDX1 in the pancreas CRC (Jonsson et al. 1994; Horb et al. 2003; Zhou et al. 2008), and SOX2 in the brain (hippocampus middle) CRC (Ferri 2004; Graham et al. 2003; Sisodiya et al. 2006; Lujan et al. 2012). They also contain well-characterized proto-oncogenes of cancer subtypes represented by cancer cell lines, such as ESR1 and GATA3 in MCF-7 breast cancer cells (Holst et al. 2007; Usary et al. 2004) and TCF7L2 and SMAD3 in HCT-116 colon cancer cells (Zhu et al. 1998; Tuupanen et al. 2009) (FIG. 9). Importantly, the approach described herein recapitulates the oncogenic circuitry that had been previously identified in T-cell Acute Lymphoblastic Leukemia (T-ALL) Jurkat cells (Sanda et al. 2012), as one of the CRC for Jurkat cells contains the four oncogenic TFs—GATA3, MYB, RUNX1 and TAL1—previously characterized as core TFs in this cell line (FIG. 4A). Together, these data indicate that the CRC models capture much existing knowledge of TFs that play key roles in control of cell identity across diverse cell and tissue types.

Figure 4B:
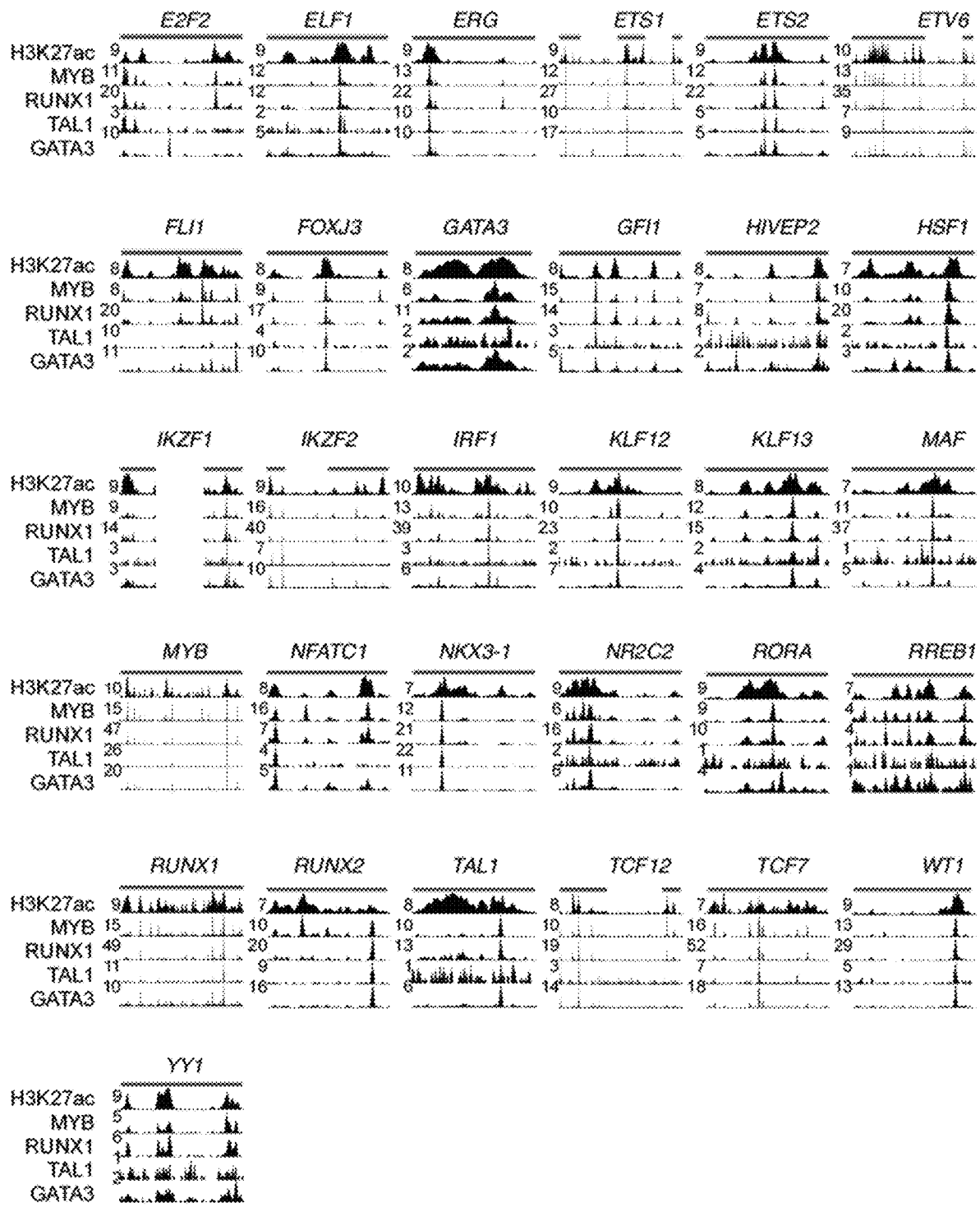
Figure 4C:
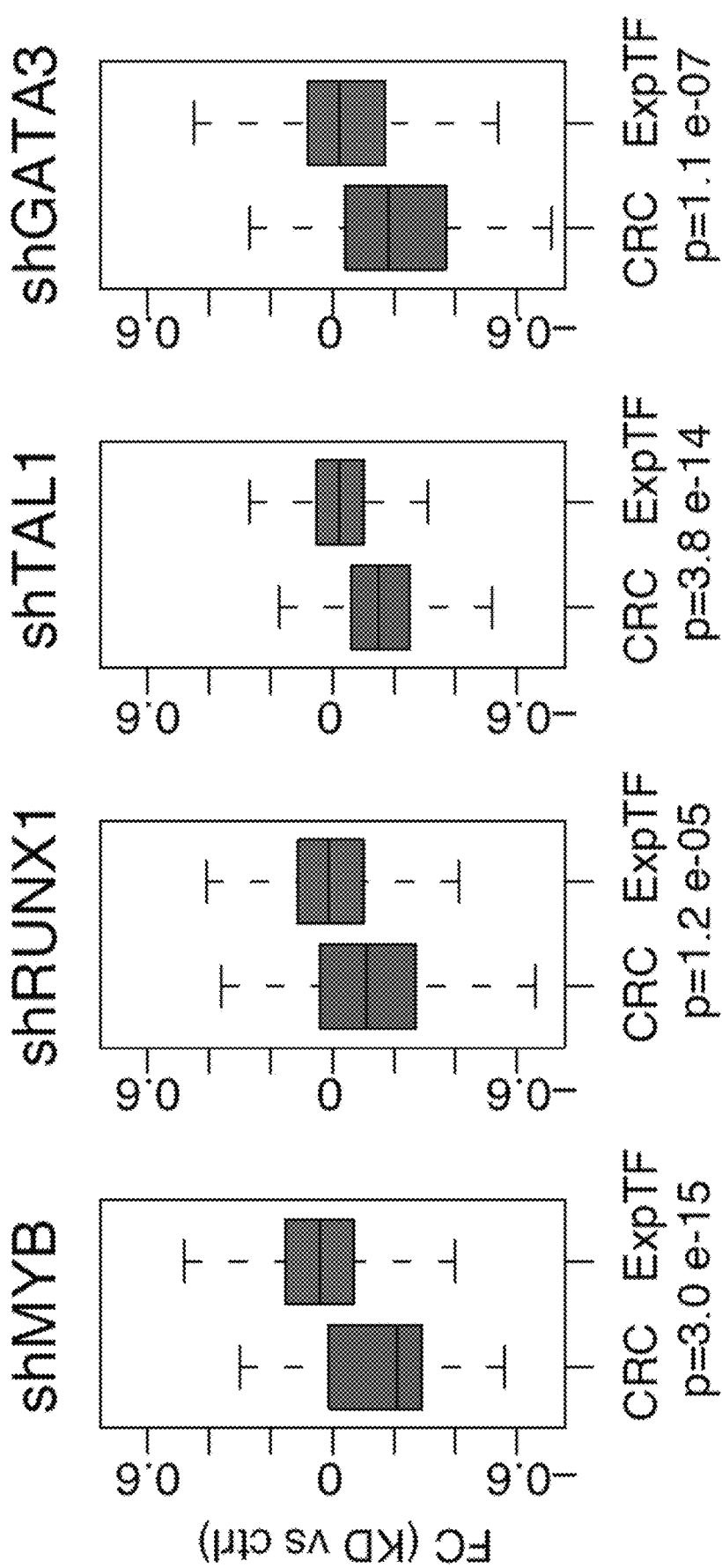

The present inventors used experimental data to test the accuracy of our predictions in newly identified CRCs. The binding of the core TFs to the super-enhancer sequences of the other predicted TFs in the core, is supported by ChIP-seq data for core TFs in T-ALL Jurkat cells (FIG. 4B). Available ChIP-seq data for TFs in the CRCs for other cell types were also analyzed and lend functional support for the predicted binding interactions in the CRCs (FIG. 9). To test the mutual regulation of the TFs in the core, we investigated the effects of shRNA depletion of MYB, RUNX1, TAL1 and GATA3 on expression of candidate core TF encoding genes in T-ALL Jurkat cells (FIG. 4C). Analysis of the data shows that when a core TF is depleted, the expression of the TFs in the core is significantly down-regulated compared to the set of TFs considered expressed in the cell. This observation is in agreement with a direct effect of the core TFs on the expression of the other TFs in the core.

Figure 5A:
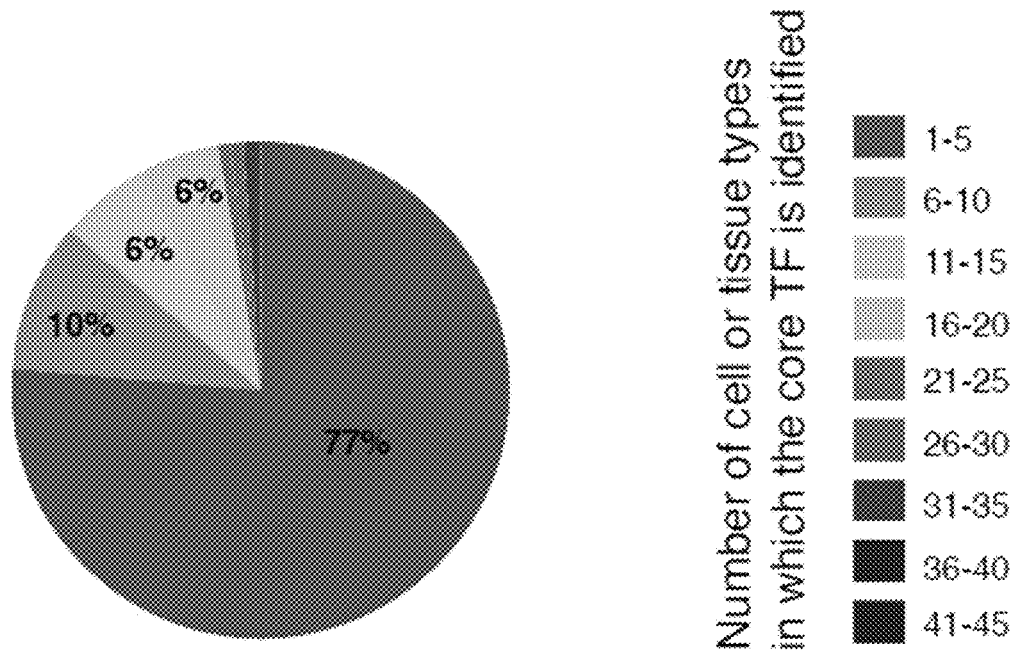
FIGS. 5A-5C present features of candidate core TFs.
Figure 5B:
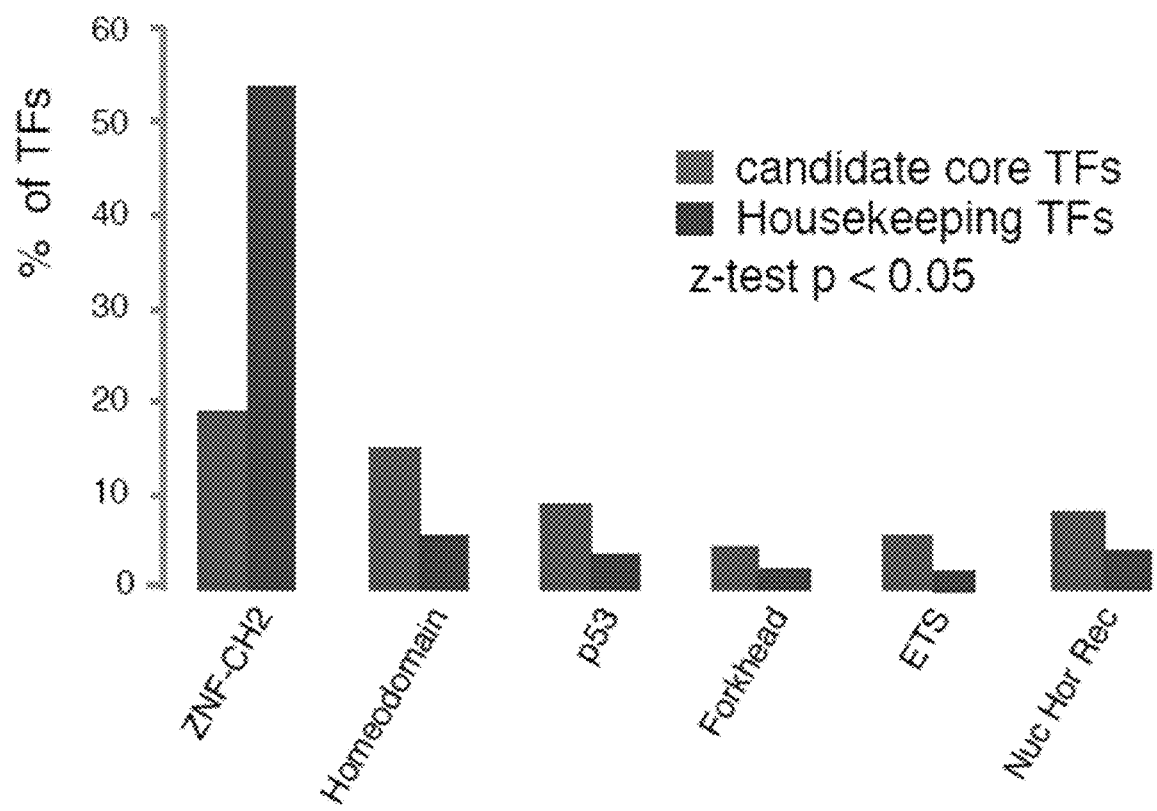
Figure 5C:
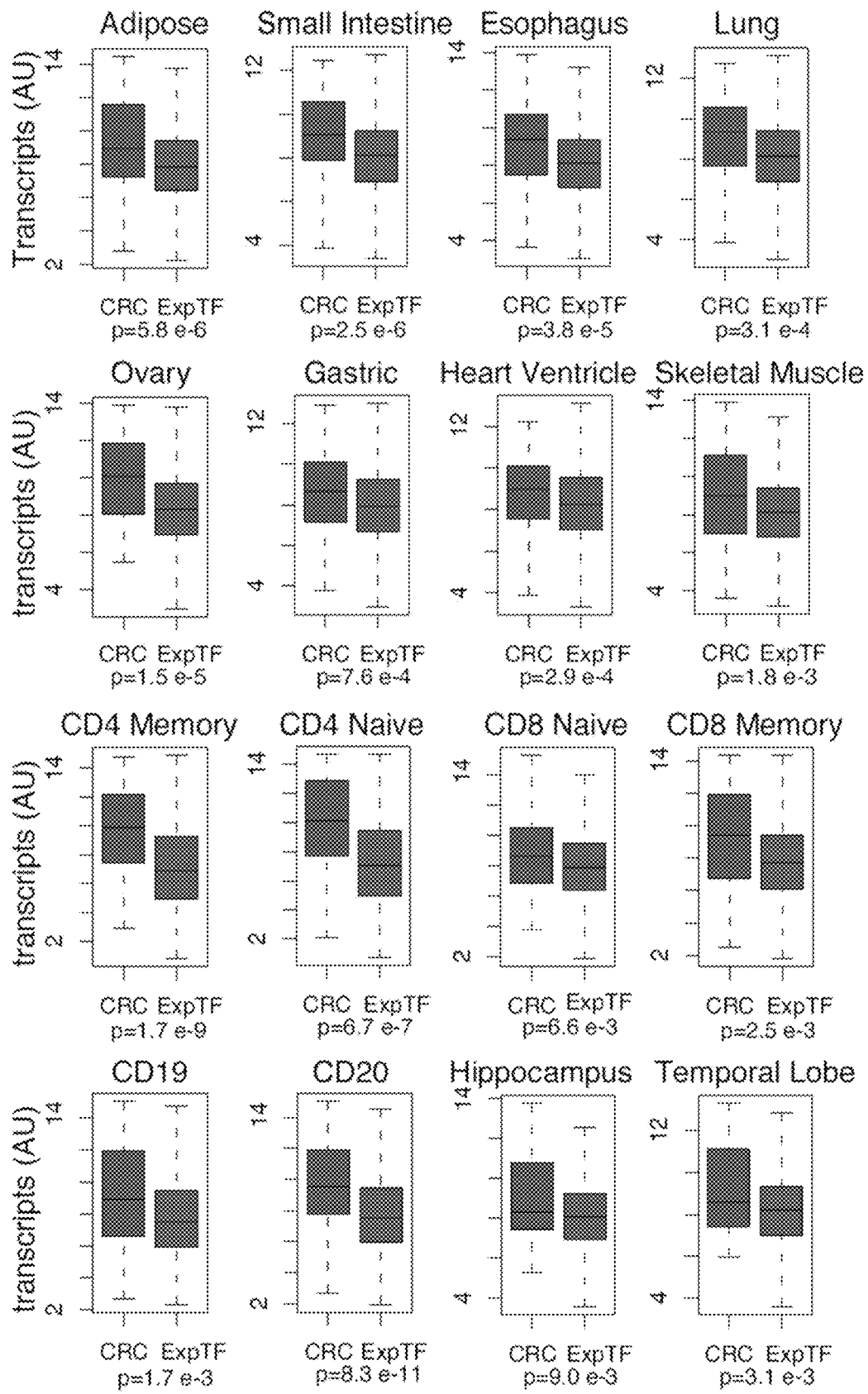

The candidate core TFs identified across a wide range of cell types show features of core TFs that have previously been described (Lee and Young 2013). Analysis of the candidate core TFs across samples shows that these are cell type specific or lineage specific: 34% of the core TFs identified across cell types are predicted to be core TFs in only one cell type, and 77% are predicted to be core TFs in less than 5 cell types (FIG. 5A). DNA-binding domain structures can provide insight on the functional roles of TFs (Vaquerizas et al., 2009), so the present inventors next compared the frequency of different DNA-binding domains in candidate core TFs to the one in ubiquitously expressed housekeeping TFs. Compared to housekeeping TFs, candidate core TFs are depleted in the most common type of TFs—zinc finger domain containing TFs—and enriched in various classes of TFs that have been associated with developmental processes, such as homeodomain-containing-TFs (FIG. 5B). Analysis of expression data shows that candidate core TFs exhibit higher transcript levels when compared to the full set of TFs considered expressed in the cell (FIG. 5C). The candidate core TFs are thus cell type or lineage specific, enriched for functional association with development processes, and show relatively high level of expression compared to other TFs expressed in the cell.

Figure 6A:
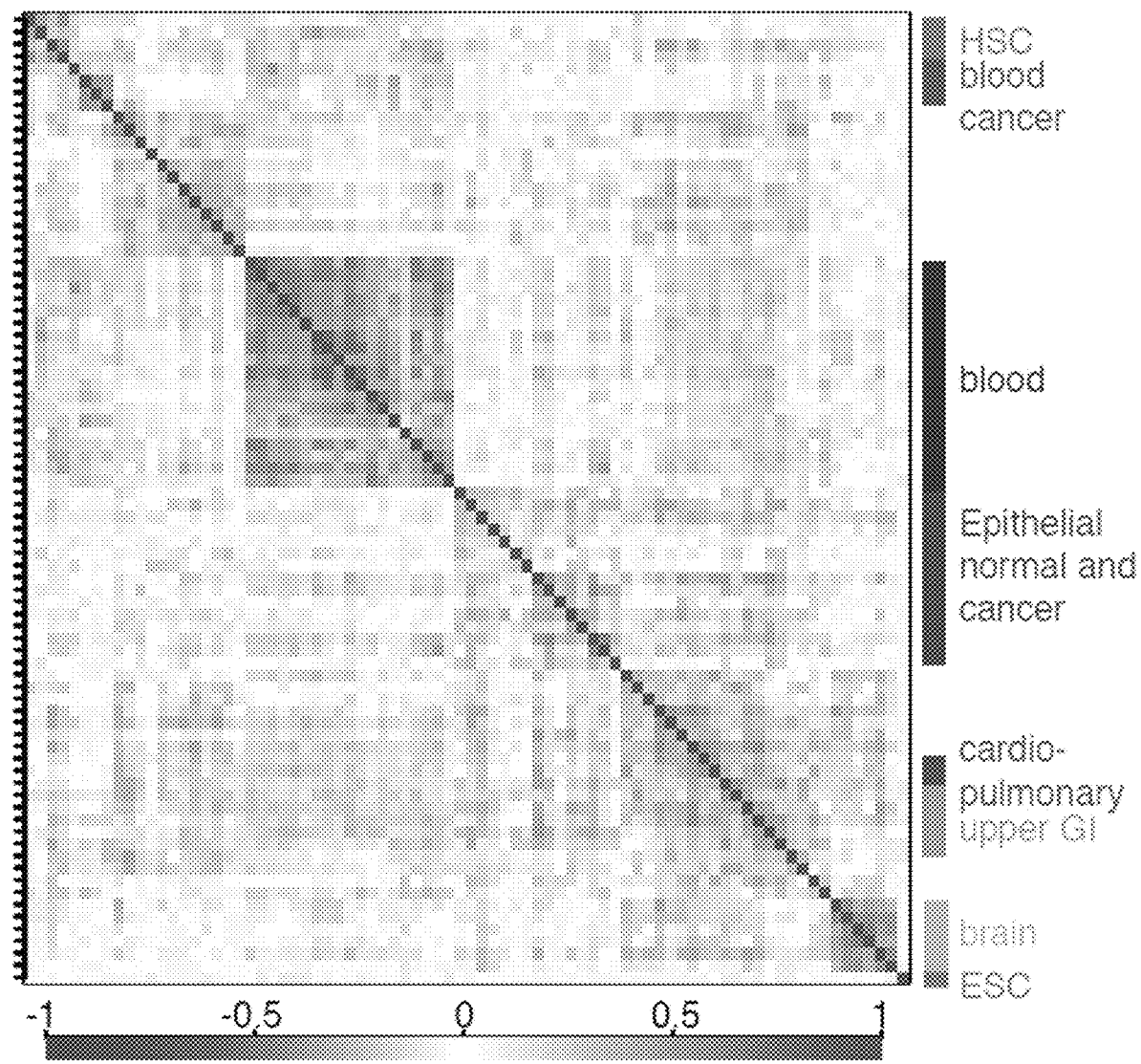
FIGS. 6A-6C present the properties of CRCs of multiple human cell and tissue types.
Figure 6B:
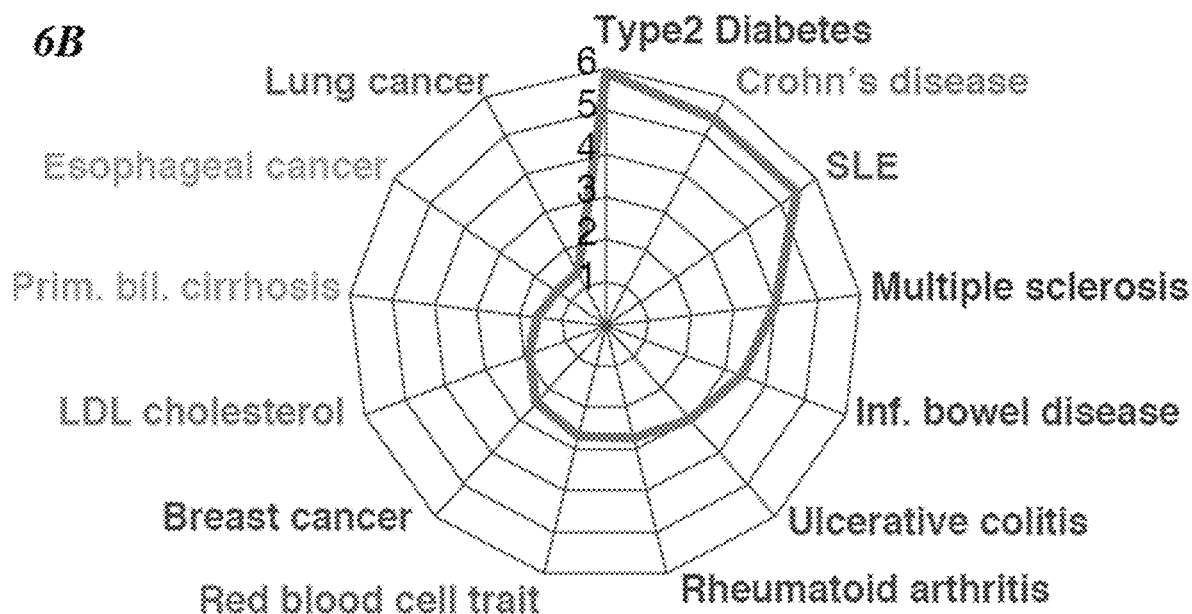
Figure 10:
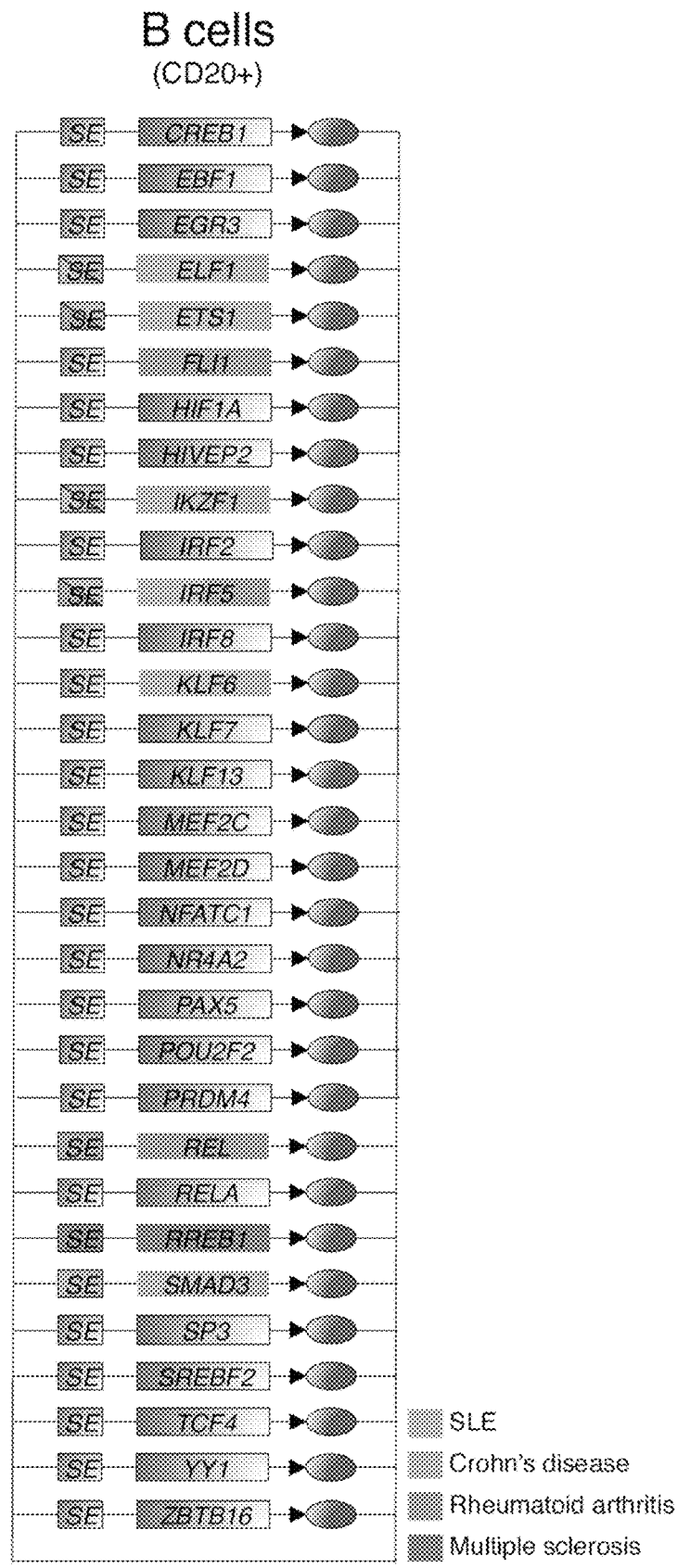
FIG. 10 depicts TF associated with the indicated diseases through GWAS in the CD20+ Bcell CRC model. Genes associated with a given disease through GWAS are colored according to the key. SEs that overlap SNPs associated with a given disease or trait through GWAS are colored according to the key.

Analyzing CRCs across cell types, the present inventors identified features of CRCs that should help guide further experiments to better understand the transcriptional pathways involved in development and disease. The present inventors observed that a substantial fraction of candidate core TFs is expressed in multiple cell types, typically within a lineage. This feature of shared core TFs within lineages is evident through hierarchical clustering of candidate core TFs across all datasets (FIG. 6A). It suggests that specific combinations of TFs may be required to control complementary aspects of cell identity and that circuitries may be rewired through ectopic expression of a few TFs between similar cell types. The present inventors also found that, compared to other TFs, candidate core TFs are found significantly more often in the set of genes associated with diseases or traits via Genome-Wide Association Studies (GWAS), which suggests their involvement in cell identity and disease development (see, FIG. 6B and FIG. 10). Previous studies have shown that disease-associated SNPs are enriched in SEs (Hnisz et al., 2013; Parker et al., 2013), and there are multiple examples of non-coding disease-associated SNPs overlapping the super-enhancers associated with TFs in the CRC (FIG. 10).

Figure 6C:
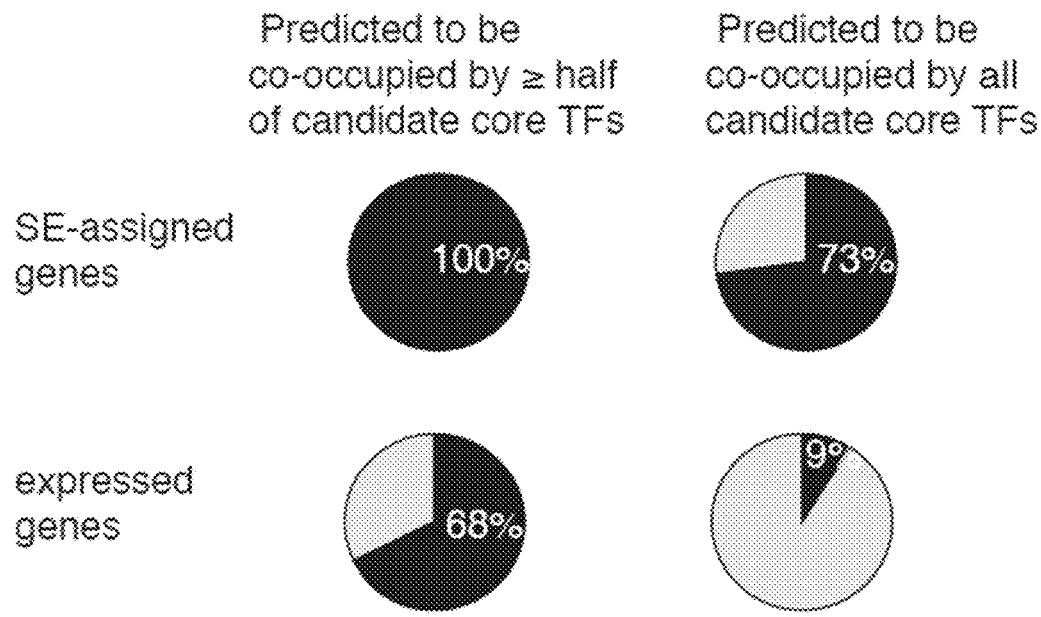

The present inventors also generated models of extended regulatory circuitry for 75 cell and tissue types using the same process described above for the hESC extended regulatory circuitry (FIG. 3). The features of these extended circuitries are consistent with those observed for hESCs. On average, across samples. 73% of the SE-assigned genes are predicted to be co-occupied by each of the candidate core TFs (FIG. 6C) and these SE-assigned target genes of the CRC play prominent roles in specific cell identities (FIG. 3).

Discussion

There have been tremendous advances in our understanding of the general mechanisms involved in control of gene transcription, but the pathways by which a small set of core TFs control gene expression programs have yet to be mapped in most cells. Described herein are models of core transcriptional regulatory circuitry for 75 human cell and tissue types. These models show significant percentages of overlap between the TF-TF binding interactions we predict in the CRCs and the TF-TF interactions identified in previous high-throughput analyses, for similar cell types (Neph et al. 2012) (see, Table 8, below). The CRC models provided include known core TFs and reprogramming TFs that have been previously identified in a few cell types, but add a large list of candidate cell identity regulators. These include ubiquitous and signaling TFs that should work together with the minimal set of TFs required to reprogram cells from one state to another, to establish and maintain cellular identity. These models provide the foundation for future studies of the transcriptional pathways that control cell identity in these diverse cell types of the human body.

Key target genes of the CRC were identified in a first step towards understanding how the information flows from the core TFs to all expressed genes. Across all cell and tissue types, the candidate core TFs were predicted to preferentially co-occupy SE-assigned genes, compared. to all expressed genes. As SE-assigned genes are typically key for cell identity, this shows that the concerted action of candidate core TFs may be preferentially targeted to those key cell identity genes. This led us to envision a model whereby the core TFs promote hallmarks of cell identities through co-binding the SEs of their own genes and regulating their own expression, and co-binding the SEs of many other genes important for cell identity and regulating their expression. The maps of CRC were thus extended to include the SE-assigned target genes of the CRC. These maps of extended regulatory circuitry are founding models for the description of more comprehensive networks that describe additional levels of regulation that should signaling pathways, as super-enhancers serve as integrating platforms for signaling (Hnisz et al. 2015; Siersbæk et al. 2014b).

The methods and processes presented herein constitute a first attempt to map CRC in a wide range of cell types and harbors several limitations that should be considered when using the data. The analyses were restricted to TFs that were assigned to a SE in the dataset, and for which DNA-binding motifs are available. The CRC models also rely on data derived from cell lines, which do not necessarily reflect the state of cells in their nominal niche, or from biopsies, which include mixed populations of cell types. Another consideration is the challenge of comprehensive experimental validation of the circuits, which would in principle require knock-out of individual core TFs and perhaps combinations of these TFs. Ongoing efforts to characterize DNA-binding motifs for TFs (Hume et al. 2015; Mathelier et al. 2014; Jolma et al. 2013), taking into account the influence of their TF partners, and the role of co-activators and chromatin regulators on their binding to regulatory sequences (Chen et al. 2008; Siersbæk et al. 2014a; Yan et al. 2013; Schmidt et al. 2015), and further experimental testing, should thus help refine the description of the CRC models we provide here.

CRC models should provide guidance for reprogramming studies and may prove valuable for better understanding transcriptional dysregulation in disease. Candidate core TFs are enriched in the genes associated with multiple diseases or traits through GWAS, supporting their role in disease development. Furthermore, SEs are hotspots of non-coding disease-associated sequence variants. Some of these variants may modify the binding sites for core TFs, providing a mechanism for disease-associated transcriptional misregulation. This is the case, for example, of TFs we predict in CRCs such as TAL1 in T cells, TBX5 in cardiac cells, TCF7L2 in colorectal cancer cells, and ESR1 and GATA3 in breast cancer cells (Bauer et al. 2013; van den Boogaard et al. 2012; Tuupanen et al. 2009; Sur et al. 2012; Cowper-Sal lari et al. 2012; French et al. 2013). Extended regulatory circuits integrating candidate core TFs and their SE-assigned target genes for many human cell types, may thus help better understand disease-associated genetic variation, leading someday to circuitry-directed therapeutic interventions.

EXPERIMENTAL PROCEDURES

ChIP-seq Data

H3K27ac ChIP-seq data were either downloaded from GEO (accession numbers in Table 1) or generously shared by the NIH Roadmap Epigenome project (Bernstein et al. 2010). ChIP-seq data for MYB (Mansour et al. 2014) and TAL1 (Palii et al. 2011) in Jurkat cells and for POU5F1 (Kunarso et al. 2010), SOX2 (Hawkins et al. 2011) and NANOG (Kunarso et al. 2010) in H1 hESC were downloaded from GEO. ChIP-seq data for CREB1, EBF, ELF1, ETS1, PAX5 and POU2F2 in GM12878 lymphoblastoid B cells, for TCF7L2 in HCT-116 colon cancer cell line, and for ESR4 in T-47D breast cancer cell line; were downloaded from ENCODE (Gertz et al. 2013).

CRC Mapper

The algorithm developed by the present inventors to identify core regulatory circuits (CRC) uses as input H3K27ac ChIP-seq reads aligned to the human genome, together with the ChIP-seq peaks identified by MACS, and the enhancer table output from ROSE (https://bitbucket.org/young_computation/rose) (Lovén et al. 2013). SEs identified with ROSE are assigned. to the closest transcript predicted to be expressed. For each SE-assigned TF, a motif analysis is carried out on the SE constituent sequences assigned to that TF using FIMO (Find Individual Motif Occurrences) from the MEME (Multiple Em for Motif Elicitation) suite (Matys et al. 2006) (Grant et al. 2011). A database of DNA sequence motifs for 695 TFs was compiled from the TRANSFAC database of motifs (Matys et al. 2006), and from the MEME suite (Jan. 23, 2014 update), for the following collections: JASPAR CORE 2014 vertebrates Waddler et al. 2014), Jolma 2013 (Jolma et al. 2013), Homeodomains (Berger et al. 2008), mouse UniPROBE (Robasky and Bulyk 2011) and mouse and human ETS factors (Wei et al. 2010). For the motif search, the search space in SEs is restricted to extended SE constituents, as these are the regions that capture most of the TE binding in SEs (FIG. 1C). SE constituent DNA sequences are extracted, extended on each side (500 bp by default), and used for motif search with FIMO with p-value threshold of $e^{-4}$. SE-assigned TFs whose set of constituents contains at least 3 DNA sequence motif instances for their own protein products are defined as autoregulated TFs. From the set of autoregulated TFs, the TFs predicted to bind to the SEs of other autoregulated TFs, using the same criteria as described above, are identified. All possible fully interconnected autoregulatory loops of TFs are then reconstructed through recursive identification. When multiple possibilities of fully interconnected autoregulatory loops are found, the most representative fully interconnected autoregulatory loop of TFs is selected as the model of CRC. This loop is defined as the loop containing the TFs that occur the most frequently across all possible loops.

Data Access

ChIP-seq data for H3K27Ac, RUNX1 and GATA3 in Jurkat cells can be found in GEO with accession numbers GSM1296384, GSM1697879 and GSM1697881, respectively. The CRC Mapper program is implemented in Python and is freely available for download on bitbucket.org/young_computation/CRCmapper.

Identification of H3K27ac ChIP-seg Peaks and Super-Enhancers

Among the possibilities of ChIP-seq data for SE identification, H3K27ac ChIP-seq data was used here, because this chromatin mark is specifically associated with active enhancers (Creyghton et al. 2010) and is available for a wide collection of samples. Sequence reads were aligned to the hg19 version of the human genome using Bowtie (Langmead et al. 2009) with parameters –k1–k1—best. H3K27ac enriched regions were called using MACS 1.4.2 (Zhang et al. 2008) with parameters –p 1e–9 keep-dup=auto–w–S–space=50. ROSE (https://bitbucket.org/young_computation/rose) (Lovén et al. 2013) was then used to identify SEs from the H3K27ac enriched regions as described (Hnisz et al. 2013). Briefly, H3K27ac enriched regions were considered as constituent enhancers and were stitched together when they occurred within 12.5kb. In order to distinguish the H3K27ac enhancer signal from the H3K27ac promoter signal, constituent enhancers that were fully contained within +/−1kb of a RefSeq Transcription Start Site (TSS) were disregarded for stitching. Enhancer clusters that had a H3K27ac input-subtracted signal above a computed threshold defined by ranking the H3K27ac signal at enhancer clusters were identified as SEs.

CRC Mapper

SE to Gene Assignment

SEs identified with ROSE (https://bitbucket.org/young_computation/rose) (Lovén et al. 2013) are assigned to the closest transcript predicted to be expressed, where distance is measured as the distance from the center of the SE to the TSS. As expression data does not exist for all cell types examined, H3K27ac read density is used to determine expression in each sample, H3K27ac read. density in the region +/−1 kb around the TSS is used to rank each transcript in each sample. Transcripts on this ranked list are then assigned to genes. Duplicates from the resulting ranked gene list are removed and the list is subsequently used to identify the top ⅔ of ranked genes. The read density value corresponding to the last gene in the top ⅔ is used as a threshold value that can then be applied back to identify all transcripts considered expressed. The selection of top ⅔ as a threshold is based on the observation that this threshold allows recovery of the highest percentage of expressed genes while minimizing false negatives, when the results of this method are compared to microarray and RNA-seq data in H1 ESC. This ratio of expressed genes is consistent with the ratio of genes considered expressed across cell types (Ramsköld et al. 2009).

Identification of Candidate Core TFs

SE-assigned transcription factors (TF) are then selected from the lists of SE-assigned genes using a list of 1253 TFs consisting of the intersection of AnimalTFDB (Zhang et al. 2012) and TcoF (Schaefer et al. 2011) lists of TFs minus CTCF, GTF2I and GTF2IRD1 that are not considered as putative core TFs (Table 2, below).

Motif Analysis

A database of DNA sequence motifs for 695 TFs—about 60% of known TFs in vertebrates—was compiled from the TRANSFAC database of motifs (Matys et al. 2006), and from the MEME suite (Jan. 23, 2014 update), for the following collections: JASPAR CORE 2014 vertebrates (Mathelier et al. 2014), Jolma 2013 (Jolma et al. 2013), Homeodomains (Berger et al. 2008), mouse UniPROBE (Robasky and Bulyk 2011) and mouse and human ETS factors (Wei et al. 2010). For SE-assigned TFs with identified sequence specific binding motifs, those motifs are used to search the SE sequences assigned to the gene encoding that TF. For the motif search, the search space in SEs is restricted to extended SE constituents, as these are the regions that capture most of the TF binding in SEs (FIG. 1C). SE constituent DNA sequences are extracted, extended on each side (500 bp by default) and used for motif search with FIMO (Grant et al. 2011) with p-value threshold of 1e−4 and a set of background sequences generated from the set of extended constituent sequences with fasta-getmarkov.

Identification of Fully Interconnected Auto-Regulatory Loops

SE-assigned TFs whose set of constituents contains at least 3 DNA sequence motif instances for their own protein products are defined as autoregulated TFs. If multiple motifs for the same TF matched an identical location, it is counted as only one motif instance. From the set of autoregulated TFs, the TFs predicted to bind to the SEs of other autoregulated TFs, using the same criteria as described above, are identified and all possible fully interconnected autoregulatory loops of TFs are then reconstructed through recursive identification. When multiple possibilities of fully interconnected autoregulatory loops are identified, the most representative fully interconnected autoregulatory loop of TFs is selected as the model of CRC. This loop is defined as the loop containing the TFs that occur the most frequently across all possible loops.

Metagenes

Genome-wide meta-representations of ChIP-seq density (in units of reads per million per base pair) were created by mapping aligned reads to SE constituents +/−5 kb using bamToGFF (github.com/bradnerComputation/pipeline/blob/master/bamToGFF.py) (Lin et al. 2012).

Transcription Factor Binding Analysis

H1 hESC ChIP-seq data (Kunarso et al. 2010; Hawkins et al. 2011) were used to quantify the binding of TFs to the region +/−1 kb around cognate motifs found in SE constituents which are extended 500 bp on each side, or, as a control, in the same number of randomly selected genomic regions of the same size. The number of sequences containing motifs that overlapped with the ChIP-seq peaks identified by MACS 1.4.2 (Zhang et al. 2008) ran with parameter −p 1e−9 keep-dup=auto −w−S−space=50 were quantified. The true positive rates of TF binding was calculated by dividing the number of motif containing sequences that were bound by the TF from the ChIP-seq data analysis, over the total number of motif containing sequences.

Gene Set Enrichment Analysis (GSEA)

GSEA (Mootha et al., 2003) analyses were performed using the tool available at broadinstitute.org/gsea/. Mean z-scores for either OCT4-GFP protein level reduction or cell nuclei count reduction (Chia et al. 2010) were used to rank the lists of all TFs and H1 hESC candidate core TFs were used as the query. The Pre-Ranked function of the GSEA software was used with 1000 iterations to generate the plots.

CRC Target Gene Analysis

For the CRC target gene analysis, two groups of target genes were considered: expressed genes and SE-assigned genes. Expressed genes correspond to the top ⅔ genes ranked based on H3K27ac signal in the region +/−1 kb around the TSS. SE-assigned genes were identified from the list of expressed genes as described above. For H1, in each group, genes that had motif instances predicting the binding of at least 5, 6, 7, 8, 9 or 10 candidate core TFs in their combined enhancer and promoter sequences were quantified. For other cell types, genes that had motif instances predicting the binding of at least half or all candidate core TFs in their combined enhancer and promoter sequences were quantified. The region +/−1 kb around the TSS and associated super or typical enhancer constituents extended 500 bp on each side were used for the motif search when all expressed genes were considered, and SE constituents extended 500 bp on each side and corresponding region +/−1 kb around the TSS sequence of the SE-assigned gene were used for the motif search when SE assigned genes were considered. For the maps in FIG. 3, 30 target genes selected from the CRC targets are displayed as examples. These were selected based on the number of Pubmed literature entries for each target gene associated to search terms relative to the cell type in which it was identified.

ChIP-seq Tracks

Sequence reads were aligned to the 419 version of the human genome using Bowtie (Langmead et al. 2009) with parameters −k1−m1—best. Wiggle tracks were created from ChIP-seq data with MACS 1.4.2 (Zhang et al. 2008) with parameters −p 1e−9 keepdup=auto−w−S−space=50, normalized to the total number of mapped reads in the sample, and visualized in UCSC Genome Browser.

ChIP-seq

Chomatin immunoprecipitation experiments were performed in Jurkat cells (ATCC), as described (Kwiatkowski et al. 2014), with the following antibodies: anti-H3K27ac (ab4729, Abcam), anti-RUNX1 (ab23980. Abeam) and anti-GATA3 (Sc-22206X, Santa Cruz). Purified immunoprecipitated DNA was prepared for sequencing according to a modified version of the Solexa Genomic DNA protocol, and sequenced with an Illumina HiSeq sequencer.

Microarray Expression Analysis

Microarray data displayed on FIG. 5 were downloaded from GEO (references in Table 1). Expression values were processed using MASS normalization from the "affy" R package (Gautier et al. 2004). Signals for probes corresponding to the same transcript were aggregated using the standard probe assignment method (hgu133plus2cdf"). Normalized log2(expression+1) of the transcripts for the set of candidate core TFs or for all TFs considered expressed with the metric described above, are displayed for each sample. P-values were calculated using a Wilcoxon test. Affymetrix HG U133 2.0 plus microarray data performed in Jurkat cells after knock-down of either MYB, RUNX1, TAL1 and GATA3 with shRNAs were downloaded from Salida et al., 2011. Mean of log 2 foldchange (knock-down/control) for two biological replicates using two target shRNAs per TF and two shRNAs control were extracted for either the set of Jurkat cell candidate core TFs represented on FIG. 4A or for the full set of TFs considered expressed in Jurkat cells.

DNA-Binding Domain Structure Analysis

Candidate core TFs for all samples, and the compiled list of housekeeping TFs (Ramsköld et al. 2009) considered expressed in at least one of the samples, were overlapped with lists of TFs classified by DNA-binding domains (Vaquerizas et al. 2009). Percentages of DNA-binding domain containing TFs were compared between candidate core TFs and housekeeping TFs for each type of DNA-binding domain. Percentages of TFs that were significantly different between the two groups of TFs are displayed (z-test p-value<5e-2).

Hierarchical Clustering of CRCs

A matrix of distances was calculated based on Pearson correlations between the candidate core TFs lists and plotted using R. For this analysis, we required the samples had greater than 7 TFs in their CRC for improved robustness of clustering.

Disease or Trait-Associated Gene Analysis

Disease or trait-associated gene lists were downloaded from the NEGRI catalog of published Genome-Wide Association Studies (Dec. 5, 2015 update). The disease or trait associated genes overlapping with the list of core or non-core TFs were quantified. For each disease or trait, the proportion of the overlapping candidate core TFs and non-core TFs were compared with a z-test. The disease or traits for which z-test p-value<$5^{e-2}$, are displayed and -log(p-values) values are plotted on the radar plot.

Comparison of Networks

For the set of TFs in the CRC that are represented in the transcriptional network for a corresponding cell type (Neph et al. 2012), we extracted the set of TF-TF interactions predicted in the CRC, where interactions are defined as predicted TF binding to the regulatory sequences of another TF. We then computed the number of TF-TF interactions predicted in the CRC which are also predicted in the transcriptional network for a corresponding cell type (Neph et al. 2012). As a control, we did the same analysis, for each sample, using a set of the same number of randomly selected TFs that are not part of the CRC, but that are represented in the network for a corresponding cell type (Neph et al. 2012). We then compared the percentage of overlap obtained for the CRC set of interactions, with the percentage of overlap obtained for the control set of interactions, with a z-test.

REFERENCES

Adelman K, Lis J T. 2012. Promoter-proximal pausing of RNA polymerase II: emerging roles in metazoans, *Nat Rev Genet* 13: 720-31.

Alon U. 2007. Network motifs: theory and experimental approaches. *Nat Rev Genet* 8: 450-61.

Avilion A A, Nicolis S K, Pevny L H, Perez L, Vivian N, Lovell-Badge R. 2003. Multipotent cell lineages in early mouse development depend on SOX2 function. *Genes Dev* 17: 126-40.

Bar-Joseph Z, Gerber G K, Lee T I, Rinaldi N J, Yoo J Y, Robert F, Gordon D B, Fraenkel E, Jaakkola T S, Young R A, et al. 2003. Computational discovery of gene modules and regulatory networks. *Nat Biotechnol* 21: 133742.

Barnea E, Bergman Y. 2000. Synergy of SF1 and RAR in activation of Oct-3/4 promoter, *J Biol Chem* 275: 6608-19, Bauer D E, Kamran S C, Lessard S, Xu J, Fujiwara Y, Lin C, Shao Z, Canner M C, Smith E C, Pinello L, et al. 2013. An erythroid enhancer of BCL11A subject to genetic variation determines fetal hemoglobin level. *Science* 342: 253-7.

Berger M F, Badis G, Gehrke A R, Talukder S, Philippakis A A, Peña-Castillo L, Alleyne T M, Mnaimneh S, Botvinnik O B, Chan E T, et al. 2008. Variation in homeodomain DNA binding revealed by high-resolution analysis of sequence preferences. *Cell* 133: 1266-76.

Bernstein B E, Stamatoyannopoulos J A, Costello J F, Ren B, Milosavljevic A, Meissner A, Kellis M, Marra M A, Beaudet A L, Ecker J R, et al. 2010. The NIH Roadmap Epigenomics Mapping Consortium. *Nat Biotechnol* 28: 1045-8.

Bonasio R, Tu S, Reinberg D. 2010. Molecular signals of epigenetic states. *Science* 330: 612-6.

Boyer L A, Lee T I, Cole M F, Johnstone S E, Levine S S, Zucker J P, Guenther M G, Kumar R M, Murray H L, Jenner R G, et al. 2005. Core transcriptional regulatory circuitry in human embryonic stem cells, *Cell* 122: 947-56.

Buganim Y, Faddah D A, Jaenisch R. 2013. Mechanisms and models of somatic cell reprogramming. *Nat Rev Genet* 14: 427-39.

Catena R, Tiveron C, Ronchi A, Porta S, Ferri A, Tatangelo L, Cavallaro M, Favaro R, Ottolenghi S, Reinhold R, et al. 2004. Conserved POU binding DNA sites in the Sox2 upstream enhancer regulate gene expression in embryonic and neural stem cells. *J Biol Chem* 279: 41846-57.

Chambers I, Colby D, Robertson M, Nichols J, Lee S, Tweedie S, Smith A. 2003. Functional expression cloning of Nanog, a pluripotency sustaining factor in embryonic stem cells. *Cell* 113: 643-55.

Chapuy B, McKeown M R, Lin C Y, Monti S, Roemer M G M, Qi J, Rahl P B, Sun H H, Yeda K T, Doench J G, et al. 2013. Discovery and characterization of super-enhancer-associated dependencies in diffuse large B cell lymphoma. *Cancer Cell* 24: 777-90.

Cheasley D, Pereira L, Lightowler S, Vincan E, Malaterre J, Ramsay R G, 2011. Myb controls intestinal stem cell genes and self-renewal. *Stem Cells* 29: 2042-50.

Chen X, Vega V B, Ng H-H. 2008. Transcriptional regulatory networks in embryonic stem cells. *Cold Spring Harb Symp Quant Biol* 73: 203-9.

Chew J-L, Loh Y-H, Zhang W, Chen X, Tam W-L, Yeap L-S, Li P, Ang Y-S, Lim B, Robson P, et al. 2005. Reciprocal transcriptional regulation of Pou5f1 and Sox2 via the Oct4/Sox2 complex in embryonic stem cells. *Mol Cell Biol* 25: 6031-46.

Chia N-Y, Chan Y-S, Feng B, Lu X, Orlov Y L, Moreau D, Kumar P, Yang L, Jiang J, Lau M-S, et al. 2010. A genome-wide RNAi screen reveals determinants of human embryonic stem cell identity. *Nature* 468: 316-20.

Conaway R C, Conaway J W. 2011. Origins and activity of the Mediator complex. *Semin Cell Dev Biol* 22: 729-34.

Corradin O, Saiakhova A, Akhtar-Zaidi B, Myeroff L, Willis J, Cowper-Sal lari R, Lupien M, Markowitz S. Scacheri P C. 2014. Combinatorial effects of multiple enhancer variants in linkage disequilibrium dictate levels of gene expression to confer susceptibility to common traits. *Genome Res* 24: 1-13.

Cowper-Sal lari R, Zhang X, Wright J B, Bailey S D, Cole M D, Eeckhoute J, Moore J H, Lupien M. 2012. Breast cancer risk-associated SNPs modulate the affinity of chromatin for FOXA1 and alter gene expression. *Nat Genet* 44: 1191-8.

Davidson E H. 2010. Emerging properties of animal gene regulatory networks. *Nature* 468: 911-20.

De Wit E, Bouwman B A M, Zhu Y, Klous P, Splinter E, Verstegen M J A M, Krijger P H L, Festuccia N, Nora E P, Welling M, et al. 2013. The pluripotent genome in three dimensions is shaped around pluripotency factors. *Nature* 501: 227-31.

Declercq J, Sheshadri P, Verfaillie C M, Kumar A. 2013. Zic3 enhances the generation of mouse induced pluripotent stem cells. *Stem Cells Dev* 22: 2017-25.

Dixon J R, Jung I, Selvaraj S, Shen Y, Antosiewicz-Bourget J E, Lee A Y, Ye Z, Kim A, Rajagopal N, Xie W, et al. 2015. Chromatin architecture reorganization during stem cell differentiation. *Nature* 518: 331-336, Doulatov S, Vo L T, Chou S S, Kim P G, Arora N, Li H, Hadland B K, Bernstein I D, Collins J J, Zon L I, et al. 2013. Induction of multipotential hematopoietic progenitors from human pluripotent stem cells via respecification of lineage-restricted precursors. *Cell Stem Cell* 13: 459-70.

Dowen J M, Fan Z P, Hnisz D, Ren G, Abraham. B J, Zhang L N, Weintraub A S, Schuijers J, Lee T I, Zhao K, et al. 2014. Control of Cell Identity Genes Occurs in Insulated Neighborhoods in Mammalian Chromosomes, *Cell* 159: 374-387.

Dutkowski J, Kramer M, Surma M A, Balakrishnan R, Cherry J M, Krogan N J, Ideker T. 2013. A gene ontology inferred from molecular networks. *Nat Biotechnol* 31: 38-45.

Farh K K-H, Marson A, Zhu J, Kleinewietfeld M, Housley W J, Beik S, Shoresh N, Whitton H, Ryan R J H, Shishkin A A, et al. 2014. Genetic and epigenetic fine mapping of causal autoimmune disease variants. *Nature*.

Ferri A L M. 2004. Sox2 deficiency causes neurodegeneration and impaired neurogenesis in the adult mouse brain. *Development* 131: 3805-3819.

French J D, Ghoussaini M, Edwards S L, Meyer K B, Michailidou K, Ahmed S, Khan S, Maranian M J, O'Reilly M, Hillman K M, et al. 2013. Functional variants at the 11q13 risk locus for breast cancer regulate cyclin D1 expression through long-range enhancers, *Am J Hum Genet* 92: 489-503.

Gerstein M B, Kundaje A, Hariharan M, Landt S G, Yan K-K, Cheng C, Mu X J, Khurana E, Rozowsky J, Alexander R, et al. 2012. Architecture of the human regulatory network derived from ENCODE data. *Nature* 489: 91-100.

Gertz J. Savic D, Varley K E, Partridge E C, Safi A, Jain P, Cooper G M, Reddy T E, Crawford G E, Myers R M. 2013. Distinct properties of cell-type-specific and shared transcription factor binding sites. *Mol Cell* 52: 25-36.

Gifford C A, Ziller M J, Gu H, Trapnell C, Donaghey J, Tsankov A, Shalek A K, Kelley D R, Shishkin A A, Issner R, et al. 2013. Transcriptional and epigenetic dynamics during specification of human embryonic stem cells. *Cell* 153: 1149-63.

Graf T, Enver T. 2009. Forcing cells to change lineages. *Nature* 462: 587-94.

Graham V, Khudyakov J, Ellis P, Pevny L. 2003. SOX2 functions to maintain neural progenitor identity. *Neuron* 39: 749-65.

Grant C E, Bailey T L, Noble W S. 2011, FIMO: scanning for occurrences of a given motif. *Bioinformatics* 27: 1017-8.

Guo G, Smith A. 2010. A genome-wide screen in EpiSCs identifies Nr5a nuclear receptors as potent inducers of ground state pluripotency. *Development* 137: 3185-92.

Hawkins R D, Hon G C, Yang C, Antosiewicz-Bourget J E, Lee L K, Ngo Q-M, Klugman S, Ching K A, Edsall L E, Ye Z, et al. 2011. Dynamic chromatin states in human ES cells reveal potential regulatory sequences and genes involved in pluripotency. *Cell Res* 21: 1393-409.

Hnisz D, Abraham B J, Lee T I, Lau A, Saint-André V, Sigova A a, Hoke H a, Young R a. 2013. Super-enhancers in the control of cell identity and disease. *Cell* 155: 934-47.

Hnisz D, Schuijers J, Lin C Y, Weintraub A S, Abraham B J, Lee T I, Bradner J E, Young R A. 2015. Convergence of Developmental and Oncogenic Signaling Pathways at Transcriptional Super-Enhancers. *Mol Cell* 58: 362-70.

Hoist F, Stahl P R, Ruiz C, Hellwinkel O, Jehan Z, Wendland M, Lebeau A, Terracciano L, Al-Kuraya K, Jänicke F, et al. 2007. Estrogen receptor alpha (ESR1) gene amplification is frequent in breast cancer. *Nat Genet* 39: 655-60.

Herb M E, Shen C N, Tosh D, Slack J M W. 2003. Experimental conversion of liver to pancreas. *Curr Biol* 13: 105-15.

Hume M A, Barrera L A, Gisselbrecht S S, Bulyk M L. 2015. UniPROBE, update 2015: new tools and content for the online database of protein-binding microarray data on protein-DNA interactions. *Nucleic Acids Res* 43: D117-22.

Ieda M, Fu J-D, Delgado-Olguin P, Vedantham V, Hayashi Y, Bruneau B G, Srivastava D. 2010. Direct reprogramming of fibroblasts into functional cardiomyocytes by defined factors. *Cell* 142: 375-86.

Jaenisch R, Young R. 2008, Stem cells, the molecular circuitry of pluripotency and nuclear reprogramming. *Cell* 1.32: 567-82.

Jolma A, Yan J, Whitington T, Toivonen J, Nitta K R, Rastas P, Morgunova E, Enge M, Taipale M, Wei G, et al. 2013. DNA-binding specificities of human transcription factors. *Cell* 152: 327-39.

Jonsson J, Carlsson L, Edlund T, Edlund H. 1994. Insulin-promoter-factor 1 is required for pancreas development in mice. *Nature* 371: 606-9.

Kagey M H, Newman J J, Bilodeau S, Zhan Y, Orlando D A, van Berkum N L, Ebmeier C C, Goossens J, Rahl P B, Levine S S, et al. 2010. Mediator and cohesin connect gene expression and chromatin architecture. *Nature* 467: 430-5.

Kanehisa M, Goto S, Sato Y, Furumichi M, Tanabe M. 2012. KEGG for integration and interpretation of large-scale molecular data sets. *Nucleic Acids Res* 40: D109-14.

Kemmeren P, Sameith K, van de Pasch L A L, Benschop J J, Lenstra T L, Margaritis T, O, Duibhir E, Apweiler E, van Wageningen S, Ko C W, et al. 2014. Large-scale genetic perturbations reveal regulatory networks and an abundance of gene-specific repressors. *Cell* 157: 740-52.

Kertesz M, Iovino N, Unnerstall U, Gaul U, Segal E. 2007. The role of site accessibility microRNA target recognition. *Nat Genet* 39: 1278-84.

Krebs H A. 1940. The citric acid cycle and the Szent-CyÖrgyi cycle in pigeon breast muscle. *Biochem J* 34: 775-9.

Kumar R M, Cahan P, Shalek A K, Satija R, Jay Daley Keyser A, Li H, Zhang J, Pardee K, Gennert D, Trombetta J J, et al. 2014. Deconstructing transcriptional heterogeneity in pluripotent stem cells. *Nature* 516: 56-61.

Kunarso G, Chia N-Y, Jeyakani J, Hwang C, Lu X, Chan Y-S, Ng H-H, Bourque G. 2010. Transposable elements have rewired the core regulatory network of human embryonic stem cells. *Nat Genet* 42: 631-4.

Kuroda T, Tada M, Kubota H, Kimura H, Hatano S, Suemori H, Nakatsuji N, Tada T. 2005. Octamer and Sox elements are required for transcriptional cis regulation of Nanog gene expression. *Mol Cell Biol* 25: 2475-85.

Kuzimichev A N, Kim S-K, D'Alessio A C, Chenoweth J G, Wittko I M, Campanati L, McKay R D. 2012. Sox2 acts through Sox21 to regulate transcription in pluripotent and differentiated cells. *Curr Biol* 22: 1705-10.

Lee T I, Rinaldi N J, Robert F. Odom D T, Bar-Joseph Z, Gerber G K, Hannett N M, Harbison C T, Thompson C M, Simon I, et al. 2002. Transcriptional regulatory networks in *Saccharomyces cerevisiae. Science* 298: 799-804.

Lee T I, Young R A. 2013. Transcriptional regulation and its misregulation in disease. *Cell* 152: 1237-51.

Lefebvre C, Rajbhandari P, Alvarez M J, Bandaru P, Lim W K, Sato M, Wang K, Sumazin P, Kustagi M. Bisikirska B C, et al. 2010. A human B-cell interactome identifies MYB and FOXM1 as master regulators of proliferation in germinal centers. *Mol Syst Biol* 6: 377.

Levine M, Cattoglio C, Tjian R. 2014. Looping back to leap forward: transcription enters a new era. *Cell* 157: 13-25.

Lewis B P, Burge C B, Bartel D P. 2005. Conserved seed pairing, often flanked by adenosines, indicates that thousands of human genes are microRNA targets. *Cell* 120: 15-20.

Li Y, Lv Z, He G, Wang J, Zhang X, Lu G, Ren X, Wang F, Zhu. X, Ding Y, et al. 2015. The SOX17/miR-371-5p/SOX2 axis inhibits EMT, stem cell properties and metastasis in colorectal cancer. *Oncotarget* 6: 9099-9112.

Lieu Y K, Reddy E P. 2009. Conditional c-myb knockout in adult hematopoietic stem cells leads to loss of self-renewal due to impaired proliferation and accelerated differentiation, *Proc Natl Acad Sci U S A* 106: 21689-94.

Lim L S, Loh Y-H, Zhang W, Li Y, Chen X, Wang Y, Bakre M, Ng H-H, Stanton L W. 2007, Zic3 is required for maintenance of pluripotency in embryonic stem cells. *Mol Biol Cell* 18: 1348-58.

Loft A, Forss I, Siersbæk M S, Schmidt S F, Larsen A-S B, Madsen J G S, Pisani D F, Nielsen R, Aagaard M M, Mathison A, et al. 2015. Browning of human adipocytes requires KLF11 and reprogramming of PPARγ superenhancers. *Genes Dev* 29: 7-22.

Loh Y-H, Wu Q, Chew J-L, Vega V B, Zhang W, Chen X, Bourque G, George J, Leong B, Liu J, et al. 2006, The Oct4 and Nanog transcription network regulates pluripotency in mouse embryonic stem cells. *Nat Genet* 38: 431-40.

Lovén J, Hoke H A, Lin C Y, Lau A, Orlando D A, Vakoc C R, Bradner J E, Lee T I, Young R A. 2013. Selective inhibition of tumor oncogenes by disruption of super-enhancers. *Cell* 153: 320-34.

Lujan E, Chanda S, Ahlenius H, Südhof T C, Wernig M. 2012. Direct conversion of mouse fibroblasts to self-renewing, tripotent neural precursor cells. *Proc Natl Acad Sci USA* 109: 2527-32.

Mansour M R, Abraham B J, Anders L, Berezovskaya A, Gutierrez A, Durbin A D, Etchin J, Lawton L, Sallan S E, Silverman L B, et al. 2014. An oncogenic super-enhancer formed through somatic mutation of a noncoding intergenic element. *Science* (80-).

Masui S. Nakatake Y, Toyooka Y, Shimosato D, Yagi R, Takahashi K, Okochi H, Okuda A, Matoba R, Sharov A A, et al. 2007. Pluripotency governed by Sox2 via regulation of Oct3/4 expression in mouse embryonic stem cells. Not Cell Biol 9: 625-35.

Mathelier A, Zhao X, Zhang A W, Parcy F, Worsley-Hunt R, Arenillas D J, Buchman S, Chen C, Chou A, Ienasescu H, et al. 2014. JASPAR 2014: an extensively expanded and updated open-access database of transcription factor binding profiles. *Nucleic Acids Res* 42: D142-7.

Matys V, Kel-Margoulis O V, Fricke E, Liebich I, Land S, Barre-Dirrie A, Reuter I, Chekmenev D, Krull M, Hornischer K, et al. 2006. TRANSFAC and its module TRANSCompel: transcriptional gene regulation in eukaryotes. *Nucleic Acids Res* 34: D108-10.

Maurano M T, Humbert R, Rynes E, Thurman R E, Haugen E, Wang H, Reynolds A P, Sandstrom R, Qu H, Brody J, et al. 2012. Systematic localization of common disease-associated variation in regulatory DNA. *Science* 337: 11905.

Medeiros L A, Dennis L M, Gill M E, Houbaviy H, Markoulaki S, Fu D, White A C, Kirak O, Sharp P A, Page D C, et al. 2011. Mir-290-295 deficiency in mice results in partially penetrant embryonic lethality and germ cell defects. *Proc Natl Acad Sci U S A* 108: 14163-8.

Mitsui K, Tokuzawa Y, Itoh H, Segawa K, Murakami M, Takahashi K, Maruyama M, Maeda M, Yamanaka S. 2003. The homeoprotein Nanog is required for maintenance of pluripotency in mouse epiblast and ES cells. *Cell* 113: 631-42.

Morris S A, Daley G Q. 2013. A blueprint for engineering cell fate: current technologies to reprogram cell identity. *Cell Res* 23: 33-48.

Nam Y-J, Lubczyk C, Bhakta M, Zang T, Fernandez-Perez A, McAnally J, Bassel-Duby R, Olson E N, Munshi N V. 2014. Induction of diverse cardiac cell types by reprogramming fibroblasts with cardiac transcription factors. *Development* 141: 4267-78.

Navarro P, Festuccia N, Colby D, Gagliardi A, Mullin N P, Zhang W, Karwacki-Neisius V, Osorno R, Kelly D, Robertson M, et al. 2012. OCT4/SOX2-independent Nanog autorepression modulates heterogeneous Nanog gene expression in mouse ES cells. *EMBO J* 31: 4547-62.

Neph S, Stergachis A B, Reynolds A, Sandstrom R, Berenstein E, Stamatoyannopoulos J A. 2012. Circuitry and dynamics of human transcription factor regulatory networks.*Cell* 150: 1274-86.

Nichols J, Zevnik B, Anastassiadis K, Niwa H, Klewe-Nebenius D, Chambers I, Schöler H, Smith A. 1998. Formation of pluripotent stem cells in the mammalian embryo depends on the POU transcription factor Oct4. *Cell* 95: 379-91.

Niwa H, Miyazaki J, Smith A G. 2000. Quantitative expression of Oct-3/4 defines differentiation, dedifferentiation or self-renewal of ES cells. *Nat Genet* 24: 372-6.

Novershtern N, Subramanian A, Lawton L N, Mak R H, Haining W N, McConkey M E, Habib N, Yosef N, Chang C Y, Shay T, et al. 2011. Densely interconnected transcriptional circuits control cell states in human hematopoiesis. *Cell* 144: 296-309.

Odom D T, Dowell R D, Jacobsen E S, Nekludova L, Rolfe P A, Danford T W, Gifford D K, Fraenkel E, Bell G I, Young R A. 2006. Core transcriptional regulatory circuitry in human hepatocytes. *Mol Syst Biol* 2: 2006.0017.

Odom D T, Zizlsperger N, Gordon D B, Bell G W, Rinaldi N J, Murray H L, Volkert T L, Schreiber J, Rolfe P A, Gifford D K, et al. 2004. Control of pancreas and liver gene expression by HNF transcription factors. *Science* 303: 1378-81.

Okumura-Nakanishi S, Saito M, Niwa H, Ishikawa F. 2005. Oct-3/4 and Sox2 regulate Oct-3/4 gene in embryonic stem cells. *J Biol Chem* 280: 5307-17.

Palii C G, Perez-Iratxeta C, Yao Z, Cao Y, Dai F, Davison J, Atkins H, Allan D, Dilworth F J, Gentleman R, et al. 2011. Differential genomic targeting of the transcription factor TAL1 in alternate haematopoietic lineages. *EMBO J* 30: 494-509.

Parker S C J, Stitzel M L, Taylor D L, Orozco J M, Erdos M R, Akiyama J A, van Bueren K L, Chines P S, Narisu N, Black B L, et al. 2013. Chromatin stretch enhancer states drive cell-specific gene regulation and harbor human disease risk variants. *Proc Natl Acad Sci U S A:*110: 17921-6.

Peter I S, Faure F, Davidson E H. 2012. Predictive computation of genomic logic processing functions in embryonic development. *Proc Natl Acad Sci U S A* 109: 16434-42.

Pique-Regi R, Degner J F, Pai A A, Gaffney D J, Gilad Y, Pritchard J K. 2011. Accurate inference of transcription factor binding from DNA sequence and chromatin accessibility data. *Genome Res* 21: 447-55.

Quintana A M, Zhou Y E, Pena J J, O'Rourke J P, Ness S A. 2011. Dramatic repositioning of c-Myb to different promoters during the cell. cycle observed by combining cell sorting with chromatin immunoprecipitation. *PLoS One* 6: e17362.

Rajapakse I, Perlman M D, Scalzo D, Kooperberg C, Groudine M, Kosak S T. 2009, The emergence of lineage-specific chromosomal topologies from coordinate gene regulation. *Proc Natl Acad Sci U S A* 106: 6679-84.

Robasky K, Bulyk M L. 2011. UniPROBE, update 2011: expanded content and search tools in the online database of protein-binding microarray data on protein-DNA interactions, *Nucleic Acids Res* 39: D124-8.

Rodda D J, Chew J-L, Lim Loh Y-H, Wang B, Ng H-H, Robson P. 2005. Transcriptional regulation of nanog by OCT4 and SOX2. *J Biol Chem* 280: 24731-7.

Roeder R G. 2005. Transcriptional regulation and the role of diverse coactivators in animal cells. *FEBS Lett* 579: 909-15.

Rolland T, Taşan M, Charioteaux B, Pevzner S J, Zhong Q, Sahni N, Yi S, Lemmens I, Fontanillo C, Mosca R, et al. 2014. A Proteome-Scale Map of the Human Interactome Network. *Cell* 159: 1212-1226.

Sanda T, Lawton L N, Barrasa M I, Fan Z P, Kohlhammer H, Gutierrez A, Ma W, Tatarek J, Ahn Y, Kelliher M A, et al. 2012. Core transcriptional regulatory circuit controlled by the TAL1 complex in human T cell acute lymphoblastic leukemia, *Cancer Cell* 22: 209-21.

Schmidt S F, Larsen B D, Loft A, Nielsen R, Madsen J G S, Mandrup S. 2015. Acute TNF-induced repression of cell identity genes is mediated by NFκB-directed redistribution of cofactors from super-enhancers. *Genome Res* gr.188300.114.

Siersbæk R, Baek S, Rabiee A, Nielsen R, Traynor S, Clark N, Sandelin A, Jensen O N, Sung M-H, Hager G L, et al. 2014a. Molecular architecture of transcription factor hotspots in early adipogenesis. *Cell Rep* 7: 1434-42.

Siersbæk R, Rabiee A, Nielsen R, Sidoli S, Traynor S, Loft A, La Cour Poulson L, Rogowska-Wrzesinska A, Jensen O N, Mandrup S. 2014b. Transcription factor cooperativity in early adipogenic hotspots and super-enhancers. *Cell Rep* 7: 1443-55.

Silva J, Nichols J, Theunissen T W, Guo G, van Oosten A L, Barrandon O, Wray J, Yamanaka S, Chambers I, Smith A. 2009, Nanog is the gateway to the pluripotent ground state. *Cell* 138: 722-37.

Sisodiya S M, Ragge N K, Cavalleri G L, Hever A, Lorenz B, Schneider A, Williamson K A, Stevens J M, Free S L, Thompson P J, et al. 2006. Role of SOX2 mutations in human hippocampal malformations and epilepsy. *Epilepsia* 47: 534-42.

Song K, Nam Y-J, Luo X, Qi X, Tan W, Huang G N, Acharya A, Smith C L, Tallquist M D, Neilson E G, et al. 2012. Heart repair by reprogramming non-myocytes with cardiac transcription factors. *Nature* 485: 599-604.

Spitz F, Furlong E E M. 2012. Transcription factors: from enhancer binding to developmental control. *Nat Rev Genet* 13: 613-26.

Stergachis A B, Neph S, Sandstrom R, Haugen E. Reynolds A P, Zhang M, Byron R, Canfield T, Stelhing-Sun S, Lee K, et al. 2014. Conservation of trans-acting circuitry during mammalian regulatory evolution. *Nature* 515: 365-370.

Sur I K, Hallikas O, Vähärautio A, Yan J, Turunen M, Enge M, Taipale M, Karhu A, Aaltonen L A, Taipale J. 2012. Mice lacking a Myc enhancer that includes human SNP rs6983267 are resistant to intestinal tumors. *Science* 338: 1360-3.

Takahashi K, Yamanaka S. 2006. Induction of pluripotent stem cells from mouse embryonic and adult fibroblast cultures by defined factors. *Cell* 126: 663-76.

Theunissen T W, van Oosten A L, Castelo-Branco G, Hall J, Smith A, Silva J C R. 2011. Nanog overcomes reprogramming barriers and induces pluripotency in minimal conditions. *Curr Biol* 21: 65-71.

Tomioka M, Nishimoto M, Miyagi S, Katayanagi T, Fukui N, Niwa H, Muramatsu M, Okuda A. 2002, Identification of Sox-2 regulatory region which is under the control of Oct-3/4-Sox-2 complex. *Nucleic Acids Res* 30: 3202-13.

Tsankov A M, Gu H, Akopian V, Ziller M J, Donaghey J, Amit I, Gnirke A, Meissner A. 2015. Transcription factor binding dynamics during human ES cell differentiation. *Nature* 518: 344-349.

Tuupanen S, Turunen M, Lehtonen R, Hallikas O, Vanharanta S, Kivioja T, Björklund M, Wei G, Yan J, Niittymäki I, et al. 2009. The common colorectal cancer predisposition SNP rs6983267 at chromosome 8q24 confers potential to enhanced Wnt signaling. *Nat Genet* 41: 885-90.

Usary J, Llaca V, Karaca G, Presswala S, Karaca M, He X, Langerød A, Kåresen R, Oh D S, Dressler L G, et al. 2004. Mutation of GATA3 in human breast tumors. *Oncogene* 23: 7669-78.

Van den Boogaard M, Wong L Y E, Tessadori F, Bakker M L, Dreizehnter L K, Walker V, Bezzina CR, 't Hoen P A C, Bakkers J, Barnett P, et al. 2012. Genetic variation in T-box binding element functionally affects SCN5A/SCN10A enhancer. *J Clin Invest* 122: 2519-30.

Wang K C, Yang Y W, Liu B, Sanyal A, Corces-Zimmerman R, Chen Y, Lajoie B R, Protacio A, Flynn R A, Gupta R A, et al. 2011a. A long noncoding RNA maintains active chromatin to coordinate homeotic gene expression. *Nature* 472: 120-4.

Wang W, Yang J, Liu H, Lu D, Chen X, Zenonos Z, Campos L S, Rad R, Guo G, Zhang S, et al. 2011b. Rapid and efficient reprogramming of somatic cells to induced pluripotent stem cells by retinoic acid receptor gamma and liver receptor homolog 1. *Proc Natl Acad Sci U S A* 108: 18283-8.

Wei G-H, Badis G, Berger M F, Kivioja T, Palin K, Enge M, Bonke M, Jolma A, Varjosalo M, Gehrke A R, et al. 2010. Genome-wide analysis of ETS-family DNA-binding in vitro and in vivo. *EMBO J* 29: 2147-60.

White J R, Weston K. 2000. Myb is required for self-renewal in a model system of early hematopoiesis. *Oncogene* 19: 1196-205.

Whyte W A, Orlando D A, Hnisz D, Abraham B J, Lin C Y, Kagey M H, Rahl P B, Lee T I, Young R A. 2013. Master transcription factors and mediator establish super-enhancers at key cell identity genes. *Cell* 153: 307-19.

Wong N, Wang X. 2015. miRDB: an online resource for microRNA target prediction and functional annotations. *Nucleic Acids Res* 43: D146-52.

Yan J, Enge M, Whitington T, Dave K, Liu J, Sur I, Schmierer B, Jolma A, Kivioja T, Taipale M, et al. 2013. Transcription factor binding in human cells occurs in dense clusters formed around cohesin anchor sites. *Cell* 154: 801-13.

Yang H-M, Do H-J, Kim D-K, Park J-K, Chang W-K, Chung H-M, Choi S-Y, Kim J-H. 2007. Transcriptional regulation of human Oct4 by steroidogenic factor-1. *J Cell Biochem* 101: 1198-209.

Yosef N, Shalek A K, Gaublomme J T, Jin H, Lee Y, Awasthi A, Wu C, Karwacz K, Xiao S, Jorgolli M, et al. 2013. Dynamic regulatory network controlling TH17 cell differentiation. *Nature* 496: 461-8.

Young R A, 2011. Control of the embryonic stein cell state. *Cell* 144: 940-54.

Yu J, Vodyanik M A, Smuga-Otto K, Antosiewicz-Bourget J, Franc J L, Tian S, Nie J, Jonsdottir G A, Ruotti V, Stewart R, et al. 2007. Induced pluripotent stem cell lines derived from human somatic cells. *Science* 318: 1917-20.

Zhang X, Yalcin S, Lee D-F, Yeh T-Y J, Lee S-M, Su J, Mungamuri S K, Rimmelé P, Kennedy M, Sellers R, et al. 2011. FOXO1 is an essential regulator of pluripotency in human embryonic stem cells. *Nat Cell Biol* 13: 1092-9.

Zhong S, He X, Bar-Joseph Z. 2013. Predicting tissue specific transcription factor binding sites. *BMC Genomics* 14: 796.

Zhou Q, Brown J, Kanarek A, Rajagopal J, Melton D A, 2008. In vivo reprogramming of adult pancreatic exocrine cells to beta-cells. *Nature* 455: 627-32.

Zhou Q, Li T, Price D H. 2012. RNA polymerase II elongation control. *Annu Rev Biochem* 81: 119-43.

Zhu Y, Richardson J A, Parada L F, Graff J M. 1998. Smad3 Mutant Mice Develop Metastatic Colorectal Cancer. *Cell* 94: 703-714.

Ziller M J, Edri R, Yaffe Y, Donaghey J, Pop R, Mallard W, Issner R, Clifford C A, Goren A, Xing J, et al. 2014. Dissecting neural differentiation regulatory networks through epigenetic footprinting. *Nature* 518: 3:55-9.

Zuber J, Rappaport A R, Luo W, Wang F, Chen C, Vaseva A V, Shi J, Weissmueller S, Fellmann C, Fellman C, et al. 2011. An integrated approach to dissecting oncogene addiction implicates a Myb-coordinated self-renewal program as essential for leukemia maintenance. *Genes Dev* 25: 1628-40.

Lengthy table referenced here

US11319591-20220503-T00001

Please refer to the end of the specification for access instructions.

Lengthy table referenced here

US11319591-20220503-T00002

Please refer to the end of the specification for access instructions.

Lengthy table referenced here

US11319591-20220503-T00003

Please refer to the end of the specification for access instructions.

Lengthy table referenced here

US11319591-20220503-T00004

Please refer to the end of the specification for access instructions.

Lengthy table referenced here

US11319591-20220503-T00005

Please refer to the end of the specification for access instructions.

Lengthy table referenced here

US11319591-20220503-T00006

Please refer to the end of the specification for access instructions.

Lengthy table referenced here

US11319591-20220503-T00007

Please refer to the end of the specification for access instructions.

Lengthy table referenced here

US11319591-20220503-T00008

Please refer to the end of the specification for access instructions.

Lengthy table referenced here

US11319591-20220503-T00009

Please refer to the end of the specification for access instructions.

Lengthy table referenced here

US11319591-20220503-T00010

Please refer to the end of the specification for access instructions.

Lengthy table referenced here

US11319591-20220503-T00011

Please refer to the end of the specification for access instructions.

| Lengthy table referenced here |
| --- |
| US11319591-20220503-T00012 |
| Please refer to the end of the specification for access instructions. |

| Lengthy table referenced here |
| --- |
| US11319591-20220503-T00014 |
| Please refer to the end of the specification for access instructions. |

| Lengthy table referenced here |
| --- |
| US11319591-20220503-T00013 |
| Please refer to the end of the specification for access instructions. |

| Lengthy table referenced here |
| --- |
| US11319591-20220503-T00015 |
| Please refer to the end of the specification for access instructions. |

LENGTHY TABLES

The patent contains a lengthy table section. A copy of the table is available in electronic form from the USPTO web site (https://seqdata.uspto.gov/?pageRequest=docDetail&DocID=US11319591B2). An electronic copy of the table will also be available from the USPTO upon request and payment of the fee set forth in 37 CFR 1.19(b)(3).

What is claimed is:

1. A method comprising:
  a) identifying a super-enhancer in a cancer cell or a cancer tissue using ChIP-SEQ data and identifying a group of transcription factor encoding genes whose expression is driven by the super-enhancer;
  b) identifying a set of autoregulated transcription factor encoding genes from the group of transcription factor encoding genes provided in a), wherein the autoregulated transcription factor encoding genes are able to bind to the super-enhancer driving expression of the transcription factor encoding gene;
  c) identifying a core regulatory circuitry of the cancer cell or tissue, wherein the core regulatory circuitry of the cancer cell or cancer tissue comprises a group of the set of autoregulated transcription factor encoding genes identified in b) which encode transcription factors that are predicted to bind to all other super-enhancers associated with driving expression of each of the other autoregulated transcription factor encoding genes of the group;
  d) identifying at least one component of the core regulatory circuitry of the cancer cell or cancer tissue identified in c), and quantifying expression or activity of the at least one component with a suitable assay, wherein the at least one component of the core regulatory circuitry of the cancer cell or cancer tissue is selected from the group consisting of: a transcription factor, a transcriptional activator, a transcriptional repressor, a transcriptional co-repressor a reprogramming factor, and a cell identity gene;
  e) contacting the cancer cell or cancer tissue with a test agent; and
  f) measuring whether the test agent modulates the expression or activity of the at least one component of the core regulatory circuitry of the cancer cell or cancer tissue with a suitable assay, wherein a test agent that modulates the expression or activity of the at least one component of the core regulatory circuitry of the cancer cell or cancer tissue is identified as a candidate anticancer agent;
  wherein each autoregulated transcription factor encoded by the group of autoregulated transcription factor encoding genes identified in c) is capable of binding to all other super-enhancers driving expression of each of the other autoregulated transcription factor encoding genes of the group if the super-enhancers driving expression of each of the other autoregulated transcription factor encoding genes are associated with at least one transcription factor binding motif for each of the autoregulated transcription factors of the group that is located between 10000 bp upstream and 10000 bp downstream of the super-enhancer associated with the autoregulated transcription factor encoding gene, and
  wherein steps a) through c) are performed using a computer.

2. The method of claim 1, wherein the at least one component of the core regulatory circuitry of the cancer cell or cancer tissue comprises a gene which encodes a reprogramming factor or a cell identity gene.

3. The method of claim 1, wherein the cell comprises a cancerous blood cell.

4. The method of claim 1, wherein the expression of the at least one component of the core regulatory circuitry of the cancer cell or cancer tissue is quantified in step d) by a hybridization based assay, a polymerase chain reaction assay, sequencing, or in situ hybridization.

* * * * *